US009944905B2

(12) United States Patent
De Jong et al.

(10) Patent No.: US 9,944,905 B2
(45) Date of Patent: Apr. 17, 2018

(54) FUMARATE REDUCTASES

(71) Applicant: DSM IP ASSETS B.V., Heerlen (NL)

(72) Inventors: René Marcel De Jong, Echt (NL); Zheng Zhao, Echt (NL); Ben Den Dulk, Echt (NL); Remko Tsjibbe Winter, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/103,237

(22) PCT Filed: Dec. 12, 2014

(86) PCT No.: PCT/EP2014/077638
§ 371 (c)(1),
(2) Date: Jun. 9, 2016

(87) PCT Pub. No.: WO2015/086839
PCT Pub. Date: Jun. 18, 2015

(65) Prior Publication Data

US 2016/0319245 A1 Nov. 3, 2016

(30) Foreign Application Priority Data

Dec. 12, 2013 (EP) .................................... 13196950

(51) Int. Cl.

| | |
|---|---|
| ***C12P 7/62*** | (2006.01) |
| ***C12P 7/46*** | (2006.01) |
| ***C12N 9/02*** | (2006.01) |
| ***C12P 19/34*** | (2006.01) |
| ***C12P 21/06*** | (2006.01) |
| ***C12N 15/00*** | (2006.01) |
| ***C12N 1/00*** | (2006.01) |
| ***C07H 21/04*** | (2006.01) |
| ***C07K 1/00*** | (2006.01) |

(52) U.S. Cl.
CPC ................ *C12N 9/001* (2013.01); *C12P 7/46* (2013.01); *C12Y 103/01006* (2013.01)

(58) Field of Classification Search
CPC .... C12N 9/001; C12P 7/46; C12Y 103/01006
USPC .......... 435/135, 145, 189, 69.1, 91.1, 320.1, 435/254.11, 254.21; 536/23.1, 23.2; 530/350
See application file for complete search history.

(56) References Cited

U.S. PATENT DOCUMENTS 9,012,187 B2 * 4/2015 Jansen ...................... C12P 7/44 435/145
9,353,387 B2 * 5/2016 Jansen ...................... C12P 7/46

FOREIGN PATENT DOCUMENTS

WO 2009065778 A1 5/2009

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Coustou V et al, "A mitochondrial NADH-dependent fumarate reductase involved in the production of succinate excreted by procyclic Trypanosoma brucei," Journal of Biological Chemistry, American Society for Biochemistry and Molecular Biology, vol. 280, No. 17, Apr. 29, 2005, pp. 16559-16570, XP002477924.
Besteiro S et al, Succinate secreted by Trypanosoma brucei is produced by a novel and unique glycosomal enzyme, NADH-dependent fumarate reductase11 , Journal of Biological Chemistry, American Society for Biochemistry and Molecular Biology, vol. 277, No. 41, Oct. 11, 2002, pp. 38001-38012, XP002477925.
International Search Report dated Apr. 14, 2015, issued in PCT/EP2014/077638.

* cited by examiner

*Primary Examiner* — Ganapathirama Raghu
(74) *Attorney, Agent, or Firm* — McBee Moore Woodward & Vanik IP, LLC; Susan McBee; Chester Moore

(57) ABSTRACT

The present invention relates to a variant polypeptide having fumarate reductase activity, which has modified NADP(H)-dependent and/or NAD(H)-dependent activity as compared with a reference polypeptide having fumarate reductase activity. Such a variant may be overexpressed in a host cell in order to improve production of a dicarboxylic acid.

18 Claims, 9 Drawing Sheets

SEQUENCE LISTING

```
<160> NUMBER OF SEQ ID NOS: 41

<210> SEQ ID NO 1
<211> LENGTH: 2626
<212> TYPE: DNA
<213> ORGANISM: Actinobacillus succinogenes

<400> SEQUENCE: 1

ttgcccatcg aacgtacaag tactcctctg ttctctcctt cctttgcttt gtgcgacacc      60

taactacata gtgtttaaag attacggata tttaacttac ttagaataat gccatttttt     120

tgagttataa taatcctacg ttagtgtgag cgggatttaa actgtgagga ccttaataca     180

ttcagacact tctgcggtat caccctactt attcccttcg agattatatc taggaaccca     240

tcaggttggt ggaagattac ccgttctaag acttttcagc ttcctctatt gatgttacac     300

ctggacaccc cttttctggc atccagtttt taatcttcag tggcatgtga gattctccga     360

aattaattaa agcaatcaca caattctctc ggataccacc tcggttgaaa ctgacaggtg     420

gtttgttacg catgctaatg caaaggagcc tatatacctt tggctcggct gctgtaacag     480

ggaatataaa gggcagcata atttaggagt ttagtgaact tgcaacattt actattttcc     540
```

```
cttcttacgt aaatattttt ctttttaatt ctaaatcaat ctttttcaat tttttgtttg    600
tattcttttc ttgcttaaat ctataactac aaaaaacaca tacataaact aaaaatgact    660
gatttgaaca aattggtcaa ggaattgaat gatttgggtt tgactgacgt caaggaaatt    720
gtctacaacc catcttacga acaattattc gaagaagaaa ccaagccagg tttggaaggt    780
ttcgacaagg gtactttgac cactttaggt gctgttgctg ttgacaccgg tattttcacc    840
ggtcgttctc caaaggacaa atacattgtt tgtgatgaaa ccaccaagga caccgtctgg    900
tggaactctg aagctgccaa gaacgataac aagccaatga ctcaagaaac ctggaaatct    960
ttgagagaat tggttgccaa gcaattgtct ggtaagagat tattcgttgt tgacgctttc   1020
tgtggtgctt ctgaaaagca cagaattggt gtcagaatgg tcactgaagt tgcttggcaa   1080
gctcatttcg tcaagaacat gttcatcaga ccaactgacg aagaattgaa gaacttcaag   1140
gctgacttca ccgttttgaa tggtgccaag tgtaccaacc caaactggaa ggaacaaggt   1200
ttgaactctg aaaactttgt tgctttcaac atcactgaag gtatccaatt gattggtggt   1260
acttggtacg gtggtgaaat gaagaagggt atgttctcca tgatgaacta tttcttgcca   1320
ttgaaaggtg ttgcttccat gcactgttct gccaatgtcg gtaaggatgg tgacgttgcc   1380
atcttcttcg gtctatccgg tactggtaag accactctat ccactgaccc aaagagacaa   1440
ttgattggtg atgacgaaca cggttgggac gaatctggtg tctttaactt tgaaggtggt   1500
tgttacgcca agaccatcaa cttatctcaa gaaaacgaac cagatatcta cggtgccatc   1560
cgtcgtgatg ctttgttgga aaacgttgtt gtcagagctg acggttctgt tgacttcgac   1620
gacggttcca agactgaaaa caccagagtt tcttacccaa tctaccacat tgacaacatt   1680
gtcagacctg tttccaaggc tggtcacgct accaaggtta tcttcttgac tgctgatgct   1740
ttcggtgtct tgccacctgt ttccaaattg actccagaac aaaccgaata ctacttcttg   1800
tccggtttca ctgccaaatt ggctggtact gaaagaggtg tcactgaacc aactccaact   1860
ttctctgctt gtttcggtgc tgctttctta tctttgcacc caatccaata cgctgatgtc   1920
ttggttgaaa gaatgaaggc ttctggtgct gaagcttact tggtcaacac cggttggaac   1980
ggtactggta agagaatctc catcaaggat accagaggta tcattgatgc tatcttggac   2040
ggttccattg aaaaggctga aatgggtgaa ttgccaatct tcaacttggc cattccaaag   2100
gctttgccag gtgttgaccc agccatctta gatccaagag acacctacgc tgacaaggct   2160
caatggcaag tcaaggctga agatttggct aacagattcg tcaagaactt tgtcaaatac   2220
actgctaacc cagaagctgc caaattggtt ggtgctggtc caaaggctta aaggagttaa   2280
aggcaaagtt ttcttttcta gagccgttcc cacaaataat tatacgtata tgcttctttt   2340
cgtttactat atatctatat ttacaagcct ttattcactg atgcaatttg tttccaaata   2400
ctttttttgga gatctcataa ctagatatca tgatggcgca acttggcgct atcttaatta   2460
ctctggctgc caggcccgtg tagagggccg caagaccttc tgtacgccat atagtctcta   2520
agaacttgaa caagtttcta gacctattgc cgcctttcgg atcgctattg ttcctccgga   2580
tcgatgtaca caaccgactg cacccaaacg aacacaaatc ttagca                  2626
```

<210> SEQ ID NO 2
<211> LENGTH: 4552
<212> TYPE: DNA
<213> ORGANISM: Saccharomyces cerevisiae

<400> SEQUENCE: 2

```
cggatcgatg tacacaaccg actgcaccca aacgaacaca aatcttagca gtgcgggcca     60
gaaaaaggaa gtgtttccct ccttcttgaa ttgatgttac cctcataaag cacgtggcct    120
cttatcgaga aagaaattac cgtcgctcgt gatttgtttg caaaaagaac aaaactgaaa    180
aaacccagac acgctcgact tcctgtcttc ctattgattg cagcttccaa tttcgtcaca    240
caacaaggtc ctagcgacgg ctcacaggtt ttgtaacaag caatcgaagg ttctggaatg    300
gcgggaaagg gtttagtacc acatgctatg atgcccactg tgatctccag agcaaagttc    360
gttcgatcgt actgttactc tctctctttc aaacagaatt gtccgaatcg tgtgacaaca    420
acagcctgtt ctcacacact cttttcttct aaccaagggg gtggtttagt ttagtagaac    480
ctcgtgaaac ttacatttac atatatataa acttgcataa attggtcaat gcaagaaata    540
catatttggt cttttctaat tcgtagtttt tcaagttctt agatgctttc tttttctctt    600
ttttacagat catcaaggaa gtaattatct actttttaca acaaatataa aacaatgtcc    660
tcttccaaga tcttggctgg tttgagagac aacttttctt tgttgggtga aaagaacaag    720
attttggtcg ccaacagagg tgaaatccca atcagaattt tcagatctgc tcacgaattg    780
tctatgagaa ctatcgccat ctactctcac gaagatagat tatccatgca cagattgaag    840
gctgatgaag cctacgttat cggtgaagaa ggtcaataca ccccagtcgg tgcttacttg    900
gccatggacg aaatcatcga aattgccaag aagcacaagg tcgatttcat ccacccaggt    960
tacggtttct tgtctgaaaa ctctgaattt gctgacaagg ttgttaaggc tggtattacc   1020
tggattggtc caccagctga agtcattgaa tctgttggtg acaaggtttc tgccagacat   1080
ttggctgctc gtgccaacgt tccaactgtc ccaggtactc caggtcctat cgaaaccgtt   1140
caagaagctc tagatttcgt caatgaatac ggttacccag ttatcatcaa ggctgctttc   1200
ggtggtggtg gtcgtggtat gagagttgtc agagaaggtg acgatgtcgc tgatgctttc   1260
caaagagcca cttctgaagc tagaactgct ttcggtaacg gtacttgttt cgtcgaaaga   1320
ttcttggaca agccaaagca cattgaagtt caattattag ctgacaacca cggtaacgtt   1380
gtccacttgt tcgaaagaga ctgttccgtc caaagacgtc accaaaaggt tgtcgaagtt   1440
gctccagcta agactttacc aagagaagtt agagatgcta tcttgaccga tgccgttaag   1500
ttggctaagg tttgtggtta cagaaacgct ggtactgctg aattcttggt tgacaaccaa   1560
aacagacatt acttcattga aatcaaccca agaattcaag tcgaacacac catcactgaa   1620
gaaatcactg gtattgacat tgtctccgct caaatccaaa tcgccgctgg tgctactttg   1680
actcaattag gtctattaca agacaaaatc accaccagag gtttctctat ccaatgtcgt   1740
atcaccactg aagatccatc caagaacttc caaccagaca ctggtcgttt ggaagtctac   1800
agatccgctg gtggtaacgg tgtcagattg gacggtggta acgcctacgc tggtgctacc   1860
atctctccac actacgactc catgttggtt aagtgttcct gttctggttc tacctacgaa   1920
attgtcagaa gaaagatgat cagagctttg attgaattca gaatcagagg tgtcaagacc   1980
aacatcccat tcttgttgac tttgttgacc aacccagttt tcattgaagg tacctactgg   2040
accactttca tcgatgacac tccacaattg ttccaaatgg tttcctctca aaacagagct   2100
caaaaattgt tgcactactt ggctgacttg gccgtcaacg gttcctctat caagggtcaa   2160
atcggtttac caaagttgaa gtccaaccct tccgttccac atttgcacga tgctcaaggt   2220
aatgtcatca acgttaccaa atctgcccca ccatccggtt ggagacaagt cttgttggaa   2280
aagggtccat ccgaatttgc caagcaagtc agacaattca acggtacttt gttgatggac   2340
accacctgga gagatgctca ccaatctttg ctagctacca gagtcagaac tcacgatttg   2400
```

```
gccaccattg ctccaaccac tgctcacgct ttggctggtg cctttgcttt ggaatgttgg   2460

ggtggtgcta ctttcgatgt cgccatgaga ttcttgcatg aggacccatg ggaaagattg   2520

agaaaattga gatctttggt cccaaacatt ccattccaaa tgttgttgag aggtgctaac   2580

ggtgttgctt actcctcttt gccagacaac gccattgacc atttcgttaa gcaagccaag   2640

gacaatggtg ttgacatttt cagagtcttt gacgctttga acgacttgga acaattgaag   2700

gttggtgtta atgctgtcaa gaaggctggt ggtgttgtcg aagctaccgt ttgttactct   2760

ggtgacatgt tgcaaccagg taagaaatac aacttggact actacttaga agttgtcgaa   2820

aagatcgttc aaatgggtac tcacatcttg ggtatcaagg acatggctgg taccatgaag   2880

ccagctgctg ccaaattgtt gattggttct ttacgtacca gatacccaga cttgccaatc   2940

cacgttcact ctcatgactc cgctggtact gctgttgctt ccatgactgc ttgtgctttg   3000

gccggtgctg atgttgttga cgttgccatt aactccatgt ccggtttgac ctctcaacca   3060

tctattaacg ctttgttggc ctccttggaa ggtaacattg acactggtat caacgtcgaa   3120

cacgttagag aattggacgc ttactgggct gaaatgagat tattatactc ttgtttcgaa   3180

gctgacttga agggtccaga ccctgaagtt taccaacacg aaattccagg tggtcaattg   3240

accaacttgt tgttccaagc tcaacaatta ggtctaggtg aacaatgggc tgaaaccaag   3300

agagcttaca gagaagctaa ctacttgttg ggtgacattg ttaaggtcac cccaacttct   3360

aaggtcgttg gtgatttggc tcaattcatg gtttctaaca aattgacttc tgatgacatc   3420

agaagattag ctaactcttt ggacttccca gactccgtta tggacttctt cgaaggtttg   3480

atcggtcaac catacggtgg tttcccagaa ccattgagat ccgatgtttt gagaaacaag   3540

cgtcgtaaat tgacttgtag accaggttta gaattggaac cattcgattt ggaaaagatc   3600

agagaagatt tgcaaaacag attcggtgat atcgatgaat gtgatgttgc ctcctacaac   3660

atgtatcctc gtgtctacga agatttccaa aagattagag aaacttacgg tgacttgtct   3720

gtcttaccaa ccaagaactt cttggctcca gctgaaccag acgaagaaat cgaagtcacc   3780

attgaacaag gtaagacttt gattatcaaa ttacaagctg ttggtgattt gaacaagaaa   3840

accggtcaaa gagaagtcta cttcgaattg aacggtgaat tgagaaagat cagagttgct   3900

gacaaatctc aaaacattca atctgttgcc aagccaaagg ctgatgtcca cgacacccac   3960

caaatcggtg ctccaatggc tggtgtcatc attgaagtca aggttcacaa gggttctttg   4020

gtcaagaagg gtgaatctat cgccgttttg tctgctatga agatggaaat ggttgtttcc   4080

tctccagctg atggtcaagt caaagatgtc tttatccgtg acggtgaatc cgtcgatgct   4140

tctgacttgt tggttgtttt ggaagaagaa actctaccac cttctcaaaa gaaataaagc   4200

gaatttctta tgatttatga tttttattat taaataagtt ataaaaaaaa taagtgtata   4260

caaattttaa agtgactctt aggttttaaa acgaaaattc ttattcttga gtaactcttt   4320

cctgtaggtc aggttgcttt ctcaggtata gcatgaggtc gctcttattg accacacctc   4380

taccggcatg ccgagcaaat gcctgcaaat cgctccccat ttcacccaat tgtagatatg   4440

ctaactccag caatgagttg atgaatctcg gtgtgtattt tatgtcctca gaggacaacc   4500

tcacgctttc cggcatcttc cagaccacag tatatccatc cgcctcctgt tg           4552
```

<210> SEQ ID NO 3
<211> LENGTH: 1572
<212> TYPE: DNA
<213> ORGANISM: Artificial sequence
<220> FEATURE:

<223> OTHER INFORMATION: KanMX selection marker

<400> SEQUENCE: 3

```
tcgtacgctg caggtcgacg aattctaccg ttcgtataat gtatgctata cgaagttata     60
gatctgttta gcttgcctcg tccccgccgg gtcacccggc cagcgacatg gaggcccaga    120
ataccctcct tgacagtctt gacgtgcgca gctcaggggc atgatgtgac tgtcgcccgt    180
acatttagcc catacatccc catgtataat catttgcatc catacatttt gatggccgca    240
cggcgcgaag caaaaattac ggctcctcgc tgcagacctg cgagcaggga aacgctcccc    300
tcacagacgc gttgaattgt ccccacgccg cgcccctgta gagaaatata aaaggttagg    360
atttgccact gaggttcttc tttcatatac ttccttttaa aatcttgcta ggatacagtt    420
ctcacatcac atccgaacat aaacaaccat gggtaaggaa aagactcacg tttcgaggcc    480
gcgattaaat tccaacatgg atgctgattt atatgggtat aaatgggctc gcgataatgt    540
cgggcaatca ggtgcgacaa tctatcgatt gtatgggaag cccgatgcgc cagagttgtt    600
tctgaaacat ggcaaaggta gcgttgccaa tgatgttaca gatgagatgg tcagactaaa    660
ctggctgacg gaatttatgc ctcttccgac catcaagcat tttatccgta ctcctgatga    720
tgcatggtta ctcaccactg cgatccccgg caaaacagca ttccaggtat tagaagaata    780
tcctgattca ggtgaaaata ttgttgatgc gctggcagtg ttcctgcgcc ggttgcattc    840
gattcctgtt tgtaattgtc cttttaacag cgatcgcgta tttcgtctcg ctcaggcgca    900
atcacgaatg aataacggtt tggttgatgc gagtgatttt gatgacgagc gtaatggctg    960
gcctgttgaa caagtctgga aagaaatgca taagcttttg ccattctcac cggattcagt   1020
cgtcactcat ggtgatttct cacttgataa ccttattttt gacgagggga aattaatagg   1080
ttgtattgat gttggacgag tcggaatcgc agaccgatac caggatcttg ccatcctatg   1140
gaactgcctc ggtgagtttt ctccttcatt acagaaacgg ctttttcaaa aatatggtat   1200
tgataatcct gatatgaata aattgcagtt tcatttgatg ctcgatgagt ttttctaatc   1260
agtactgaca ataaaaagat tcttgttttc aagaacttgt catttgtata gtttttttat   1320
attgtagttg ttctatttta atcaaatgtt agcgtgattt atattttttt tcgcctcgac   1380
atcatctgcc cagatgcgaa gttaagtgcg cagaaagtaa tatcatgcgt caatcgtatg   1440
tgaatgctgg tcgctatact gctgtcgatt cgatactaac gccgccatcc agtgtcgaaa   1500
acgagctcat aacttcgtat aatgtatgct atacgaacgg tagaattcga tatcagatcc   1560
actagtggcc ta                                                        1572
```

<210> SEQ ID NO 4
<211> LENGTH: 2260
<212> TYPE: DNA
<213> ORGANISM: Aspergillus niger

<400> SEQUENCE: 4

```
aacgttgtcc aggtttgtat ccacgtgtgt ccgttccgcc aatattccgc gtgcccgcgg     60
aaccgccaga tattcattac ttgacgcaaa agcgtttgaa ataatgacga aaaagaagga    120
agaaaaaaaa agaaaaatac cgcttctagg cgggttatct actgatccga gcttccacta    180
ggatagcacc caaacacctg catatttgga cgacctttac ttacaccacc aaaaaccact    240
ttcgcctctc ccgcccctga taacgtccac taattgagcg attacctgag cggtcctctt    300
ttgtttgcag catgagactt gcatactgca aatcgtaagt agcaacgtgt caaggtcaaa    360
actgtatgga aaccttgtca cctcacttaa ttctagctag cctaccctgc aagtcaagag    420
```

```
gtgtccgtga ttcctagcca cctcaaggta tgcctctccc cggaaactgt ggccttttct    480

ggcacacatg atctccacga tttcaacata taaatagctt ttgataatgg caatattaat    540

caaatttatt ttacttcttt cttgtaacat ctctcttgta atcccttatt ccttctagct    600

atttttcata aaaaaccaag caactgctta tcaacacaca aacactaaat caaaatgaac    660

gttgaaactt ctttgccagg ttcttctggt tctgacttgg aaactttcca ccacgaaacc    720

aagaagcatg ccaaccacga ctctggtatt tccgtcaacc atgaagctga aattggtgtt    780

aaccacactt tcgaaaagcc aggtccagtt ggtatcagag aaagattacg tcacttcacc    840

tgggcttggt acactttgac catgtcctgt ggtggtttgg ctttgttgat tgtcaaccaa    900

ccacacgact tcaagggttt gaaagatatt gccagagttg tctactgttt gaacttggct    960

ttctttgtta tcgttacctc tttgatggcc atcagattca tcttgcacaa gaacatgtgg   1020

gaatccttgg gtcacgacag agaaggtttg tttttcccaa ctttctggtt atccattgct   1080

accatgatca ctggtttgta caagtgtttc ggtgatgatg ctaacgaaaa gttcaccaag   1140

tgtttgcaag ttttgttctg gatctactgt ggttgtacca tgatcactgc tgtcggtcaa   1200

tactctttcg tctttgctac ccacaaatac gaattgcaca ccatgatgcc atcctggatc   1260

ttgccagctt tcccagttat gttgtctggt actatcgcct ccgtcatcgg ttctggtcaa   1320

ccagcttccg atggtattcc aattattatt gctggtatca ctttccaagg tttaggtttc   1380

tccatctcct tcatgatgta cgctcactac attggtagat tgatggaagt tggtttacca   1440

tctccagaac acagaccagg tatgttcatc tgtgttggtc ctccagcttt caccgctttg   1500

gctttggtcg gtatggccaa ggctttacca gacgacttcc aaattgtcgg tgaccctcac   1560

gctgtcattg acggtcgtgt tatgttgttc ttggctgtct ctgctgccat cttcttatgg   1620

gctttgtctt tctggttctt ctgtatcgct gttgttgctg ttgtcagatc tccaccaaag   1680

ggtttccatt tgaactggtt tgccatggtt ttcccaaaca ctggtttcac cttggctacc   1740

atcactttgg ctaacatgtt cgaatctcca ggtgtcaagg gtgttgccac tgctatgtcc   1800

ctatgtgtca tcatcatgtt tattttcgtc ttggtttctg ccatcagagc tgtcatcaga   1860

aaggacatca tgtggccagg tcaagatgaa gatgtttctg aataaagagt aataattatt   1920

gcttccatat aatattttta tatacctctt atttttatgt attagttaat taagtatttt   1980

tatctatctg cttatcattt tcttttcata tagggggggt tggtgttttc ttgcccatca   2040

gattgatgtc ctccaactcg gcactatttt acaaagggtt tttttgtaag agaaggagaa   2100

gacagatact aaaccatacg ttactcgaaa caaaaaaaaa aaaaatggaa aaagctgcta   2160

tcaacaaaag acggcctcat caaacctaaa gaaaccatgt cagcgtcctc aaataaccac   2220

aaacatcctt cccatatgct cggtcgtgct tgttgtacct                         2260
```

<210> SEQ ID NO 5
<211> LENGTH: 2032
<212> TYPE: DNA
<213> ORGANISM: Saccharomyces cerevisiae

<400> SEQUENCE: 5

```
aaataaccac aaacatcctt cccatatgct cggtcgtgct tgttgtacct gtgcctactt     60

ggcttcacat acgttgcata cgtcgatata gataataatg ataatgacag caggattatc    120

gtaatacgta atagttgaaa atctcaaaaa tgtgtgggtc attacgtaaa taatgatagg    180

aatgggattc ttctattttt cctttttcca ttctagcagc cgtcgggaaa acgtggcatc    240
```

```
ctctctttcg ggctcaattg gagtcacgct gccgtgagca tcctctcttt ccatatctaa    300
caactgagca cgtaaccaat ggaaaagcat gagcttagcg ttgctccaaa aaagtattgg    360
atggttaata ccatttgtct gttctcttct gactttgact cctcaaaaaa aaaaaatcta    420
caatcaacag atcgcttcaa ttacgccctc acaaaaactt ttttccttct tcttcgccca    480
cgttaaattt tatccctcat gttgtctaac ggatttctgc acttgattta ttataaaaag    540
acaaagacat aatacttctc tatcaatttc agttattgtt cttccttgcg ttattcttct    600
gttcttcttt ttcttttgtc atatataacc ataaccaagt aatacatatt caaaatggtt    660
aaggttgcca tcttaggtgc ttctggtggt gtcggtcaac cattatctct attattgaaa    720
ttgtctccat acgtttctga attggctttg tacgatatca gagctgctga aggtattggt    780
aaggatttgt cccacatcaa caccaactcc tcttgtgttg gttacgacaa ggattccatc    840
gaaaacactt tgtccaatgc tcaagttgtc ttgattccag ctggtgttcc aagaaagcca    900
ggtttgacca gagatgattt gttcaagatg aacgctggta tcgttaagtc tttggttact    960
gctgtcggta aatttgcccc aaacgctcgt atcttagtca tctccaaccc tgttaactct   1020
ttggttccaa ttgccgttga aactttgaag aagatgggta agttcaagcc aggtaacgtt   1080
atgggtgtca ccaacttgga tttggtcaga gctgaaactt tcttggttga ctacttgatg   1140
ttgaagaacc caaagatcgg tcaagaacaa gacaagacca ccatgcacag aaaggtcacc   1200
gtcatcggtg gtcactctgg tgaaaccatc attccaatca tcactgacaa atccttggtt   1260
ttccaattgg acaagcaata cgaacatttc atccacagag tccaattcgg tggtgacgaa   1320
attgtcaagg ccaagcaagg tgccggttct gctaccttgt ccatggcttt cgctggtgcc   1380
aaatttgctg aagaagtctt acgttctttc cacaacgaaa agccagaaac tgaatctttg   1440
tctgctttcg tctacttgcc aggtttgaag aacggtaaga aggctcaaca attagtcggt   1500
gacaactcca ttgaatactt ctctttgcca attgttttga gaaacggttc cgttgtttcc   1560
attgacactt ctgttttgga aaaattgtct ccaagagaag aacaattggt caacactgct   1620
gtcaaggaat tgagaaagaa cattgaaaag ggtaagtctt tcatcttgga cagttaaagt   1680
ctgaagaatg aatgatttga tgatttcttt ttccctccat ttttcttact gaatatatca   1740
atgatataga cttgtatagt ttattatttc aaattaagta gctatatata gtcaagataa   1800
cgtttgtttg acacgattac attattcgtc gacatctttt ttcagcctgt cgtggtagca   1860
atttgaggag tattattaat tgaataggtt cattttgcgc tcgcataaac agttttcgtc   1920
agggacagta tgttggaatg agtggtaatt aatggtgaca tgacatgtta tagcaatacc   1980
tcgaaacctt cgaatccagc cagcatgtcg acacccacaa gatgtagtgc ac           2032
```

<210> SEQ ID NO 6
<211> LENGTH: 3056
<212> TYPE: DNA
<213> ORGANISM: Escherichia coli

<400> SEQUENCE: 6

```
gaaaccttcg aatccagcca gcatgtcgac acccacaaga tgtagtgcac gtgccgtaaa     60
aactaaaacg agcccccacc aaagaacaaa aaagaaggtg ctgggccccc actttcttcc    120
cttgcacgtg ataggaagat ggctacagaa acaagaagat ggaaatcgaa ggaaagaggg    180
agactggaag ctgtaaaaac tgaaatgaaa aaaaaaaaaa aaaaaaaaaa caagaagctg    240
aaaatggaag actgaaattt gaaaaatggt aaaaaaaaaa aagaaacacg aagctaaaaa    300
cctggattcc attttgagaa gaagcaagaa aggtaagtat ggtaacgacc gtacaggcaa    360
```

```
gcgcgaaggc aaatggaaaa gctggagtcc ggaagataat catttcatct tcttttgtta    420
gaacagaaca gtggatgtcc ctcatctcgg taacgtattg tccatgccct agaactctct    480
gtccctaaaa agaggacaaa aacccaatgg tttccccagc ttccagtgga gccaccgatc    540
ccactggaaa ccactggaca ggaagagaaa atcacggact tcctctattg aaggataatt    600
caacactttc accagatccc aaatgtcccg cccctattcc cgtgttccat cacgtaccat    660
aacttaccat ttcatcacgt tctctatggc acactggtac tgcttcgact gctttgcttc    720
atcttctcta tgggccaatg agctaatgag cacaatgtgc tgcgaaataa agggatatct    780
aatttatatt attacattat aatatgtact agtgtggtta ttggtaattg tacttaattt    840
tgatatataa agggtggatc tttttcattt tgaatcagaa ttggaattgc aacttgtctc    900
ttgtcactat tacttaatag taattatatt tcttattaac cttttttttta agtcaaaaca    960
ccaaggacaa gaactactct tcaaaggtat ttcaagttat catacgtgtc acacacgctt   1020
cacagtttca agtaaaaaaa aagaatatta cacaatgtcc aacaagcctt tcatctacca   1080
agctccattc ccaatgggta aggacaacac tgaatactac ttgttgactt ctgactacgt   1140
ttccgttgct gatttcgatg gtgaaaccat cttgaaggtt gaaccagaag ccttgacttt   1200
gttggctcaa caagccttcc acgatgcttc tttcatgttg cgtccagctc accaaaagca   1260
agttgctgcc attttgcacg acccagaagc ctccgaaaac gacaaatacg ttgctttgca   1320
attcttgaga aactctgaaa ttgctgccaa gggtgtctta ccaacttgtc aagacactgg   1380
tactgccatc attgtcggta agaagggtca aagagtctgg accggtggtg gtgacgaaga   1440
aactctatcc aagggtgttt acaacactta cattgaagat aatttacgtt actctcaaaa   1500
tgctgctttg gacatgtaca aggaagtcaa cactggtact aacttgccag ctcaaatcga   1560
cttatacgct gttgacggtg acgaatacaa gttcttgtgt gttgccaagg gtggtggttc   1620
tgctaacaag acctacttgt accaagaaac caaggctttg ttgactccag gtaaattgaa   1680
gaacttcttg gtcgaaaaga tgagaacttt gggtactgct gcttgtccac cataccacat   1740
tgctttcgtt atcggtggta cttccgctga aaccaacttg aaaaccgtca aattggcttc   1800
cgctcactac tacgatgaat tgccaactga aggtaacgaa cacggtcaag ccttcagaga   1860
tgtccaattg gaacaagaat tgttggaaga agctcaaaaa ttaggtttgg gtgctcaatt   1920
tggtggtaaa tactttgctc acgatatcag agttatcaga ttaccaagac atggtgcttc   1980
ttgtccagtt ggtatgggtg tttcctgttc tgctgacaga aacatcaagg ccaagatcaa   2040
cagagaaggt atctggattg aaaaattgga acacaaccca ggtcaataca tcccacaaga   2100
attgagacaa gctggtgaag gtgaagctgt caaggttgac ttgaacagac caatgaagga   2160
aatcttggct caattatctc aatacccagt ttccaccaga ttatctttga ccggtactat   2220
cattgtcggt cgtgacattg ctcatgccaa gttgaaggaa ttgattgatg ctggtaagga   2280
attgcctcaa tacatcaagg accatccaat ctactacgct ggtccagcca agaccccagc   2340
tggttaccca tctggttctt tgggtccaac caccgctggt agaatggact cttacgttga   2400
cttgctacaa tctcacggtg gttccatgat catgttggct aagggtaaca gatctcaaca   2460
agtcaccgat gcttgtcaca agcacggtgg tttctatttg ggttccattg gtggtccagc   2520
tgctgtcttg gctcaacaat ctatcaagca cttggaatgt gttgcttacc cagaattggg   2580
tatggaagcc atctggaaga ttgaagtcga agatttccca gctttcatct tagtcgatga   2640
caagggtaac gacttcttcc aacaaattgt caacaagcaa tgtgccaact gtaccaagta   2700
```

```
aaataaagca atcttgatga ggataatgat tttttttga atatacataa atactaccgt   2760

ttttctgcta gattttgtga agacgtaaat aagtacatat tactttttaa gccaagacaa   2820

gattaagcat taactttacc cttttctctt ctaagtttca atactagtta tcactgttta   2880

aaagttatgg cgagaacgtc ggcggttaaa atatattacc ctgaacgtgg tgaattgaag   2940

ttctaggatg gtttaaagat ttttcctttt tgggaaataa gtaaacaata tattgctgcc   3000

ttcctcaaag ccaaagttcg cgttccgacc ttgcctccca aatccgagtt gcgatt       3056
```

<210> SEQ ID NO 7
<211> LENGTH: 1335
<212> TYPE: DNA
<213> ORGANISM: Artificial sequence
<220> FEATURE:
<223> OTHER INFORMATION: nourseothricin selection marker

<400> SEQUENCE: 7

```
tcgtacgctg caggtcgacg aattctaccg ttcgtataat gtatgctata cgaagttata     60

gatctgttta gcttgcctcg tccccgccgg gtcacccggc cagcgacatg gaggcccaga    120

ataccctcct tgacagtctt gacgtgcgca gctcaggggc atgatgtgac tgtcgcccgt    180

acatttagcc catacatccc catgtataat catttgcatc catacatttt gatggccgca    240

cggcgcgaag caaaaattac ggctcctcgc tgcagacctg cgagcaggga aacgctcccc    300

tcacagacgc gttgaattgt ccccacgccg cgcccctgta gagaaatata aaaggttagg    360

atttgccact gaggttcttc tttcatatac ttccttttaa aatcttgcta ggatacagtt    420

ctcacatcac atccgaacat aaacaaccat gggtaccact cttgacgaca cggcttaccg    480

gtaccgcacc agtgtcccgg gggacgccga ggccatcgag gcactggatg ggtccttcac    540

caccgacacc gtcttccgcg tcaccgccac cggggacggc ttcaccctgc gggaggtgcc    600

ggtggacccg cccctgacca aggtgttccc cgacgacgaa tcggacgacg aatcggacga    660

cggggaggac ggcgacccgg actcccggac gttcgtcgcg tacggggacg acggcgacct    720

ggcgggcttc gtggtcgtct cgtactccgg ctggaaccgc cggctgaccg tcgaggacat    780

cgaggtcgcc ccggagcacc gggggcacgg ggtcgggcgc gcgttgatgg ggctcgcgac    840

ggagttcgcc cgcgagcggg gcgccgggca cctctggctg gaggtcacca acgtcaacgc    900

accggcgatc cacgcgtacc ggcggatggg gttcaccctc tgcggcctgg acaccgccct    960

gtacgacggc accgcctcgg acggcgagca ggcgctctac atgagcatgc cctgccccta   1020

atcagtactg acaataaaaa gattcttgtt ttcaagaact tgtcatttgt atagtttttt   1080

tatattgtag ttgttctatt ttaatcaaat gttagcgtga tttatatttt ttttcgcctc   1140

gacatcatct gcccagatgc gaagttaagt gcgcagaaag taatatcatg cgtcaatcgt   1200

atgtgaatgc tggtcgctat actgctgtcg attcgatact aacgccgcca tccagtgtcg   1260

aaaacgagct cataacttcg tataatgtat gctatacgaa cggtagaatt cgatatcaga   1320

tccactagtg gccta                                                    1335
```

<210> SEQ ID NO 8
<211> LENGTH: 4429
<212> TYPE: DNA
<213> ORGANISM: Trypanosoma brucei

<400> SEQUENCE: 8

```
aaagccaaag ttcgcgttcc gaccttgcct cccaaatccg agttgcgatt gtgcttagtc     60

aaaaaattag ccttttaatt ctgctgtaac ccgtacatgc ccaaaatagg gggcgggtta    120
```

```
cacagaatat ataacatcgt aggtgtctgg gtgaacagtt tattcctggc atccactaaa    180
tataatggag cccgcttttt aagctggcat ccagaaaaaa aaagaatccc agcaccaaaa    240
tattgttttc ttcaccaacc atcagttcat aggtccattc tcttagcgca actacagaga    300
acaggggcac aaacaggcaa aaaacgggca caacctcaat ggagtgatgc aacctgcctg    360
gagtaaatga tgacacaagg caattgaccc acgcatgtat ctatctcatt ttcttacacc    420
ttctattacc ttctgctctc tctgatttgg aaaaagctga aaaaaaaggt tgaaaccagt    480
tccctgaaat tattccccta cttgactaat aagtatataa agacggtagg tattgattgt    540
aattctgtaa atctatttct taaacttctt aaattctact tttatagtta gtcttttttt    600
tagttttaaa acaccaagaa cttagtttcg aataaacaca cataaacaaa caaaatggtt    660
gatggtagat cttctgcttc cattgttgcc gttgacccag aaagagctgc cagagaaaga    720
gatgctgctg ccagagcttt gttgcaagac tctccattgc acaccaccat gcaatacgct    780
acctctggtt tggaattgac tgttccatac gctttgaagg ttgttgcttc tgctgacact    840
ttcgacagag ccaaggaagt tgctgatgaa gtcttgagat gtgcctggca attggctgac    900
accgttttga actctttcaa cccaaactct gaagtctctt tagtcggtag attaccagtc    960
ggtcaaaagc atcaaatgtc tgctccattg aaacgtgtca tggcttgttg tcaaagagtc   1020
tacaactcct ctgctggttg tttcgaccca tccactgctc cagttgccaa ggctttgaga   1080
gaaattgctt tgggtaagga aagaaacaat gcttgtttgg aagctttgac tcaagcttgt   1140
accttgccaa actctttcgt cattgatttc gaagctggta ctatctccag aaagcacgaa   1200
cacgcttctt tggatttggg tggtgtttcc aagggttaca tcgtcgatta cgtcattgac   1260
aacatcaatg ctgctggttt ccaaaacgtt ttctttgact ggggtggtga ctgtcgtgcc   1320
tccggtatga acgccagaaa cactccatgg gttgtcggta tcactagacc tccttccttg   1380
gacatgttgc caaaccctcc aaaggaagct tcttacatct ccgtcatctc tttggacaat   1440
gaagctttgg ctacctctgg tgattacgaa aacttgatct acactgctga cgataaacca   1500
ttgacctgta cctacgattg gaaaggtaag gaattgatga agccatctca atccaatatc   1560
gctcaagttt ccgtcaagtg ttactctgcc atgtacgctg acgctttggc taccgcttgt   1620
ttcatcaagc gtgacccagc caaggtcaga caattgttgg atggttggag atacgttaga   1680
gacaccgtca gagattaccg tgtctacgtc agagaaaacg aaagagttgc caagatgttc   1740
gaaattgcca ctgaagatgc tgaaatgaga aagagaagaa tttccaacac tttaccagct   1800
cgtgtcattg ttgttggtgg tggtttggct ggtttgtccg ctgccattga agctgctggt   1860
tgtggtgctc aagttgtttt gatggaaaag gaagccaagt tgggtggtaa ctctgccaag   1920
gctacctctg gtatcaacgg ttggggtact agagcccaag ctaaggcttc cattgtcgat   1980
ggtggtaagt acttcgaaag agatacctac aagtctggta tcggtggtaa caccgatcca   2040
gctttggtta agactttgtc catgaaatct gctgacgcta tcggttggtt gacttctcta   2100
ggtgttccat tgactgtttt gtcccaatta ggtggtcact ccagaaagag aactcacaga   2160
gccccagaca agaaggatgg tactccattg ccaattggtt tcaccatcat gaaaacttta   2220
gaagatcatg ttagaggtaa cttgtccggt agaatcacca tcatggaaaa ctgttccgtt   2280
acctctttgt tgtctgaaac caaggaaaga ccagacggta ctaagcaaat cagagttacc   2340
ggtgtcgaat tcactcaagc tggttctggt aagaccacca ttttggctga tgctgttatc   2400
ttggccaccg gtggtttctc caacgacaag actgctgatt ctttgttgag agaacatgcc   2460
```

```
ccacacttgg ttaacttccc aaccaccaac ggtccatggg ctactggtga tggtgtcaag   2520

ttggctcaaa gattaggtgc tcaattggtc gatatggaca aggttcaatt gcacccaact   2580

ggtttgatca acccaaagga cccagccaac ccaaccaaat tcttgggtcc agaagctcta   2640

agaggttctg gtggtgtttt gttgaacaaa caaggtaaga gatttgtcaa cgaattggat   2700

ttgagatctg ttgtttccaa ggccatcatg gaacaaggtg ctgaataccc aggttctggt   2760

ggttccatgt ttgcttactg tgtcttgaac gctgctgctc aaaaattgtt tggtgtttcc   2820

tctcacgaat tctactggaa gaagatgggt ttgttcgtca aggctgacac catgagagac   2880

ttggctgctt tgattggttg tccagttgaa tccgttcaac aaactttaga agaatacgaa   2940

agattatcca tctctcaaag atcttgtcca attaccagaa aatctgttta cccatgtgtt   3000

ttgggtacta aaggtccata ctatgtcgcc tttgtcactc catctatcca ctacaccatg   3060

ggtggttgtt tgatttctcc atctgctgaa atccaaatga agaacacttc ttccagagcc   3120

ccattgtccc actccaaccc aatcttgggt ttattcggtg ctggtgaagt caccggtggt   3180

gtccacggtg gtaacagatt aggtggtaac tctttgttgg aatgtgttgt tttcggtaga   3240

attgccggtg acagagcttc taccattttg caaagaaagt cctctgcttt gtctttcaag   3300

gtctggacca ctgttgtttt gagagaagtc agagaaggtg gtgtctacgg tgctggttcc   3360

cgtgtcttga gattcaactt accaggtgct ctacaaagat ctggtctatc cttgggtcaa   3420

ttcattgcca tcagaggtga ctgggacggt caacaattga ttggttacta ctctccaatc   3480

actttgccag acgatttggg tatgattgac attttggcca gatctgacaa gggtacttta   3540

cgtgaatgga tctctgcttt ggaaccaggt gacgctgtcg aaatgaaggc ttgtggtggt   3600

ttggtcatcg aaagaagatt atctgacaag cacttcgttt tcatgggtca cattatcaac   3660

aagctatgtt tgattgctgg tggtactggt gttgctccaa tgttgcaaat catcaaggcc   3720

gctttcatga agccattcat cgacactttg gaatccgtcc acttgatcta cgctgctgaa   3780

gatgtcactg aattgactta cagagaagtt ttggaagaac gtcgtcgtga atccagaggt   3840

aaattcaaga aaactttcgt tttgaacaga cctcctccat tatggactga cggtgtcggt   3900

ttcatcgacc gtggtatctt gaccaaccac gttcaaccac catctgacaa cttattggtt   3960

gccatctgtg gtccaccagt tatgcaaaga attgtcaagg ccactttaaa gactttaggt   4020

tacaacatga acttggtcag aaccgttgac gaaactgaac catctggaag ttaaaggaag   4080

tatctcggaa atattaattt aggccatgtc cttatgcacg tttcttttga tacttacggg   4140

tacatgtaca caagtatatc tatatatata aattaatgaa aatcccctat ttatatatat   4200

gactttaacg agacagaaca gtttttttatt ttttatccta tttgatgaat gatacagttt   4260

cttattcacg tgttataccc acaccaaatc caatagcaat accggccatc acaatcactg   4320

tttcggcagc ccctaagatc agacaaaaca tccggaacca ccttaaatca acgtccctca   4380

gaaagcctgt atgcgaagcc acaatccttt ccaacagacc atactaagt               4429
```

```
<210> SEQ ID NO 9
<211> LENGTH: 20
<212> TYPE: DNA
<213> ORGANISM: Artificial sequence
<220> FEATURE:
<223> OTHER INFORMATION: primer

<400> SEQUENCE: 9

cattatatcg aggaaagccc                                            20
```

<210> SEQ ID NO 10
<211> LENGTH: 75
<212> TYPE: DNA
<213> ORGANISM: Artificial sequence
<220> FEATURE:
<223> OTHER INFORMATION: primer

<400> SEQUENCE: 10
aaagcaaagg aaggagagaa cagaggagta cttgtacgtt cgatgggcaa agaaagagac 60
acaaaactac gtggg 75

<210> SEQ ID NO 11
<211> LENGTH: 20
<212> TYPE: DNA
<213> ORGANISM: Artificial sequence
<220> FEATURE:
<223> OTHER INFORMATION: primer

<400> SEQUENCE: 11
ttgcccatcg aacgtacaag 20

<210> SEQ ID NO 12
<211> LENGTH: 23
<212> TYPE: DNA
<213> ORGANISM: Artificial sequence
<220> FEATURE:
<223> OTHER INFORMATION: primer

<400> SEQUENCE: 12
tgctaagatt tgtgttcgtt tgg 23

<210> SEQ ID NO 13
<211> LENGTH: 20
<212> TYPE: DNA
<213> ORGANISM: Artificial sequence
<220> FEATURE:
<223> OTHER INFORMATION: primer

<400> SEQUENCE: 13
cggatcgatg tacacaaccg 20

<210> SEQ ID NO 14
<211> LENGTH: 23
<212> TYPE: DNA
<213> ORGANISM: Artificial sequence
<220> FEATURE:
<223> OTHER INFORMATION: primer

<400> SEQUENCE: 14
caacaggagg cggatggata tac 23

<210> SEQ ID NO 15
<211> LENGTH: 79
<212> TYPE: DNA
<213> ORGANISM: Artificial sequence
<220> FEATURE:
<223> OTHER INFORMATION: primer

<400> SEQUENCE: 15
acgctttccg gcatcttcca gaccacagta tatccatccg cctcctgttg tcgtacgctg 60
caggtcgacg aattctacc 79

<210> SEQ ID NO 16
<211> LENGTH: 75
<212> TYPE: DNA

<213> ORGANISM: Artificial sequence
<220> FEATURE:
<223> OTHER INFORMATION: primer

<400> SEQUENCE: 16
gcggaatatt ggcggaacgg acacacgtgg atacaaacct ggacaacgtt taggccacta 60
gtggatctga tatcg 75

<210> SEQ ID NO 17
<211> LENGTH: 22
<212> TYPE: DNA
<213> ORGANISM: Artificial sequence
<220> FEATURE:
<223> OTHER INFORMATION: primer

<400> SEQUENCE: 17
aacgttgtcc aggtttgtat cc 22

<210> SEQ ID NO 18
<211> LENGTH: 20
<212> TYPE: DNA
<213> ORGANISM: Artificial sequence
<220> FEATURE:
<223> OTHER INFORMATION: primer

<400> SEQUENCE: 18
aggtacaaca agcacgaccg 20

<210> SEQ ID NO 19
<211> LENGTH: 23
<212> TYPE: DNA
<213> ORGANISM: Artificial sequence
<220> FEATURE:
<223> OTHER INFORMATION: primer

<400> SEQUENCE: 19
aaataaccac aaacatcctt ccc 23

<210> SEQ ID NO 20
<211> LENGTH: 23
<212> TYPE: DNA
<213> ORGANISM: Artificial sequence
<220> FEATURE:
<223> OTHER INFORMATION: primer

<400> SEQUENCE: 20
gtgcactaca tcttgtgggt gtc 23

<210> SEQ ID NO 21
<211> LENGTH: 22
<212> TYPE: DNA
<213> ORGANISM: Artificial sequence
<220> FEATURE:
<223> OTHER INFORMATION: primer

<400> SEQUENCE: 21
gaaaccttcg aatccagcca gc 22

<210> SEQ ID NO 22
<211> LENGTH: 20
<212> TYPE: DNA
<213> ORGANISM: Artificial sequence
<220> FEATURE:
<223> OTHER INFORMATION: primer

<400> SEQUENCE: 22

```
aatcgcaact cggatttggg                                                  20


<210> SEQ ID NO 23
<211> LENGTH: 73
<212> TYPE: DNA
<213> ORGANISM: Artificial sequence
<220> FEATURE:
<223> OTHER INFORMATION: primer

<400> SEQUENCE: 23

aaagccaaag ttcgcgttcc gaccttgcct cccaaatccg agttgcgatt tcttggcggc      60

cgtacgcata tag                                                         73


<210> SEQ ID NO 24
<211> LENGTH: 20
<212> TYPE: DNA
<213> ORGANISM: Artificial sequence
<220> FEATURE:
<223> OTHER INFORMATION: primer

<400> SEQUENCE: 24

cgcacaccac gaggtgaagg                                                  20


<210> SEQ ID NO 25
<211> LENGTH: 25
<212> TYPE: DNA
<213> ORGANISM: Artificial sequence
<220> FEATURE:
<223> OTHER INFORMATION: primer

<400> SEQUENCE: 25

cggcattatt gtgtatggct caata                                            25


<210> SEQ ID NO 26
<211> LENGTH: 75
<212> TYPE: DNA
<213> ORGANISM: Artificial sequence
<220> FEATURE:
<223> OTHER INFORMATION: primer

<400> SEQUENCE: 26

gaacttcgac ctgttgcaat acttcgggtt cggcacaaac gtgtacggat agggtttcaa      60

agatccatac ttctc                                                       75


<210> SEQ ID NO 27
<211> LENGTH: 79
<212> TYPE: DNA
<213> ORGANISM: Artificial sequence
<220> FEATURE:
<223> OTHER INFORMATION: primer

<400> SEQUENCE: 27

atccgtacac gtttgtgccg aacccgaagt attgcaacag gtcgaagttc tcgtacgctg      60

caggtcgacg aattctacc                                                   79


<210> SEQ ID NO 28
<211> LENGTH: 74
<212> TYPE: DNA
<213> ORGANISM: Artificial sequence
<220> FEATURE:
<223> OTHER INFORMATION: primer

<400> SEQUENCE: 28
```

aatcgcaact cggatttggg aggcaaggtc ggaacgcgaa ctttggcttt aggccactag 60
tggatctgat atcg 74

<210> SEQ ID NO 29
<211> LENGTH: 90
<212> TYPE: DNA
<213> ORGANISM: Artificial sequence
<220> FEATURE:
<223> OTHER INFORMATION: primer

<400> SEQUENCE: 29
agaaagcctg tatgcgaagc cacaatcctt tccaacagac catactaagt attttatttt 60 actttttta gaatgacctg ttcccgacac 90

<210> SEQ ID NO 30
<211> LENGTH: 24
<212> TYPE: DNA
<213> ORGANISM: Artificial sequence
<220> FEATURE:
<223> OTHER INFORMATION: primer

<400> SEQUENCE: 30
cacaagctta ttcttccaaa aatc 24

<210> SEQ ID NO 31
<211> LENGTH: 20
<212> TYPE: DNA
<213> ORGANISM: Artificial sequence
<220> FEATURE:
<223> OTHER INFORMATION: primer

<400> SEQUENCE: 31
aaagccaaag ttcgcgttcc 20

<210> SEQ ID NO 32
<211> LENGTH: 24
<212> TYPE: DNA
<213> ORGANISM: Artificial sequence
<220> FEATURE:
<223> OTHER INFORMATION: primer

<400> SEQUENCE: 32
acttagtatg gtctgttgga aagg 24

<210> SEQ ID NO 33
<211> LENGTH: 1139
<212> TYPE: PRT
<213> ORGANISM: Artificial sequence
<220> FEATURE:
<223> OTHER INFORMATION: FRDg protein sequence (minus C-terminal SKI)

<400> SEQUENCE: 33

```
Met Val Asp Gly Arg Ser Ser Ala Ser Ile Val Ala Val Asp Pro Glu
1               5                   10                  15

Arg Ala Ala Arg Glu Arg Asp Ala Ala Ala Arg Ala Leu Leu Gln Asp
            20                  25                  30

Ser Pro Leu His Thr Thr Met Gln Tyr Ala Thr Ser Gly Leu Glu Leu
        35                  40                  45

Thr Val Pro Tyr Ala Leu Lys Val Val Ala Ser Ala Asp Thr Phe Asp
    50                  55                  60

Arg Ala Lys Glu Val Ala Asp Glu Val Leu Arg Cys Ala Trp Gln Leu
65                  70                  75                  80
```

-continued

```
Ala Asp Thr Val Leu Asn Ser Phe Asn Pro Asn Ser Glu Val Ser Leu
                85                  90                  95

Val Gly Arg Leu Pro Val Gly Gln Lys His Gln Met Ser Ala Pro Leu
            100                 105                 110

Lys Arg Val Met Ala Cys Cys Gln Arg Val Tyr Asn Ser Ser Ala Gly
        115                 120                 125

Cys Phe Asp Pro Ser Thr Ala Pro Val Ala Lys Ala Leu Arg Glu Ile
    130                 135                 140

Ala Leu Gly Lys Glu Arg Asn Asn Ala Cys Leu Glu Ala Leu Thr Gln
145                 150                 155                 160

Ala Cys Thr Leu Pro Asn Ser Phe Val Ile Asp Phe Glu Ala Gly Thr
                165                 170                 175

Ile Ser Arg Lys His Glu His Ala Ser Leu Asp Leu Gly Gly Val Ser
            180                 185                 190

Lys Gly Tyr Ile Val Asp Tyr Val Ile Asp Asn Ile Asn Ala Ala Gly
        195                 200                 205

Phe Gln Asn Val Phe Phe Asp Trp Gly Gly Asp Cys Arg Ala Ser Gly
    210                 215                 220

Met Asn Ala Arg Asn Thr Pro Trp Val Val Gly Ile Thr Arg Pro Pro
225                 230                 235                 240

Ser Leu Asp Met Leu Pro Asn Pro Pro Lys Glu Ala Ser Tyr Ile Ser
                245                 250                 255

Val Ile Ser Leu Asp Asn Glu Ala Leu Ala Thr Ser Gly Asp Tyr Glu
            260                 265                 270

Asn Leu Ile Tyr Thr Ala Asp Asp Lys Pro Leu Thr Cys Thr Tyr Asp
        275                 280                 285

Trp Lys Gly Lys Glu Leu Met Lys Pro Ser Gln Ser Asn Ile Ala Gln
    290                 295                 300

Val Ser Val Lys Cys Tyr Ser Ala Met Tyr Ala Asp Ala Leu Ala Thr
305                 310                 315                 320

Ala Cys Phe Ile Lys Arg Asp Pro Ala Lys Val Arg Gln Leu Leu Asp
                325                 330                 335

Gly Trp Arg Tyr Val Arg Asp Thr Val Arg Asp Tyr Arg Val Tyr Val
            340                 345                 350

Arg Glu Asn Glu Arg Val Ala Lys Met Phe Glu Ile Ala Thr Glu Asp
        355                 360                 365

Ala Glu Met Arg Lys Arg Arg Ile Ser Asn Thr Leu Pro Ala Arg Val
    370                 375                 380

Ile Val Val Gly Gly Gly Leu Ala Gly Leu Ser Ala Ala Ile Glu Ala
385                 390                 395                 400

Ala Gly Cys Gly Ala Gln Val Val Leu Met Glu Lys Glu Ala Lys Leu
                405                 410                 415

Gly Gly Asn Ser Ala Lys Ala Thr Ser Gly Ile Asn Gly Trp Gly Thr
            420                 425                 430

Arg Ala Gln Ala Lys Ala Ser Ile Val Asp Gly Gly Lys Tyr Phe Glu
        435                 440                 445

Arg Asp Thr Tyr Lys Ser Gly Ile Gly Gly Asn Thr Asp Pro Ala Leu
    450                 455                 460

Val Lys Thr Leu Ser Met Lys Ser Ala Asp Ala Ile Gly Trp Leu Thr
465                 470                 475                 480

Ser Leu Gly Val Pro Leu Thr Val Leu Ser Gln Leu Gly Gly His Ser
                485                 490                 495

Arg Lys Arg Thr His Arg Ala Pro Asp Lys Lys Asp Gly Thr Pro Leu
```

```
            500                 505                 510

Pro Ile Gly Phe Thr Ile Met Lys Thr Leu Glu Asp His Val Arg Gly
        515                 520                 525

Asn Leu Ser Gly Arg Ile Thr Ile Met Glu Asn Cys Ser Val Thr Ser
    530                 535                 540

Leu Leu Ser Glu Thr Lys Glu Arg Pro Asp Gly Thr Lys Gln Ile Arg
545                 550                 555                 560

Val Thr Gly Val Glu Phe Thr Gln Ala Gly Ser Gly Lys Thr Thr Ile
                565                 570                 575

Leu Ala Asp Ala Val Ile Leu Ala Thr Gly Gly Phe Ser Asn Asp Lys
            580                 585                 590

Thr Ala Asp Ser Leu Leu Arg Glu His Ala Pro His Leu Val Asn Phe
        595                 600                 605

Pro Thr Thr Asn Gly Pro Trp Ala Thr Gly Asp Gly Val Lys Leu Ala
    610                 615                 620

Gln Arg Leu Gly Ala Gln Leu Val Asp Met Asp Lys Val Gln Leu His
625                 630                 635                 640

Pro Thr Gly Leu Ile Asn Pro Lys Asp Pro Ala Asn Pro Thr Lys Phe
                645                 650                 655

Leu Gly Pro Glu Ala Leu Arg Gly Ser Gly Gly Val Leu Leu Asn Lys
            660                 665                 670

Gln Gly Lys Arg Phe Val Asn Glu Leu Asp Leu Arg Ser Val Val Ser
        675                 680                 685

Lys Ala Ile Met Glu Gln Gly Ala Glu Tyr Pro Gly Ser Gly Gly Ser
    690                 695                 700

Met Phe Ala Tyr Cys Val Leu Asn Ala Ala Ala Gln Lys Leu Phe Gly
705                 710                 715                 720

Val Ser Ser His Glu Phe Tyr Trp Lys Lys Met Gly Leu Phe Val Lys
                725                 730                 735

Ala Asp Thr Met Arg Asp Leu Ala Ala Leu Ile Gly Cys Pro Val Glu
            740                 745                 750

Ser Val Gln Gln Thr Leu Glu Glu Tyr Glu Arg Leu Ser Ile Ser Gln
        755                 760                 765

Arg Ser Cys Pro Ile Thr Arg Lys Ser Val Tyr Pro Cys Val Leu Gly
    770                 775                 780

Thr Lys Gly Pro Tyr Tyr Val Ala Phe Val Thr Pro Ser Ile His Tyr
785                 790                 795                 800

Thr Met Gly Gly Cys Leu Ile Ser Pro Ser Ala Glu Ile Gln Met Lys
                805                 810                 815

Asn Thr Ser Ser Arg Ala Pro Leu Ser His Ser Asn Pro Ile Leu Gly
            820                 825                 830

Leu Phe Gly Ala Gly Glu Val Thr Gly Gly Val His Gly Gly Asn Arg
        835                 840                 845

Leu Gly Gly Asn Ser Leu Leu Glu Cys Val Val Phe Gly Arg Ile Ala
    850                 855                 860

Gly Asp Arg Ala Ser Thr Ile Leu Gln Arg Lys Ser Ser Ala Leu Ser
865                 870                 875                 880

Phe Lys Val Trp Thr Thr Val Val Leu Arg Glu Val Arg Glu Gly Gly
                885                 890                 895

Val Tyr Gly Ala Gly Ser Arg Val Leu Arg Phe Asn Leu Pro Gly Ala
            900                 905                 910

Leu Gln Arg Ser Gly Leu Ser Leu Gly Gln Phe Ile Ala Ile Arg Gly
        915                 920                 925
```

```
Asp Trp Asp Gly Gln Gln Leu Ile Gly Tyr Tyr Ser Pro Ile Thr Leu
    930                 935                 940

Pro Asp Asp Leu Gly Met Ile Asp Ile Leu Ala Arg Ser Asp Lys Gly
945                 950                 955                 960

Thr Leu Arg Glu Trp Ile Ser Ala Leu Glu Pro Gly Asp Ala Val Glu
                965                 970                 975

Met Lys Ala Cys Gly Gly Leu Val Ile Glu Arg Arg Leu Ser Asp Lys
            980                 985                 990

His Phe Val Phe Met Gly His Ile  Ile Asn Lys Leu Cys  Leu Ile Ala
        995                 1000                1005

Gly Gly  Thr Gly Val Ala Pro  Met Leu Gln Ile Ile  Lys Ala Ala
    1010                1015                1020

Phe Met  Lys Pro Phe Ile Asp  Thr Leu Glu Ser Val  His Leu Ile
    1025                1030                1035

Tyr Ala  Ala Glu Asp Val Thr  Glu Leu Thr Tyr Arg  Glu Val Leu
    1040                1045                1050

Glu Glu  Arg Arg Arg Glu Ser  Arg Gly Lys Phe Lys  Lys Thr Phe
    1055                1060                1065

Val Leu  Asn Arg Pro Pro Pro  Leu Trp Thr Asp Gly  Val Gly Phe
    1070                1075                1080

Ile Asp  Arg Gly Ile Leu Thr  Asn His Val Gln Pro  Pro Ser Asp
    1085                1090                1095

Asn Leu  Leu Val Ala Ile Cys  Gly Pro Pro Val Met  Gln Arg Ile
    1100                1105                1110

Val Lys  Ala Thr Leu Lys Thr  Leu Gly Tyr Asn Met  Asn Leu Val
    1115                1120                1125

Arg Thr  Val Asp Glu Thr Glu  Pro Ser Gly Ser
    1130                1135
```

```
<210> SEQ ID NO 34
<211> LENGTH: 30
<212> TYPE: DNA
<213> ORGANISM: Artificial sequence
<220> FEATURE:
<223> OTHER INFORMATION: Primer

<400> SEQUENCE: 34

ataaaaattg catatatgtg ggtagaaacc                                        30


<210> SEQ ID NO 35
<211> LENGTH: 78
<212> TYPE: DNA
<213> ORGANISM: Artificial sequence
<220> FEATURE:
<223> OTHER INFORMATION: Primer

<400> SEQUENCE: 35

tatagcatac attatacgaa cggtagaatt cgtcgacctg cagcgtacga tcaaagcaga      60

aatctgatgg gttcgaac                                                     78


<210> SEQ ID NO 36
<211> LENGTH: 75
<212> TYPE: DNA
<213> ORGANISM: Artificial sequence
<220> FEATURE:
<223> OTHER INFORMATION: Primer

<400> SEQUENCE: 36
```

agaaagcctg tatgcgaagc cacaatcctt tccaacagac catactaagt acaggtgatt 60
gtatgtgggc ttatg 75

<210> SEQ ID NO 37
<211> LENGTH: 29
<212> TYPE: DNA
<213> ORGANISM: Artificial sequence
<220> FEATURE:
<223> OTHER INFORMATION: Primer

<400> SEQUENCE: 37
acattattgt aaaaacggag tagaaaggg 29

<210> SEQ ID NO 38
<211> LENGTH: 595
<212> TYPE: DNA
<213> ORGANISM: Artificial sequence
<220> FEATURE:
<223> OTHER INFORMATION: PCR fragment 25, consisting of the 5' integration flank for targeting the INT09.01 locus of CEN.PK113-7D

<400> SEQUENCE: 38
gggaaggaac ataatccggt atgtgaaatc aattgaatct atcctctgtc tcggtataat 60
attatacaag ttaggagaat agttatatat aaatatatgt gaacttgtag aactgatggc 120
atttgatggc cgtcacatgg tacgccacta aaaccttgat taagtagatt agattagact 180
agcaagtgtt ggtaacgttt tgtaggaaag agtctcaaag tacccagcgc caacttttgc 240
taaagtcaat cataaaatat atgtttttaa aatatgtagg tatgccgtgc atttttattc 300
ttttttaatg tttagctttc aaaaaagcta aaataaacca taagcgttat tcttattata 360
ttgatagtag aagaggaaga gtggttatct ttactcaaat taacgattgc ttttatttct 420
tacattaagg tcgaaactat ttgctactat gaaagccaag cagaaacaaa caagacctta 480
ttaagattga tgtttcaagc tatgcattcc caattcagaa gaacaaggga agagcataag 540
acggctcctc ggatcggcca gttgggagca aggtggtact tctgtcgtcg tattt 595

<210> SEQ ID NO 39
<211> LENGTH: 1381
<212> TYPE: DNA
<213> ORGANISM: Artificial sequence
<220> FEATURE:
<223> OTHER INFORMATION: PCR fragment 26, which includes a nourseothricin selection marker functional in Saccharomyces cerevisiae.

<400> SEQUENCE: 39
tcctcggatc ggccagttgg gagcaaggtg gtacttctgt cgtcgtattt gtgctaccgt 60
tcgtataatg tatgctatac gaagttatgt ccccgccggg tcacccggcc agcgacatgg 120
aggcccagaa taccctcctt gacagtcttg acgtgcgcag ctcaggggca tgatgtgact 180
gtcgcccgta catttagccc atacatcccc atgtataatc atttgcatcc atacattttg 240
atggccgcac ggcgcgaagc aaaaattacg gctcctcgct gcagacctgc gagcagggaa 300
acgctcccct cacagacgcg ttgaattgtc cccacgccgc gcccctgtag agaaatataa 360
aaggttagga tttgccactg aggttcttct ttcatatact tccttttaaa atcttgctag 420
gatacagttc tcacatcaca tccgaacata aacaacaatg aatgggtacc actcttgacg 480
acacggctta ccggtaccgc accagtgtcc cgggggacgc cgaggccatc gaggcactgg 540
atgggtcctt caccaccgac accgtcttcc gcgtcaccgc caccggggac ggcttcaccc 600

```
tgcgggaggt gccggtggac ccgcccctga ccaaggtgtt ccccgacgac gaatcggacg    660

acgaatcgga cgacggggag gacggcgacc cggactcccg gacgttcgtc gcgtacgggg    720

acgacggcga cctggcgggc ttcgtggtcg tctcgtactc cggctggaac cgccggctga    780

ccgtcgagga catcgaggtc gccccggagc accgggggca cggggtcggg cgcgcgttga    840

tggggctcgc gacggagttc gcccgcgagc ggggcgccgg gcacctctgg ctggaggtca    900

ccaacgtcaa cgcaccggcg atccacgcgt accggcggat ggggttcacc ctctgcggcc    960

tggacaccgc cctgtacgac ggcaccgcct cggacggcga gcaggcgctc tacatgagca   1020

tgccctgccc ctaaataaat cagtactgac aataaaaaga ttcttgtttt caagaacttg   1080

tcatttgtat agttttttta tattgtagtt gttctatttt aatcaaatgt tagcgtgatt   1140

tatatttttt ttcgcctcga catcatctgc ccagatgcga agttaagtgc gcagaaagta   1200

atatcatgcg tcaatcgtat gtgaatgctg gtcgctatac tgctgtcgat tcgatactaa   1260

cgccgccatc cagtgtcgaa aacgagctca taacttcgta taatgtatgc tatacgaacg   1320

gtacctccct catttggaac agcaggcgag gtgtattggt gcgagaagag gtgtttccga   1380

g                                                                   1381
```

<210> SEQ ID NO 40
<211> LENGTH: 4838
<212> TYPE: DNA
<213> ORGANISM: Artificial sequence
<220> FEATURE:
<223> OTHER INFORMATION: PCR fragment 27 including coding sequence for fumarate reductase from Trypanosoma brucei (FRDg) codon pair optimized for expression in S. cerevisiae.

<400> SEQUENCE: 40

```
atttggaaca gcaggcgagg tgtattggtg cgagaagagg tgtttccgag gtgcgttcct     60

catcactaga agccgaactg ttgtcttcag tggggattgg ttcgacattt tgccaattgc    120

tgtcgatgta ccctttcaaa gccatgtacc ttaaatcttc atccttggca agtagattca    180

tcgggtgtgt ttgaagtaag aatatttgct tgtttttatg gtatcaaagg tatatgttgt    240

agaagacaat ttccggtaat ccaattgtct gtctgctcag tttagcacat gtatagtacg    300

ttgcacatag tctacaatat tcagcattca gcattcagta tacagcatat ggctaaatga    360

tcacaaatgt gattgatgat ttgacacgac tagaaaagag aacgaaaaag ggaaattcca    420

tgtcacgtgc gttggcacgt gacatggaat atcgaagaaa gaaaaaaaaa acgatctcgt    480

cctagtggaa gcccagagtc tggtccccc ggagtcttcc caaaacaaga agctgacaca    540

tgttgacaca gaacacccca cagcaaatgc accacgctac gtagatcagg aagcttaact    600

ctagcgacct gtcgctcgcc ccacagaacc tcacccgaga accacacatt acacgccgcc    660

agctcccact atactcatct tgcttccctt aagcgttctc acgattcgtt cgctgccctt    720

cttcaagagt cttctgattc taattctcat tcgaaatcct ctacagttaa tgaattgctt    780

gacatgacat tcattgtctc atggttttgg ctttttggct tttgtctttt aaagctatat    840

caactttaca tataaatata cgtcaaaagg ggattcatta attagaaaat tctctttttc    900

aatagttgct attcattatc aatctattca actcaattgg ttattatttt catctttttg    960

tcatcctaaa ccatcaacaa tatttaaata tatctgttgc tacattaaga gttacttcag   1020

aaataacaaa aaaatcgatc aagaattaat aaaaatgaat ggtcgacggt agatcctctg   1080

cttctatcgt cgctgtcgac ccagaaagag ccgctcgtga acgtgacgct gctgctcgtg   1140

ctttgctaca agattctcca ttgcacacta ccatgcaata tgctacttcc ggtttggaat   1200
```

```
taaccgtccc atacgccttg aaggttgtcg cttctgctga caccttcgat cgtgctaagg   1260
aagttgctga cgaagtttta agatgtgctt ggcaattagc cgacactgtt ttaaactctt   1320
ttaacccaaa ctccgaagtc tctttggttg gtagattgcc agttggtcaa aaacaccaaa   1380
tgtccgctcc attgaagaga gtcatggcct gttgtcaacg tgtttacaac tcttctgctg   1440
gttgcttcga tccatctact gctccagtcg ccaaagcttt gagagaaatc gctttaggta   1500
aggaacgtaa caacgcttgc ttggaagctt tgacccaagc ttgtactcta ccaaactctt   1560
tcgttatcga cttcgaagct ggcaccattt ctagaaagca cgaacatgct tctttggact   1620
tgggtggtgt ctctaagggt tacattgttg actacgttat cgacaacatc aacgctgccg   1680
gtttccaaaa cgtcttcttc gactggggtg gcgactgtag agcttctggt atgaacgcta   1740
gaaacacccc atgggttgtt ggtattacca gaccaccatc tttggacatg ctaccaaacc   1800
caccaaagga agcttcctac atctctgtta tttctttgga caacgaagct ttggccactt   1860
ccggtgacta cgaaaacttg atttacaccg ctgatgacaa gccattgact tgtacttacg   1920
actggaaggg taaggaatta atgaagccat ctcagtccaa cattgctcaa gtctctgtta   1980
agtgttactc cgctatgtac gctgatgctt tagccactgc ttgtttcatt aagagagatc   2040
cagctaaggt tcgtcaattg ttggacggtt ggagatacgt ccgtgatact gttcgtgact   2100
acagagttta cgttcgtgaa aacgaaagag tcgctaagat gtttgaaatc gctaccgaag   2160
acgctgaaat gagaaagcgt agaatctcta acactttgcc agctagagtt attgtcgtcg   2220
gtggtggttt ggccggtttg tccgccgcta tcgaagctgc cggttgtggt gctcaggtcg   2280
tcttgatgga aaaagaagct aagttgggtg gtaacagcgc taaggctact tctggtatta   2340
acggttgggg caccagagcc caagccaaag cctctatcgt cgacggtggt aaatacttcg   2400
aacgtgacac ttacaagtct ggtattggtg gtaacactga cccagctttg gtcaagacct   2460
tgtccatgaa gtctgctgat gccatcggtt ggttaacctc cttgggtgtc ccattaaccg   2520
ttttgtctca attgggtggt cactctagaa agagaaccca ccgtgctcca gacaagaaag   2580
atggtactcc attaccaatc ggtttcacta tcatgaagac tttggaagac cacgttcgtg   2640
gtaacttgtc tggtcgtatc actatcatgg aaaactgtag cgtcacctct ctattatctg   2700
aaaccaagga acgtccagat ggtactaaac aaatccgtgt cactggtgtt gaatttaccc   2760
aagctggttc cggtaagact actatcttgg ctgatgctgt cattttggct actggtggtt   2820
tcagtaatga caagaccgct gactccttgt tgagagaaca cgctccacac ttggtcaact   2880
tcccaactac caacggccca tgggctaccg gtgacggtgt taagttggcc caaagattgg   2940
gtgctcaatt ggttgacatg gataaggttc aattgcatcc aactggtttg attaacccaa   3000
aggatccagc taacccaacc aagttcttgg gtccagaggc cttgagaggt tccggtggtg   3060
tcttgttgaa caagcaaggt aagagattcg tcaacgaatt agatctaaga tccgttgttt   3120
ccaaggctat catggagcaa ggtgccgaat acccaggttc cggtggttcc atgttcgctt   3180
actgtgtttt gaacgctgcc gctcaaaagt tattcggtgt ctcttctcat gaattctatt   3240
ggaagaagat gggtctattt gttaaggctg ataccatgag agatctagct gctttgatcg   3300
gctgtccagt tgaatctgtc caacaaacct tggaagaata cgaacgtttg tctatttctc   3360
aacgttcttg tccaatcacc cgtaagtctg tctacccatg tgtcttaggg accaagggtc   3420
catactacgt tgctttcgtc accccatcta ttcactacac tatgggcggt tgtttgatct   3480
ccccatccgc cgaaattcaa atgaaaaaca cttcctctcg tgctccattg tctcactcta   3540
```

```
atccaatctt gggtttgttc ggtgctggcg aagttaccgg tggtgttcat ggtggtaacc   3600
gtttgggtgg taactccttg ttggagtgtg ttgtcttcgg tagaatcgct ggtgacagag   3660
cctccaccat cttgcaacgt aagtcttctg ccttgtcctt caaggtttgg actaccgttg   3720
tcttgagaga agttagagaa ggtggcgtct acggtgccgg ttctagagtt ttgagattca   3780
acttgcctgg tgctttgcaa cgttccggtt tgtctttagg tcaattcatc gctatcagag   3840
gtgattggga cggtcaacaa ctaattggtt actactcccc aattactttg ccagatgact   3900
tgggtatgat cgatatctta gctcgttctg acaaaggtac tttgagagaa tggatttctg   3960
ctttggaacc tggtgatgct gttgaaatga aggcctgtgg tggtttggtt attgaaagaa   4020
gattgtccga caagcacttc gtcttcatgg gtcacatcat caacaaattg tgtttgattg   4080
ccggtggtac tggtgtcgcc ccaatgttgc aaattatcaa ggctgctttc atgaagcctt   4140
tcatcgatac cttggaatct gttcacttga tttacgctgc tgaggatgtt accgaattga   4200
cctacagaga agtcttggaa gaaagaagaa gagaatccag aggtaagttc aagaagactt   4260
ttgtcttaaa cagaccacca ccattgtgga ccgacggtgt tggtttcatc gatagaggta   4320
tcttgactaa ccacgttcaa cctccatccg acaacttgtt ggtcgctatc tgtggtcctc   4380
cagtcatgca aagaattgtt aaggctactt tgaaaacctt gggttacaat atgaacttgg   4440
ttagaactgt tgatgaaacc gaaccttccg gttaaataaa gcgaatttct tatgatttat   4500
gatttttatt attaaataag ttataaaaaa aataagtgta tacaaatttt aaagtgactc   4560
ttaggtttta aaacgaaaat tcttattctt gagtaactct ttcctgtagg tcaggttgct   4620
ttctcaggta tagcatgagg tcgctcttat tgaccacacc tctaccggca tgccgagcaa   4680
atgcctgcaa atcgctcccc atttcaccca attgtagata tgctaactcc agcaatgagt   4740
tgatgaatct cggtgtgtat tttatgtcct cagaggacaa cctccctctt tccttgtacc   4800
aaagaacgag tatataccca ggtatccaga gcgcttgt                           4838
```

<210> SEQ ID NO 41
<211> LENGTH: 586
<212> TYPE: DNA
<213> ORGANISM: Artificial sequence
<220> FEATURE:
<223> OTHER INFORMATION: PCR fragment 28 consisting of the 3' integration flank for targeting the INT09.01 locus of CEN.PK113-7D

<400> SEQUENCE: 41

```
tttccttgta ccaaagaacg agtatatacc caggtatcca gagcgcttgt atctgcattt     60
aacagtagtg gtcactccta cagtagtcat acttctcaag cctactttcg gtatggcttt    120
taaagtcata aaataacgaa tagttcgtat accgctcatg tggcaaactc aatagcaaaa    180
tgtgatttca tatcacgaag ttttttatat tttttaatta tacaattgta atttgtatta    240
cggaaatgaa acatgtttgt atgttatgta gtatatcaat aattgattta ccgcatctgt    300
aaaagagaac catttatcac gcacatagtt ttagtattca ctaatcggtg ctctatggaa    360
gtacgagaca ccgtgcatag atggaagggg aaggtaataa gcttctctct aagaattttc    420
tttgtaaacc ctttcgactt ctgatttaac agcggctaag atttctcttc tctttaattt    480
ttgagcagat gtgacaaagc cattttcagg tgtccattct tcatcaaaga aaacaatacc    540
acataatagt tcaataccaa ccaaaccttg agatttggct gttgcg                   586
```

FUMARATE REDUCTASES

CROSS REFERENCE TO RELATED APPLICATIONS

This application is a §371 National Stage Application of PCT/EP2014/077638, filed 12 Dec. 2014, which claims priority to EP13196950.3, filed 12 Dec. 2013.

FIELD OF THE INVENTION

The present invention relates to a variant polypeptide having fumarate reductase activity. The invention also relates to a nucleic acid comprising sequence encoding such a variant polypeptide, to a nucleic acid construct comprising such a nucleic acid, to a recombinant expression vector comprising such a nucleic acid or nucleic acid construct and a recombinant host cell comprising such a nucleic acid, nucleic acid construct or expression vector. The invention further relates to a method for producing a variant polypeptide having fumarate reductase activity and to a method for the production of a dicarboxylic acid.

BACKGROUND TO THE INVENTION

Succinic acid is a potential precursor for numerous chemicals. For example, succinic acid can be converted into 1,4-butanediol (BDO), tetrahydrofuran, and gamma-butyrolactone. Another product derived from succinic acid is a polyester polymer which is made by linking succinic acid and BDO.

Succinic acid is predominantly produced through petrochemical processes by hydrogenation of butane. These processes are considered harmful for the environment and costly. The fermentative production of succinic acid may be an attractive alternative process for the production of succinic acid, wherein a renewable feedstock as carbon source may be used.

A number of different bacteria such as *Escherichia coli*, and the rumen bacteria *Actinobacillus, Anaerobiospirillum, Bacteroides, Mannheimia*, or *Succinimonas*, sp. are known to produce succinic acid. Metabolic engineering of these bacterial strains have improved the succinic acid yield and/or productivity, or reduced the by-product formation.

WO2007/061590 discloses a pyruvate decarboxylase negative yeast for the production of malic acid and/or succinic acid which is transformed with a pyruvate carboxylase enzyme or a phosphoenolpyruvate carboxylase, a malate dehydrogenase enzyme, and a malic acid transporter protein (MAE).

Despite the improvements that have been made in the fermentative production of succinic acid, there remains a need for improved microorganisms for the fermentative production of succinic acid.

WO2009/065778 discloses that increased levels of succinic acid production may be achieved with a recombinant eukaryotic cell selected from the group consisting of a yeast and a filamentous fungus comprising a nucleotide sequence encoding NAD(H)-dependent fumarate reductase that catalyses the conversion of fumaric acid to succinic acid. It was found that the recombinant eukaryotic cell produces an increased amount of succinic acid compared to the amount of succinic acid produced by a eukaryotic cell which does not comprise the nucleotide sequence encoding NAD(H)-dependent fumarate reductase.

Nevertheless, it would be desirable to achieve even higher levels of succinic acid production in a fermentative process.

SUMMARY OF THE INVENTION

The invention relates to variant polypeptides having fumarate reductase (FRD) activity, i.e. to fumarate reductase variants. A fumarate reductase variant of the invention may have one or more modified, for example improved, properties in comparison with a reference polypeptide, the reference polypeptide typically having fumarate reductase activity, in particular with regard to NADP(H)- and/or NAD(H)-dependent activity. That ratio of NADP(H)-:NAD(H)-dependent activity may be modified in comparison with a reference polypeptide.

A reference polypeptide may be a wild-type fumarate reductase, such as a wild-type fumarate reductase from a protozoan source, such as *Trypanosoma brucei, Trypanosoma cruzi, Leishmania braziliensis*, or *Leishmania Mexicana*. The reference polypeptide may be a fumarate reductase (NADH) EC1.3.1.6.

Variant polypeptides of the invention may be referred to as a "fumarate reductase (FRD) variant", an "improved fumarate reductase (FRD)" and the like.

According to the invention, there is thus provided a variant polypeptide having fumarate reductase activity, which has modified NADP(H)-dependent activity and/or modified NAD(H)-dependent activity as compared with a reference polypeptide having fumarate reductase activity. Such a variant polypeptide is capable of catalysing conversion of fumaric acid to succinic acid.

A variant polypeptide may be expressed in a host cell such that it catalyses the conversion of fumaric acid to succinic acid. Such a host cell produces an increased amount of a dicarboxylic acid, such as succinic acid, compared to the amount of succinic acid produced by a cell expressing a reference polypeptide.

A variant polypeptide having fumarate reductase activity, which variant polypeptide has an amino acid sequence which, when aligned with the fumarate reductase comprising the sequence set out in SEQ ID NO: 33, comprises at least one substitution of an amino acid residue corresponding to any of amino acids 1042, 1071, 1072, 1082 or 1083 said positions being defined with reference to SEQ ID NO: 33 and wherein the variant has one or more modified properties as compared with a reference polypeptide having fumarate reductase activity.

The invention also provides:

- a nucleic acid comprising sequence encoding a variant polypeptide according to any one of the preceding claims;
- a nucleic acid construct comprising a nucleic acid of the invention operably linked to one or more control sequences capable of directing the expression of a fumarate reductase in a suitable expression host;
- a expression vector comprising a nucleic acid or nucleic acid construct of the invention;
- a host cell comprising a nucleic acid, nucleic acid construct or an expression vector of the invention;
- a method for producing a fumarate reductase comprising cultivating a host cell of the invention under conditions suitable for production of the fumarate reductase and, optionally, recovering the fumarate reductase;
- a method for the production of a dicarboxylic acid, such as succinic acid, which method comprises fermenting a host cell of the invention under conditions suitable for production of the dicarboxylic acid, such as succinic acid, and, optionally, recovering the dicaboxylic acid, such as succinic acid.

BRIEF DESCRIPTION OF THE DRAWINGS

FIG. 3 shows NADH and NADPH dependent fumarate reductase (FRD) activity of FCC variants. Shown is the slope of the change in absorbance at 340 nm $min^1$, which is a measure for the fumarate reductase activity. Equal amounts of soluble extracts were used to test the NADH and NADPH dependent activity of each variant, so that the effect of the mutation on cofactor specificity can be determined for each variant. Clear is that for the FCC variants that contained beneficial mutations for increased succinic acid production (variants in graph below) all exhibited significantly altered cofactor specificity when compared to the reference (wild type protein minus C-terminal SKI). In all cases the NADH-dependent FRD activity is significantly reduced compared to the reference, in the majority of cases more than threefold. Surprisingly, for a large number of the FCC variants the NADPH specificity is increased by 50-100% compared to the reference, indicating that we have produced fumarate reductase variants that exhibit significant dependence on NADPH besides NADH (for the reference there is no significant NADPH dependent activity compared to NADH activity). The dotted line represents the background NADPH activity of the reference FRDg.

FIG. 5 shows NADH and NADPH dependent fumarate reductase (FRD) activity of FCC variants expressed in strain SUC-723. Shown is the normalized activity, determined as the change in absorbance at 340 nm ($min^{-1}$) divided by total protein concentration (mg $mL^{-1}$) of the soluble cell extract, which is a measure for the fumarate reductase activity. Equal amounts of soluble extracts were used to test the NADH and NADPH dependent activity of each variant, so that the effect of the mutation on cofactor specificity can be determined for each variant. Clear is that for the FCC variants that contained beneficial mutations for increased succinic acid production (variants in graph below) all exhibited significantly altered cofactor specificity when compared to the reference (wild type FRD protein minus C-terminal SKI). This is evidenced by the fact that in all cases the NADH-dependent FRD activity is significantly reduced compared to the reference, a reduction between seven- and sixteen fold. For variant FCC-034 the NADPH specificity is increased compared to the reference, indicating that we have produced a fumarate reductase variant in strain SUC-723 that exhibits significant NADPH dependence besides accepting NADH. FCC_040 has completely switched cofactor specificity, preferring NADPH over NADH, as evidenced by its higher activity with NADPH compared to it activity with NADH. Surprisingly, altering the NAD(P)H cofactor specificity of fumarate reductase (FIG. 5) has a beneficial effect on the succinic acid production of strain SUC-723 (Table 4).

DESCRIPTION OF THE SEQUENCE LISTING

Figure 1:
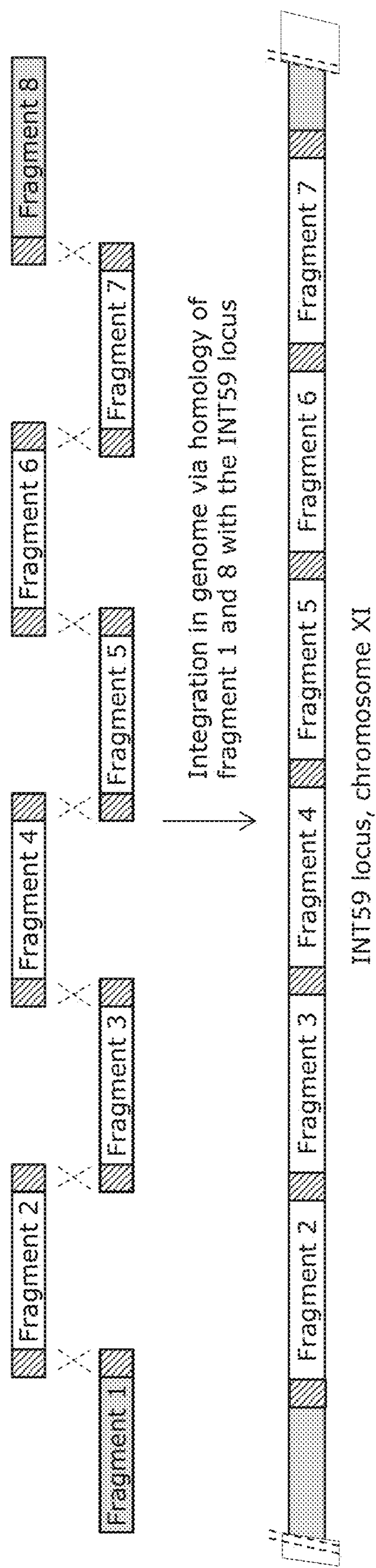
FIG. 1 sets out a schematic depiction of integration of fragments 1-8. The striped parts indicated in fragments 1-8 denote the unique homologous overlap regions leading to the recombination events as indicated by the dashed crosses between the homologous regions. Fragment 1 and fragment 8 are homologous to the INT59 locus on chromosome XI, homologous recombination results in integration of fragment 1-8 into the INT59 locus.

SEQ ID NO: 1 sets out the nucleotide sequence of fragment 2 (FIG. 1), which includes PEP carboxykinase from *Actinobacillus succinogenes* codon pair optimized for expression in *Saccharomyces cerevisiae.*

SEQ ID NO: 2 sets out the nucleotide sequence of fragment 3 (FIG. 1), which includes pyruvate carboxylase (PYC2) from *S. cerevisiae* codon pair optimized for expression in *S. cerevisiae.*

SEQ ID NO: 3 sets out the nucleotide sequence of fragment 4 (FIG. 1), which includes a KanMX selection marker functional in *S. cerevisiae.*

SEQ ID NO: 4 sets out the nucleotide sequence of fragment 5 (FIG. 1), which includes a putative dicarboxylic acid transporter from *A. niger* codon pair optimized for expression in *S. cerevisiae.*

SEQ ID NO: 5 sets out the nucleotide sequence of fragment 6 (FIG. 1), which includes malate dehydrogenase (MDH3) from *S. cerevisiae* codon pair optimized for expression in *S. cerevisiae.*

SEQ ID NO: 6 sets out the nucleotide sequence of fragment 7 (FIG. 1), which includes fumarase (fumB) from *Escherichia coli* codon pair optimized for expression in *S. cerevisiae.*

SEQ ID NO: 7 sets out the nucleotide sequence of fragment 10 (FIG. 2), which includes a nourseothricin selection marker functional in *Saccharomyces cerevisiae.*

SEQ ID NO: 8 sets out the nucleotide sequence of fragment 11 (FIG. 2), which includes coding sequence for fumarate reductase from *Trypanosoma brucei* (FRDg) codon pair optimized for expression in *S. cerevisiae.*

SEQ ID NO: 9 sets out the nucleotide sequence of the primer used to generate fragment 1 (FIG. 1).

SEQ ID NO: 10 sets out the nucleotide sequence of the primer used to generate fragment 1 (FIG. 1).

SEQ ID NO: 11 sets out the nucleotide sequence of the primer used to generate fragment 2 (FIG. 1).

SEQ ID NO: 12 sets out the nucleotide sequence of the primer used to generate fragment 2 (FIG. 1).

SEQ ID NO: 13 sets out the nucleotide sequence of the primer used to generate fragment 3 (FIG. 1).

SEQ ID NO: 14 sets out the nucleotide sequence of the primer used to generate fragment 3 (FIG. 1).

SEQ ID NO: 15 sets out the nucleotide sequence of the primer used to generate fragment 4 (FIG. 1).

SEQ ID NO: 16 sets out the nucleotide sequence of the primer used to generate fragment 4 (FIG. 1).

SEQ ID NO: 17 sets out the nucleotide sequence of the primer used to generate fragment 5 (FIG. 1).

SEQ ID NO: 18 sets out the nucleotide sequence of the primer used to generate fragment 5 (FIG. 1).

SEQ ID NO: 19 sets out the nucleotide sequence of the primer used to generate fragment 6 (FIG. 1).

SEQ ID NO: 20 sets out the nucleotide sequence of the primer used to generate fragment 6 (FIG. 1).

SEQ ID NO: 21 sets out the nucleotide sequence of the primer used to generate fragment 7 (FIG. 1).

SEQ ID NO: 22 sets out the nucleotide sequence of the primer used to generate fragment 7 (FIG. 1).

SEQ ID NO: 23 sets out the nucleotide sequence of the primer used to generate fragment 8 (FIG. 1).

SEQ ID NO: 24 sets out the nucleotide sequence of the primer used to generate fragment 8 (FIG. 1).

Figure 2:
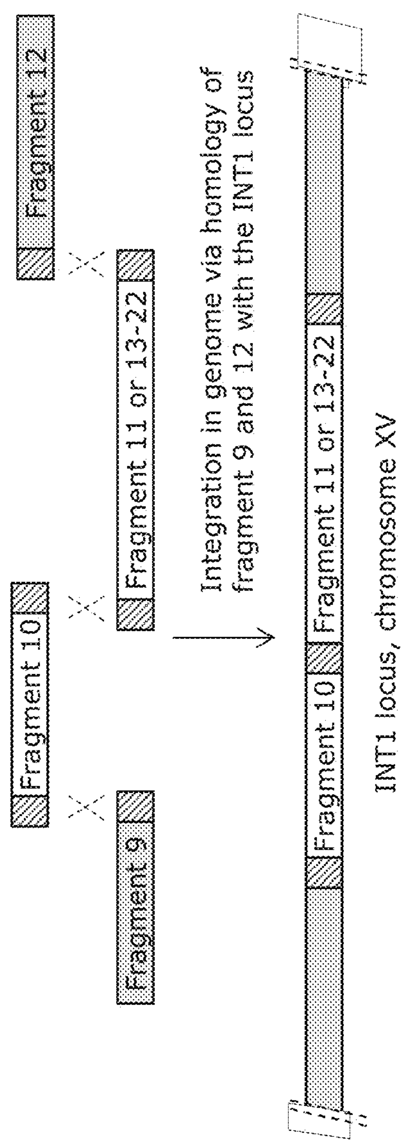
FIG. 2 sets out a schematic depiction of integration of fragments 9-12. The striped parts indicated in fragments 9-12 denote the unique homologous overlap regions leading to the recombination events as indicated by the dashed crosses between the homologous regions. Fragment 9 and fragment 12 are homologous to the INT1 locus on chromosome XV, homologous recombination results in integration of fragment 9-12 into the INT1 locus. Fragment 11 can be replaced by fragment 13-22, which contain the same homology regions as fragment 11.

SEQ ID NO: 25 sets out the nucleotide sequence of the primer used to generate fragment 9 (FIG. 2).

SEQ ID NO: 26 sets out the nucleotide sequence of the primer used to generate fragment 9 (FIG. 2).

SEQ ID NO: 27 sets out the nucleotide sequence of the primer used to generate fragment 10 (FIG. 2).

SEQ ID NO: 28 sets out the nucleotide sequence of the primer used to generate fragment 10 (FIG. 2).

SEQ ID NO: 29 sets out the nucleotide sequence of the primer used to generate fragment 12 (FIG. 2).

SEQ ID NO: 30 sets out the nucleotide sequence of the primer used to generate fragment 12 (FIG. 2).

SEQ ID NO: 31 sets out the nucleotide sequence of the primer used to generate fragment 11 (FRDg reference) or fragments 13-22 (FRD variants) (FIG. 2).

SEQ ID NO: 32 sets out the nucleotide sequence of the primer used to generate fragment 11 (FRDg reference) or fragments 13-22 (FRD variants) (FIG. 2).

SEQ ID NO: 33 sets out the amino acid sequence of the fumarate reductase protein from *T. brucei* without the C-terminal SKI sequence (FRDg reference).

SEQ ID NO: 34 sets out the nucleotide sequence of the primer used to generate fragment 23.

SEQ ID NO: 35 sets out the nucleotide sequence of the primer used to generate fragment 23.

SEQ ID NO: 36 sets out the nucleotide sequence of the primer used to generate fragment 24

SEQ ID NO: 37 sets out the nucleotide sequence of the primer used to generate fragment 24.

SEQ ID NO: 38 sets out the nucleotide sequence of PCR fragment 25, consisting of the 5' integration flank for targeting the INT09.01 locus of CEN.PK113-7D SEQ ID NO: 39 sets out the nucleotide sequence of PCR fragment 26, which includes a nourseothricin selection marker functional in *Saccharomyces cerevisiae.*

SEQ ID NO: 40 sets out the nucleotide sequence of PCR fragment 27, which includes coding sequence for fumarate reductase from *Trypanosoma brucei* (FRDg) codon pair optimized for expression in *S. cerevisiae.*

SEQ ID NO: 41 sets out the nucleotide sequence of PCR fragment 28, consisting of the 3' integration flank for targeting the INT09.01 locus of CEN.PK113-7D

DETAILED DESCRIPTION OF A PREFERRED EMBODIMENT

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and an are used herein to refer to one or to more than one (i.e. to one or at least one) of the grammatical object of the article. By way of example, "an element" may mean one element or more than one element.

The reductive TCA pathway contains two reactions that require consumption of reducing power (e.g. NADH or NADPH): the malate dehydrogenase reaction (reduction of oxaloacetate to malate) and the fumarate reductase reaction (reduction of fumarate to succinate).

*Saccharomyces cerevisiae* has two endogenous fumarate reductases FRD1 and OSM1. They are located in both cytosol and mitochondria, and have also been detected in plasma membrane fractions. They both use FADH2 as cofactor. However, there is no known cytosolic FADH2 source. Unlike FADH2, nicotinamide-containing cofactors such as NADH and NADPH can be regenerated by, for example, glyceraldehyde 3-phosphate dehydrogenase (NADH) in glycolysis or the oxidative branch of the pentose phosphate pathway (NADPH).

Accordingly, introducing a fumarate reductase that uses a nicotinamide-containing cofactor may be beneficial for fermentative production of a dicarboxylic acid such as succinic acid.

Currently, the only known class of fumarate reductase using a nicotinamide-containing cofactor are those from *Trypanosoma* and *Leishmania* species, such as the fumarate reductase gene of *Trypanosoma brucei* and its homologues. Combining this FRD and the yeast MDH into yeast cytosol thus results in a reductive TCA pathway that uses NADH as cofactor.

Changing the cofactor used in the reductive TCA pathway from NADH to NADPH can have several benefits including:

1. stronger thermodynamic driving force due to higher intracellular concentration ratio of $\frac{[NADPH]}{[NADH]}$ compared to $\frac{[NADH]}{[NAD]}$.
2. higher substrate concentration based on measurements of metabolite concentrations ([NADPH]×[NADH]).
3. cofactor regeneration uncoupled with glycolysis; and
4. additional cofactor regeneration via other pathways such as pentose phosphate pathway.

According to the invention, there is thus provided a variant polypeptide having fumarate reductase (FRD) activity. A variant polypeptide of the invention has fumarate reductase activity. Fumarate reductase activity is the activity converting fumaric acid to succinic acid:

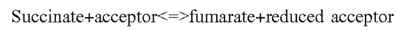

Succinate+acceptor<=>fumarate+reduced acceptor

A variant polypeptide of the invention has modified NAD(H)-dependent activity as compared with a reference polypeptide having FRD activity.

Such a variant polypeptide may have decreased NAD(H)-dependent activity as compared with the reference polypeptide.

Such a variant polypeptide may have increased NADP (H)-dependent activity as compared with the reference polypeptide.

The invention also provides a variant polypeptide having FRD activity which has modified NADP(H)-dependent activity as compared with a reference polypeptide having FRD activity.

Such a variant polypeptide may have increased NADP (H)-dependent activity as compared with the reference polypeptide.

Such a variant polypeptide may have decreased NAD(H)-dependent activity as compared with the reference polypeptide.

A reference polypeptide may be a wild-type fumarate reductase, such as a wild-type fumarate reductase from a protozoan source, such as *Trypanosoma brucei, Trypanosoma cruzi, Leishmania braziliensis*, or *Leishmania Mexicana*. The reference polypeptide may be a fumarate reductase (NADH) EC1.3.1.6. A FRD having the amino acid sequence set out in SEQ ID NO: 33 may be a suitable reference polypeptide.

A variant polypeptide according to the invention may be a non-naturally occurring polypeptide and/or may be encoded by a non-naturally occurring polynucleotide sequence.

The term "NADPH-dependent" herein typically refers to the property of an enzyme to preferentially use NADPH, rather than NADH, as the redox cofactor. Thus, an NADPH-dependent enzyme typically has a higher activity, for example a higher specificity constant ($k_{cat}/K_M$), with the cofactor NADPH than with the cofactor NADH, for example as determined by an enzyme activity assay such as are described in the Examples.

The term "NADH-dependent" herein typically refers to the property of an enzyme to preferentially use NADH, rather than NADPH, as the redox cofactor. Thus, an NADH-dependent enzyme typically has a higher activity, for example a higher specificity constant ($k_{cat}/K_M$), with the cofactor NADH than with the cofactor NADPH, for example as determined by an enzyme activity assay such as are described in the Examples.

Activity of a variant polypeptide of the invention may be determined as set out in Example 4. $V_{max}$ and $K_M$ of the enzymes to NADH and NADPH may be determined from the v0 using a Lineweaver-Burk plot (Lineweaver, H and Burk, D. (1934), "The Determination of Enzyme Dissociation Constants". Journal of the American Chemical Society 56 (3): 658-666) where the concentration of NADH or NADPH is varied from, for example, 25 to 400 μM.

A variant polypeptide of the invention may show an increase in NADP(H)-relative to NAD(H)-activity in comparison to a reference polypeptide. That is to say a variant polypeptide may show a decrease in the ration of NADP(H)- to NAD(H)-activity in comparison to a reference polypeptide Herein, variant polypeptides of the invention may be referred to as an "FRD variant", "FRD variant polypeptide", "variant", "variant polypeptide" or "FCC" or "FCC polypeptide" or the like.

A FRD variant polypeptide of the invention (for example a variant having one or more substitution as set out in herein) may have at least about 60%, 70%, 80% identity with the reference FRD polypeptide, such as the FRD of SEQ ID NO: 33, for example at least about 85% identity with the reference polypeptide, such as least about 90% identity with the reference polypeptide, at least about 95% identity with the reference polypeptide, at least about 98% identity with the reference polypeptide or at least about 99% identity with the reference polypeptide. Such a variant will typically have one or more substitution or sets of substitutions as set out in any one of Tables 1 2, 4, 5 or 6.

A FRD variant of the invention will typically retain FRD activity. That is to say, a FRD variant of the invention will typically bFe capable of catalysing the reaction set out above, albeit with a modified co-factor specificity as compared with a reference polypeptide.

Preferably, a FRD variant polypeptide of the invention will typically exhibit improved properties in comparison with the reference polypeptide from which it is derived, typically in terms of modified co-factor specificity. Such an improved property will typically be one which is relevant if the variant were to be used as set out below, for example in a method for the production of a dicarboxylic acid (by expressing the FRD).

Thus, a FRD variant of the invention is one which is typically capable of increasing production of a dicarboxylic acid in a recombinant microorganism capable of the production of a said dicarboxylic acid. That is to say, overexpression of a FRD variant polypeptide of the invention in a host cell will typically lead to increased production of a dicarboxylic acid as compared to a host cell which overexpresses the host polypeptide (such as the FRDg of SEQ ID NO: 33).

A FRD variant which exhibits a property which is improved in relation to the reference FRD is one which demonstrates a measurable reduction or increase in the relevant property, i.e. NAD(H)- or NADP(H)-dependent activity, typically such that the FRD variant is more suited to use as set out below, for example in a method for the production of a dicarboxylic acid.

A FRD variant polypeptide comprises an amino acid sequence that has one or more substitution, deletion and/or insertion of an amino acid as compared to the reference polypeptide and/or one or more truncations as compared to the reference polypeptide. A FRD variant polypeptide may comprise one or more of the substitutions described herein.

A variant polypeptide having FRD activity, for example as set out above, which variant polypeptide has an amino acid sequence which, when aligned with the fumarate comprising the sequence set out in SEQ ID NO: 33, comprises at least one substitution of an amino acid residue corresponding to any of amino acids 1042, 1071, 1072, 1082 or 1083 said positions being defined with reference to SEQ ID NO: 33 and wherein the variant has one or more modified properties as compared with a reference polypeptide having fumarate reductase activity.

Thus, the amino acid present at one or more of the said positions will be replaced with a different amino acid than appears at that position in the reference sequence (the positions being defined with reference to SEQ ID NO: 33).

The substitution at position 1042 (as defined with reference to SEQ ID NO: 33) will typically be to a polar amino acid, for example a non-negatively charged amino acid, such as a positively charged amino acid. Suitable positively charged amino acids include arginine (R), lysine (K) and histidine (H). A further suitable polar amino acid is glutamine (Q).

The substitution at position 1071 (as defined with reference to SEQ ID NO: 33) will typically be to a small amino acid. Suitable small amino acids include threonine (T), serine (S), glycine (G), alanine (A), proline (P) and aspartate (D).

The substitution at position 1082 (as defined with reference to SEQ ID NO: 33) will typically be to a positively charged amino acid. Suitable positively charged amino acids include arginine (R), lysine (K) and histidine (H).

The substitution at position 1083 (as defined with reference to SEQ ID NO: 33) will typically be to a smaller hydrophobic residue. Suitable smaller amino acids include isoleucine (I) or alanine (A).

The various types of amino acids above are classified with reference to, for example, Betts and Russell, In Bioinformatics for Geneticists, Barnes and Gray eds, Wiley 2003.

In more detail, a variant polypeptide may comprise:

R, K or Q at position 1042 as defined with reference to SEQ ID NO: 33;

T or S at position 1071 as defined with reference to SEQ ID NO: 33;

K at position 1072 as defined with reference to SEQ ID NO: 33;

K or R at position 1082 as defined with reference to SEQ ID NO: 33; or

Y, I or A at position 1083 as defined with reference to SEQ ID NO: 33;

Such a variant polypeptide may be modified so that the modified property is modified NAD(H)-dependent activity, such as decreased NAD(H)-dependent activity, and/or modified NADP(H)-dependent activity, such as increased NADP (H)-dependent activity.

A variant polypeptide according to any one of the preceding claims which comprises additional substitutions other than the five positions defined above, for example, one or more additional substitutions, additions or deletions.

A variant of the invention may comprise a combination of different types of modification of this sort. A variant may comprise one, two, three, four, least 5, at least 10, at least 15, at least 20, at least 25, at least 30 or more such modifications (which may all be of the same type or may be different types of modification). Typically, the additional modifications may be substitutions.

A variant polypeptide according to any one of the preceding claims as defined with reference to Table 1, 2, 4, 5 or 6. That is to say, a variant polypeptide may comprise any combination of substitutions as set out in Table 1, 2, 4, 5 or 6 as compared to a suitable reference sequence such as that set out in SEQ ID NO: 33.

Typically, then a variant polypeptide may comprise the sequence of SEQ ID NO: 33, but at one or more of positions 1042, 1071, 1072, 1082 or 1083 a different amino acid will be present at that position than is present in SEQ ID NO: 33 (i.e. the variant polypeptide comprises a substitution at one or more of positions 1042, 1071, 1072 or 1083). That is to say, the variant polypeptide may have an amino acid other than glutamate at position 1042 and/or an amino acid other than asparagine at position 1071 and/or an amino acid other than arginine at position 1072 and/or an amino acid other than glycine at position 1082 and/or an amino acid other than phenylalanine at position 1083.

TABLE 1

Mutated fumarate reductase, which contains mutations as compared to the reference sequence (SEQ ID NO: 33) in the amino acid positions indicated below. These sequences can be useful further increase succinic acid titers compared to using the reference sequence (SEQ ID NO: 33).

| | Mutation in position | | | | |
|---|---|---|---|---|---|
| Clone | 1042 | 1071 | 1072 | 1082 | 1083 |
| Reference | E | N | R | G | F |
| FCC_001 | E | S | R | G | F |
| FCC_002 | E | S | R | G | Y |
| FCC_003 | E | S | R | K | F |
| FCC_004 | E | S | R | K | Y |
| FCC_005 | E | S | R | R | F |
| FCC_006 | E | S | R | R | Y |
| FCC_007 | E | S | K | G | F |
| FCC_008 | E | S | K | G | Y |
| FCC_009 | E | S | K | K | F |
| FCC_010 | E | S | K | K | Y |
| FCC_011 | E | S | K | R | F |
| FCC_012 | E | S | K | R | Y |
| FCC_013 | E | T | R | G | F |
| FCC_014 | E | T | R | G | Y |
| FCC_015 | E | T | R | K | F |
| FCC_016 | E | T | R | K | Y |
| FCC_017 | E | T | R | R | F |
| FCC_018 | E | T | R | R | Y |
| FCC_019 | E | T | K | G | F |
| FCC_020 | E | T | K | G | Y |
| FCC_021 | E | T | K | K | F |
| FCC_022 | E | T | K | K | Y |
| FCC_023 | E | T | K | R | F |
| FCC_024 | E | T | K | R | Y |
| FCC_025 | R | S | R | G | F |
| FCC_026 | R | S | R | G | Y |
| FCC_027 | R | S | R | K | F |
| FCC_028 | R | S | R | K | Y |
| FCC_029 | R | S | R | R | F |
| FCC_030 | R | S | R | R | Y |
| FCC_031 | R | S | K | G | F |
| FCC_032 | R | S | K | G | Y |
| FCC_033 | R | S | K | K | F |
| FCC_034 | R | S | K | K | Y |
| FCC_035 | R | S | K | R | F |
| FCC_036 | R | S | K | R | Y |

TABLE 1-continued

Mutated fumarate reductase, which contains mutations as compared to the reference sequence (SEQ ID NO: 33) in the amino acid positions indicated below. These sequences can be useful further increase succinic acid titers compared to using the reference sequence (SEQ ID NO: 33).

| | Mutation in position | | | | |
|---|---|---|---|---|---|
| Clone | 1042 | 1071 | 1072 | 1082 | 1083 |
| FCC_037 | R | T | R | G | F |
| FCC_038 | R | T | R | G | Y |
| FCC_039 | R | T | R | K | F |
| FCC_041 | R | T | R | R | F |
| FCC_042 | R | T | R | R | Y |
| FCC_043 | R | T | K | G | F |
| FCC_044 | R | T | K | G | Y |
| FCC_047 | R | T | K | R | F |
| FCC_049 | K | S | R | G | F |
| FCC_050 | K | S | R | G | Y |
| FCC_051 | K | S | R | K | F |
| FCC_052 | K | S | R | K | Y |
| FCC_053 | K | S | R | R | F |
| FCC_054 | K | S | R | R | Y |
| FCC_055 | K | S | K | G | F |
| FCC_056 | K | S | K | G | Y |
| FCC_057 | K | S | K | K | F |
| FCC_058 | K | S | K | K | Y |
| FCC_059 | K | S | K | R | F |
| FCC_060 | K | S | K | R | Y |
| FCC_061 | K | T | R | G | F |
| FCC_062 | K | T | R | G | Y |
| FCC_063 | K | T | R | K | F |
| FCC_064 | K | T | R | K | Y |
| FCC_066 | K | T | R | R | Y |
| FCC_067 | K | T | K | G | F |
| FCC_068 | K | T | K | G | Y |
| FCC_071 | K | T | K | R | F |
| FCC_072 | K | T | K | R | Y |
| FCC_073 | Q | S | R | G | F |
| FCC_074 | Q | S | R | G | Y |
| FCC_077 | Q | S | R | R | F |
| FCC_079 | Q | S | K | G | F |
| FCC_080 | Q | S | K | G | Y |
| FCC_081 | Q | S | K | K | F |
| FCC_082 | Q | S | K | K | Y |
| FCC_083 | Q | S | K | R | F |
| FCC_084 | Q | S | K | R | Y |
| FCC_085 | Q | T | R | G | F |
| FCC_086 | Q | T | R | G | Y |
| FCC_087 | Q | T | R | K | F |
| FCC_088 | Q | T | R | K | Y |
| FCC_089 | Q | T | R | R | F |
| FCC_090 | Q | T | R | R | Y |
| FCC_091 | Q | T | K | G | F |
| FCC_092 | Q | T | K | G | Y |
| FCC_093 | Q | T | K | K | F |
| FCC_094 | Q | T | K | K | Y |
| FCC_095 | Q | T | K | R | F |
| FCC_096 | Q | T | K | R | Y |
| FCC_097 | R | G | R | R | Y |
| FCC_098 | Q | G | R | R | Y |
| FCC_099 | R | G | R | K | Y |
| FCC_100 | Q | G | R | K | Y |
| FCC_101 | R | S | R | R | I |
| FCC_102 | R | G | R | R | I |
| FCC_103 | Q | S | R | R | I |
| FCC_104 | Q | G | R | R | I |
| FCC_105 | R | S | R | K | I |
| FCC_106 | R | G | R | K | I |
| FCC_107 | Q | S | R | K | I |
| FCC_108 | Q | G | R | K | I |
| FCC_109 | R | S | R | R | A |
| FCC_110 | R | G | R | R | A |
| FCC_111 | Q | S | R | R | A |
| FCC_112 | Q | G | R | R | A |
| FCC_113 | R | S | R | K | A |
| FCC_114 | R | G | R | K | A |
| FCC_115 | Q | S | R | K | A |
| FCC_116 | Q | G | R | K | A |
| FCC_117 | R | S | R | R | S |
| FCC_118 | R | G | R | R | S |
| FCC_119 | Q | S | R | R | S |
| FCC_120 | Q | G | R | R | S |
| FCC_121 | R | S | R | K | S |
| FCC_122 | R | G | R | K | S |
| FCC_123 | Q | S | R | K | S |
| FCC_124 | Q | G | R | K | S |

A variant polypeptide will typically have modified FRD activity in comparison to a reference polypeptide. Typically, the modified activity may be defined in terms of modified co-factor dependence. This NAD(H)- or NADP(H)-dependent activity may be modified, for example decreased (in the case of NAD(H)-dependent activity), by at least 10%, at least 20%, at least 30%, at least 40% at least 50%, at least 60%, at least 70%, at least 80%, at least 90%, at least 95% or at least 99%. Alternatively, the property may be increased (in the case of NAHP(H)-dependent activity) by at least 10%, at least 25%, at least 50%, at least 100%, at least, 200%, at least 500% or at least 1000%.

The percentage decrease or increase in this context represents the percentage decrease or increase in comparison to the reference FRD polypeptide, for example that of SEQ ID NO: 33. It is well known to the skilled person how such percentage changes may be measured—it is a comparison of the activity, for example NAD(H)- or NADP(H)-dependent activity, of the reference FRD and the variant FRD measured as set out in the Example or according to, for example, Miura A. et al, *J. Bacteriol* 190:7170-717.

The modified activity may be defined in terms of an increase in the production of a dicarboxylic acid when a variant FRD is overexpressed in a host cell as compared to the production level of an equivalent host cell which overexpresses a reference polypeptide, for example that of SEQ ID NO: 33. A variant FRD may be capable of increasing production levels by at least 5%, at least 10%, at least 25%, at least 50%, at least 100% or more. Production level may be expressed in terms of g/L, so an increase in the production level of a dicarboxylic acid will be evident by higher level of production in terms of g/L.

The word "polypeptide" is used herein for chains containing more than about seven amino acid residues. All polypeptide sequences herein are written from left to right and in the direction from amino terminus to carboxy terminus. The one-letter code of amino acids used herein is commonly known in the art and can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989).

A FRD variant polypeptide of the invention may be in isolated form, such as substantially isolated form. By "isolated" polypeptide or protein is intended a polypeptide or protein removed from its native environment. For example, recombinantly produced polypeptides and proteins expressed in host cells are considered isolated for the purpose of the invention as are recombinant polypeptides which have been substantially purified by any suitable technique. A FRD variant polypeptide according to the invention can be recovered and purified from recombinant cell cultures by methods known in the art.

FRD variant polypeptides of the present invention include products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The invention also features biologically active fragments of the FRD polypeptide variants according to the invention. Such fragments are considered to be encompassed within the term "a FRD variant of the invention".

Biologically active fragments of a FRD polypeptide variant of the invention include polypeptides comprising amino acid sequences sufficiently identical to or derived from the amino acid sequence of a variant protein of the invention which include fewer amino acids than the full length protein but which exhibit at least one biological activity of the corresponding full-length protein. Typically, biologically active fragments comprise a domain or motif with at least one activity of a variant protein of the invention. A biologically active fragment of a FRD variant of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

Typically, a protein fragment of a FRD variant of the invention will comprise one or more of the substitutions defined herein.

The invention also features nucleic acid fragments which encode the above biologically active fragments (which biologically active fragments are themselves variants of the invention).

Preferably, a FRD variant of the invention lacks a peroxisomal or mitochondrial targeting signal for cytosolic activity of the enzyme upon expression of the encoding nucleotide sequence in a suitable host cell.

The present invention provides polynucleotides which comprise sequence encoding a FRD variant polypeptide of the invention (and biologically active fragments thereof). The invention also relates to an isolated polynucleotide encoding at least one functional domain of a FRD polypeptide variant of the invention. Typically, such a domain will comprise one or more of the substitutions described herein.

A nucleic acid molecule of the present invention can be generated using standard molecular biology techniques well known to those skilled in the art taken in combination with the sequence information provided herein. For example, using standard synthetic techniques, the required nucleic acid molecule may be generated by PCR or synthesized de novo. Such a synthetic process will typically be an automated process.

A nucleic acid of the invention may comprise one or more deletions, i.e. gaps, in comparison to a nucleic acid encoding a reference FRD. Such deletions/gaps may also be generated using site-directed mutagenesis using appropriate oligonucleotides. Techniques for generating such deletions are well known to those skilled in the art.

Furthermore, oligonucleotides corresponding to or hybridizable to nucleotide sequences according to the invention can be prepared by standard synthetic techniques, e.g., using an automated DNA synthesizer.

Also, complementary nucleic acids and antisense nucleic acids are included in the present invention. A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a variant polypeptide of the invention, or a biologically active fragment or domain thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules, such as for the preparation of nucleic acid molecules of the invention.

An "isolated nucleic acid" or "isolated polynucleotide" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "nucleic acid", "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The invention also relates to a nucleic acid construct comprising a nucleic acid sequence encoding a variant polypeptide of the invention and, linked operably thereto, control sequences permitting expression of the nucleic acid sequence in a host cell. The nucleic acid construct may be incorporated into a vector, such as an expression vector and/or into a host cell in order to effect expression of the variant polypeptide.

The term "nucleic acid construct" is herein referred to as a nucleic acid molecule, either single- or double-stranded, which is isolated from a naturally-occurring gene or, more typically, which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

A promoter that could be used to achieve the expression of a nucleotide sequence coding for an enzyme such as NAD(H)-dependent fumarate reductase or any other enzyme introduced in the eukaryotic cell of the invention, may be not native to a nucleotide sequence coding for the enzyme to be expressed, i.e. a promoter that is heterologous to the nucleotide sequence (coding sequence) to which it is operably linked. Preferably, the promoter is homologous, i.e. endogenous to the host cell.

Suitable promoters in this context include both constitutive and inducible natural promoters as well as engineered promoters, which are well known to the person skilled in the art. Suitable promoters in eukaryotic host cells may be GAL7, GAL10, or GAL 1, CYC1, HIS3, ADH1, PGL, PH05, GAPDH, ADC1, TRP1, URA3, LEU2, ENO, TPI, and AOX1. Other suitable promoters include PDC, GPD1, PGK1, TEF1, and TDH.

Usually a nucleotide sequence encoding an enzyme comprises a terminator. Any terminator, which is functional in the eukaryotic cell, may be used in the present invention. Preferred terminators are obtained from natural genes of the host cell. Suitable terminator sequences are well known in the art. Preferably, such terminators are combined with mutations that prevent nonsense mediated mRNA decay in the host cell of the invention (see for example: Shirley et al., 2002, Genetics 161:1465-1482).

The invention further relates to a vector, preferably an expression vector, comprising a nucleic acid or a nucleic acid construct of the invention of the invention (i.e. comprising sequence encoding a variant FRD polypeptide of the invention).

In order to facilitate expression and/or translation of the ISP, the nucleic acid sequence encoding the ISP may be comprised in an expression vector such that the gene encoding the ISP is operably linked to the appropriate control sequences for expression and/or translation in vitro, or in a host cell of the invention. That is to say, the invention provides an expression vector comprising a nucleic acid or nucleic acid construct of the invention.

The expression vector may be any vector (e.g., a plasmid or virus), which can be conveniently subjected to recombinant DNA procedures and can bring about the expression of the polynucleotide encoding the FRD variant polypeptide. The choice of the vector will typically depend on the compatibility of the vector with the cell into which the vector is to be introduced. The vectors may be linear or closed circular plasmids. The vector may be an autonomously replicating vector, i. e., a vector, which exists as an extra-chromosomal entity, the replication of which is independent of chromosomal replication, e.g., a plasmid, an extra-chromosomal element, a mini-chromosome, or an artificial chromosome. If intended for use in a host cell of fungal origin, a suitable episomal nucleic acid construct may e.g. be based on the yeast 2μ or pKD1 plasmids (Gleer et al., 1991, Biotechnology 9: 968-975), or the AMA plasmids (Fierro et al., 1995, Curr Genet. 29:482-489).

Alternatively, the expression vector may be one which, when introduced into the host cell, is integrated into the genome and replicated together with the chromosome(s) into which it has been integrated. The integrative cloning vector may integrate at random or at a predetermined target locus in the chromosomes of the host cell. In a preferred embodiment of the invention, the integrative cloning vector comprises a DNA fragment, which is homologous to a DNA sequence in a predetermined target locus in the genome of host cell for targeting the integration of the cloning vector to this predetermined locus. In order to promote targeted integration, the cloning vector is preferably linearized prior to transformation of the cell. Linearization is preferably performed such that at least one but preferably either end of the cloning vector is flanked by sequences homologous to the target locus. The length of the homologous sequences flanking the target locus is preferably at least 20 bp, at least 30 bp, at least 50 bp, at least 0.1 kb, at least 0.2 kb, at least 0.5 kb, at least 1 kb, at least 2 kb or longer. The efficiency of targeted integration into the genome of the host cell, i.e. integration in a predetermined target locus, is increased by augmented homologous recombination abilities of the host cell.

The homologous flanking DNA sequences in the cloning vector, which are homologous to the target locus, are derived from a highly expressed locus meaning that they are derived from a gene, which is capable of high expression level in the host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l.

A nucleic acid construct or expression vector may be assembled in vivo in a host cell of the invention and, optionally, integrated into the genome of the cell in a single step (see, for example, WO2013/076280)

More than one copy of a nucleic acid construct or expression vector of the invention may be inserted into a filamentous fungus host cell to increase production of the FRD variant polypeptide (over-expression) encoded by the nucleic acid sequence comprised within the nucleic acid construct. This can be done, preferably by integrating into its genome two or more copies of the nucleic acid, more preferably by targeting the integration of the nucleic acid at a highly expressed locus defined as defined above.

It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g. a FRD variant of SEQ ID NO: 33, for example a functional equivalent or fragment, or a fusion protein comprising one or more of such variants).

The nucleic acid constructs and vectors of the invention can be designed for expression of FRD variant polypeptides of the invention in a prokaryotic host cell or eukaryotic host cell.

A nucleic acid construct and/or expression vector of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell well known to those skilled in the art. Suitable methods for transforming or transfecting host cells can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989), Davis et al., Basic Methods in Molecular Biology (1986) and other laboratory manuals.

The terms "functional equivalents" and "functional variants" are used interchangeably herein. Functional equivalents according to the invention are isolated nucleic acid fragments that encode a polypeptide that exhibits a particular function of a FRD variant as defined herein. Functional equivalents therefore also encompass biologically active fragments and are themselves encompassed within the term "a FRD variant" of the invention.

Preferably, a functional equivalent of the invention comprises one or more of the substitutions described herein. However, a functional equivalent may comprise one or more modifications in addition to the substitutions described above.

Functional nucleic acid equivalents may typically contain silent mutations or mutations that do not alter the biological function of the encoded FRD variant polypeptide. Accordingly, the invention provides nucleic acid molecules encoding a variant FRD protein that contains changes in amino acid residues that are not essential for a particular biological activity, i.e. FRD activity.

Such functional equivalents of FRD variant proteins differ in amino acid sequence from the parent FRD variant sequence from which they are derived yet retain at least one biological activity thereof, preferably they retain at least FRD activity. The skilled person will recognise that changes can be introduced by mutation into the nucleotide sequences according to the invention thereby leading to changes in the amino acid sequence of the resulting protein without substantially altering the function of such a protein.

In one embodiment the isolated nucleic acid molecule comprises a nucleotide sequence encoding a protein, wherein the protein comprises an amino acid sequence having at least about 60%, 65%, 70%, 75%, 80%, 85%, 90%, 95%, 96%, 97%, 98%, 99% identity with the parent FRD variant or to the reference amino acid sequence (for example that shown in SEQ ID NO: 33).

Accordingly, a functional equivalent of a FRD variant of the invention is preferably a protein which comprises an amino acid sequence having at least about 60%, 65%, 70%, 75%, 80%, 85%, 90%, 95%, 96%, 97%, 98%, 99% or more identity to the parent FRD variant amino acid sequence or reference polypeptide sequence, for example that shown in SEQ ID NO: 33, and typically also retains at least one functional activity of the parent FRD polypeptide.

Variant FRD polypeptides of the invention may be identified e.g. by screening libraries of mutants, e.g. substitution mutants, of a suitable reference polypeptide. Candidate mutants may be screened on the basis of their ability to increase dicarboxylic acid production, such as succinic acid production, when expressed in a host cell (in comparison with a corresponding host cell expressing the reference polypeptide).

Fragments of a nucleic acid according to the invention may comprise or consist or sequences not encoding functional polypeptides. Such nucleic acids may function as probes or primers for a PCR reaction.

Nucleic acids according to the invention irrespective of whether they encode functional or non-functional polypeptides can be used as hybridization probes or polymerase chain reaction (PCR) primers. Uses of the nucleic acid molecules of the present invention that do not encode a polypeptide having FRD activity include, inter alia, (1) in situ hybridization (e.g. FISH) to metaphase chromosomal spreads to provide precise chromosomal location of an FRD-encoding gene as described in Verma et al., Human Chromosomes: a Manual of Basic Techniques, Pergamon Press, New York (1988); (2) Northern blot analysis for detecting expression of FRD mRNA in specific tissues and/or cells; and (3) probes and primers that can be used as a diagnostic tool to analyse the presence of a nucleic acid hybridizable to such a probe or primer in a given biological (e.g. tissue) sample.

Variants of a given reference FRD enzyme can be obtained by the following standard procedure:

- Mutagenesis (error-prone, doped oligo, spiked oligo) or synthesis of variants
- Transformation in, for example, *S. cerevisiae*
- Cultivation of transformants, selection of transformants
- Expression in, for example, *S. cerevisiae*
- Primary Screening, for example on the basis of dicarboxylic acid production
- Identification of an improved variant (for example in relation to altered co-factor specificity)

In one embodiment the invention relates to a method of producing a FRD polypeptide variant according to the invention, which method comprises:

a) selecting a reference FRD polypeptide;

b) substituting at least one amino acid residue corresponding to any of 1042, 1071, 1072, 1082 or 1083 said positions being defined with reference to SEQ ID NO: 33;

c) optionally substituting one or more further amino acids as defined in b);

d) preparing the variant resulting from steps a)-c);

e) determining a property of the variant, for example as set out in the Examples; and f) selecting a variant an altered property in comparison to the reference FRD polypeptide.

In a preferred embodiment in the method of producing a FRD polypeptide variant according to the invention, the reference FRD polypeptide has the sequence set out in SEQ ID NO: 33.

More preferably in step b) of the method according to the invention at least one amino acid residue corresponding to any of 1042, 1071, 1072, 1082 or 1083 is substituted, said positions being defined with reference to SEQ ID NO: 33.

The reference polypeptide may have at least about 80% homology with SEQ ID NO: 33.

In another embodiment, the invention features host cells, e.g., transformed host cells or recombinant host cells, that contain a nucleic acid, nucleic acid construct or vector of the invention. A "host cell" or "recombinant cell" according to the invention is typically a cell into which (or into an ancestor of which) has been introduced, by means of recombinant DNA techniques, a nucleic acid according to the invention, i.e. a nucleic acid encoding a FRD of the invention. In the context of the present invention a "host cell" according to the invention or a parent of said host cell may be any type of host cell.

A host cell according to any one of the preceding claims wherein the host cell is a eukaryotic or a prokaryotic cell. Accordingly, both prokaryotic and eukaryotic cells are included, e.g., bacteria, fungi, yeast, and the like, especially preferred are cells from yeasts, for example, *S. cerevisiae K. lactis*. Host cells also include, but are not limited to, mammalian cell lines such as CHO, VERO, BHK, HeLa, COS, MDCK, 293, 3T3, WI38, and choroid plexus cell lines.

The invention thus provides a method for producing a FRD, which method comprises cultivating a host cell as described herein under conditions suitable for production of the FRD and, optionally, recovering the FRD. Typically the host cell is capable of producing a dicarboxylic acid, such as succinic acid.

The host cell may be a prokaryotic cell. Preferably, the prokaryotic host cell is bacterial cell. The term "bacterial cell" includes both Gram-negative and Gram-positive microorganisms. Suitable bacteria may, for instance belong to *Mannheimia*, such as *M. succiniciproducens*, *Actinobacillus*, such as *A. succinogenes*, *Anaerobiospirillum*, *Bacteroides*, *Succinimonas*, *Escherichia*, such as *E. coli*.

A host cell according to the invention may be a eukaryotic host cell. Preferably, the eukaryotic cell is a mammalian, insect, plant, fungal, or algal cell. More preferably, the eukaryotic cell is a fungal cell. A suitable fungal cell may for instance belong to genera *Saccharomyces, Aspergillus, Penicillium, Pichia, Kluyveromyces, Yarrowia, Candida, Hansenula, Humicola, Issatchenkia, Torulaspora, Trichosporon, Brettanomyces, Rhizopus, Zygosaccharomyces, Pachysolen* or *Yamadazyma*. A fungal cell may for instance belong to a species of *Saccharomyces cerevisiae, Saccharomyces uvarum, Saccharomyces bayanus, Aspergillus niger, Penicillium chrysogenum, Pichia stipidis, Kluyveromyces marxianus, K. lactis, K. thermotolerans, Yarrowia lipolytica, Candida sonorensis, Candida kruisei, C. glabrata, Hansenula polymorpha, Issatchenkia orientalis, Torulaspora delbrueckii, Brettanomyces bruxellensis, Rhizopus oryzae* or *Zygosaccharomyces bailii*. In one embodiment a fungal cell in the process of the present invention is a yeast, for instance belonging to a *Saccharomyces* sp., such as a *Saccharomyces cerevisiae*.

Examples of specific host yeast cells include *C. sonorensis, K. marxianus, K. thermotolerans, C. methanesorbosa, Saccharomyces bulderi* (*S. bulderi*), *I. orientalis, C. lambica, C. sorboxylosa, C. zemplinina, C. geochares, P. membranifaciens, Z. kombuchaensis, C. sorbosivorans, C. vanderwaltii, C. sorbophila, Z. bisporus, Z. lentus, Saccharomyces bayanus* (*S. bayanus*), *D. castellii, C, boidinii, C. etchellsii, K. lactis, P. jadinii, P. anomala, Saccharomyces cerevisiae* (*S. cerevisiae*), *Pichia galeiformis, Pichia* sp. YB-4149 (NRRL designation), *Candida ethanolica, P. deserticola, P. membranifaciens, P. fermentans* and *Saccharomycopsis crataegensis* (*S. crataegensis*). Suitable strains of *K. marxianus* and *C. sonorensis* include those described in WO 00/71738 A1, WO 02/42471 A2, WO 03/049525 A2, WO 03/102152 A2 and WO 03/102201A2. Suitable strains of *I. orientalis* are ATCC strain 32196 and ATCC strain PTA-6648. In the invention, the host cell may be a Crabtree negative as a wild-type strain. The Crabtree effect is defined as the occurrence of fermentative metabolism under aerobic conditions due to the inhibition of oxygen consumption by a microorganism when cultured at high specific growth rates (long-term effect) or in the presence of high concentrations of glucose (short-term effect). Crabtree negative phenotypes do not exhibit this effect, and are thus able to consume oxygen even in the presence of high concentrations of glucose or at high growth rates.

In addition to a nucleic acid encoding a FRD variant polypeptide of the invention, a host cell of the invention may overexpress a nucleotide sequence comprising sequence encoding one or more of a pyruvate carboxylase, a phosphoenolpyruvate carboxykinase, a malate dehydrogenase, a fumarase, an isocitrate lyase, a malate synthase and a dicarboxylic acid transporter. Preferably, where one or more such enzymes are overexpressed they are active in the cytosol.

Thus, a host cell of the invention may overexpress a suitable homologous or heterologous nucleotide sequence that encodes a endogenous and/or heterologous enzyme that catalyzes a reaction in the cell resulting in an increased flux towards a dicarboxylic acid such malic acid, fumaric acid and/or succinic acid.

A host cell of the invention may overexpress an endogenous or heterologous nucleic acid sequence as described herein below.

A host cell may overexpress a pyruvate carboxylase (PYC) that catalyzes the reaction from pyruvate to oxaloacetate (EC 6.4.1.1). The pyruvate carboxylase may for instance be active in the cytosol upon expression of the gene. The host cell may overexpresses an endogenous or heterologous pyruvate carboxylase is overexpressed.

Preferably a host cell of the invention expresses a nucleotide sequence encoding a phosphoenolpyruvate (PEP) carboxykinase in the cytosol. Preferably a nucleotide sequence encoding a phosphoenolpyruvate (PEP) carboxykinase is overexpressed. The PEP carboxykinase (EC 4.1.1.49) preferably is a heterologous enzyme, preferably derived from bacteria, more preferably the enzyme having PEP carboxykinase activity is derived from *Escherichia coli, Mannheimia* sp., *Actinobacillus* sp., or *Anaerobiospirillum* sp., more preferably *Mannheimia succiniciproducens*. A gene encoding a PEP carboxykinase may be overexpressed and may be expressed and active in the cytosol of a fungal cell. Preferably, a yeast cell according to the present invention is genetically modified with a PEP carboxykinase which has at least 80, 85, 90, 95, 99 or 100% sequence identity with amino acid sequence encoded by the nucleic acid sequence of SEQ ID NO: 1.

In another embodiment, the host cell of the invention overexpresses a pyruvate carboxylase (PYC), that catalyses the reaction from pyruvate to oxaloacetate (EC 6.4.1.1). Preferably the pyruvate carboxylase is active in the cytosol upon expression of the gene. Preferably, an endogenous or homologous pyruvate carboxylase is overexpressed. Preferably, a host cell according to the present invention is genetically modified with a pyruvate carboxylase which has at least 80, 85, 90, 95, 99 or 100% sequence identity with amino acid sequence encoded by the nucleic acid sequence of SEQ ID NO: 2.

In one embodiment a host cell is modified with a nucleic acid comprising sequence encoding a malate dehydrogenase (MDH) active in the cytosol upon expression of the nucleic acid. Cytosolic expression may be obtained by deletion of a peroxisomal targeting signal. The malate dehydrogenase may be overexpressed. A cytosolic MDH may be any suitable homologous or heterologous malate dehydrogenase, catalyzing the reaction from oxaloacetate to malate (EC 1.1.1.37), for instance derived from *S. cerevisiae.*

Preferably, the MDH is *S. cerevisiae* MDH3, more preferably one which has a C-terminal SKL deletion such that it is active in the cytosol. Preferably, a host cell according to the present invention comprises a nucleotide sequence encoding a malate dehydrogenase that has at least 70%, preferably at least 75, 80, 85, 90, 92, 94, 95, 96, 97, 98, 99% or 100% sequence identity with the amino acid sequence encoded by the nucleic acid sequence of SEQ ID NO: 4.

In another embodiment a host cell of the present disclosure is modified with a gene encoding a fumarase, that catalyses the reaction from malic acid to fumaric acid (EC 4.2.1.2). A nucleic acid comprising sequence encoding a fumarase may be derived from any suitable origin, preferably from microbial origin, for instance a yeast such as *Saccharomyces* or a filamentous fungus, such *Rhizopus oryzae*, or a bacterium such a *Escherichia coli*. A host cell of the present invention may overexpress a nucleotide sequence encoding a fumarase. The fumarase may be active in the cytosol upon expression of the nucleotide sequence, for instance by deleting a peroxisomal targeting signal.

Preferably, a host cell of the present invention overexpresses a nucleotide sequence encoding a fumarase that has at least 70%, preferably at least 75, 80, 85, 90, 92, 94, 95, 96, 97, 98, or 99% or 100% sequence identity with the amino acid sequence encoded by the nucleic acid sequence of SEQ ID NO: 6.

A host cell according to the invention may express a nucleotide sequence encoding a dicarboxylic acid transporter protein, preferably a malic acid transporter protein (MAE) in the cytosol. Preferably the dicarboxylic acid transporter protein is overexpressed. A dicarboxylic acid transporter protein may be any suitable homologous or heterologous protein. Preferably, the dicarboxylic acid transporter protein is a heterologous protein. A dicarboxylic acid transporter protein may be derived from any suitable organism, preferably from yeast or fungi such as *Schizosaccharomyces pombe* or *Aspergillus niger*. Preferably, a dicarboxylic acid transporter protein is a malic acid transporter protein (MAE) which has at least 80, 85, 90, 95 or 99% or 100% sequence identity with the amino acid encoded by the nucleic acid sequence of SEQ ID NO: 5.

A host cell of the invention may overexpress a nucleic acid comprising sequence encoding an isocitrate lyase (EC 4.1.3.1), which may be any suitable heterologous or homologous enzyme. The isocitrate lyase may for instance be obtained from *Kluyveromyces lactis* or *Escherichia coli.*

A genetically modified fungal cell may further overexpress a nucleic acid comprising sequence encoding a malate synthase (EC 2.3.3.9). The malate synthase may be overexpressed and/or active in the cytosol, for instance by deletion of a peroxisomal targeting signal. In the event the malate synthase is a *S. cerevisiae* malate synthase, for instance the native malate synthase is altered by the deletion of the SKL carboxy-terminal sequence.

In another embodiment, a host cell of the invention may comprise a disruption of a gene encoding an enzyme of the ethanol fermentation pathway. A gene encoding an enzyme of an ethanol fermentation pathway, may be pyruvate decarboxylase (EC 4.1.1.1), catalyzing the reaction from pyruvate to acetaldehyde, or alcohol dehydrogenase (EC 1.1.1.1), catalyzing the reaction from acetaldehyde to ethanol. Preferably, a host cell of the invention comprises a disruption of one, two or more genes encoding an alcohol dehydrogenase. In the event the fungal cell is a yeast, e.g. *S. cerevisiae*, the yeast preferably comprises a disruption of one or more alcohol dehydrogenase genes (adh1 adh2, adh3, adh4, adh5).

Alternatively or in addition, the host cell of the invention may comprise at least one gene encoding glycerol-3-phosphate dehydrogenase which is not functional. A glycerol-3-phosphate dehydrogenase gene that is not functional is used herein to describe a eukaryotic cell, which comprises a reduced glycerol-3-phosphate dehydrogenase activity, for instance by mutation, disruption, or deletion of the gene encoding glycerol-3-phosphate dehydrogenase, resulting in a decreased formation of glycerol as compared to a wild-type cell.

Cytosolic expression of the enzymes described above may be obtained by deletion of a peroxisomal or mitochondrial targeting signal. The presence of a peroxisomal or mitochondrial targeting signal may for instance be determined by the method disclosed by Schluter et al., Nucleid Acid Research 2007, 35, D815-D822.

As used herein, a genetically modified yeast according to the present invention is defined as a cell which contains, or is transformed or genetically modified with or a nucleotide sequence or polypeptide that does not naturally occur in the yeast cell, or it contains an additional copy or additional copies of an endogenous nucleic acid sequence, or it contains a deletion or disruption of an endogenous or homologous nucleotide sequence. A wild-type eukaryotic cell is herein defined as the parental cell of the recombinant cell.

As used herein, the terms “gene” and “recombinant gene” refer to nucleic acid molecules which include an open reading frame encoding a FRD variant or other enzyme as described herein. A gene may include coding sequences, non-coding sequences, introns and regulatory sequences. That is to say, a “gene”, as used herein, may refer to an isolated nucleic acid molecule as defined herein. Accordingly, the term “gene”, in the context of the present application, does not refer only to naturally-occurring sequences.

The term “endogenous” when used to indicate the relation between a given (recombinant) nucleic acid or polypeptide molecule and a given host organism or host cell, is understood to mean that in nature the nucleic acid or polypeptide molecule is produced by a host cell or organism of the same species, preferably of the same variety or strain.

The term “heterologous” when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but have been obtained from another cell or synthetically or recombinantly produced.

The invention relates to a process for the production of a dicarboxylic acid. The terms “dicarboxylic acid” and “dicarboxylate”, such as “succinic acid” and “succinate”, have the same meaning herein and are used interchangeably, the first being the hydrogenated form of the latter.

According to the invention, there is thus provided a method for the production of a dicarboxylic acid, such as succinic acid, which method comprises fermenting a host cell according as described herein under conditions suitable for production of a dicarboxylic acid, such as succinic acid and, optionally, recovering the a dicarboxylic acid, such as succinic acid.

In the process a host cell is fermented in a vessel comprising a suitable fermentation medium. The term fermenting, fermentation or fermented and the like as used herein refers to the microbial production of compounds, here dicarboxylic acids from carbohydrates.

Preferably, the fermentation product is a dicarboxylic acid, preferably malic acid, fumaric acid or succinic acid or adipic acid, preferably succinic acid.

A batch fermentation is defined herein as a fermentation wherein all nutrients are added at the start of a fermentation.

A fed-batch fermentation is a batch fermentation wherein the nutrients are added during the fermentation. Products in a batch and fed-batch fermentation may be harvested at a suitable moment, for instance when one or more nutrients are exhausted A continuous fermentation is a fermentation wherein nutrients are continuously added to the fermentation and wherein products are continuously removed from the fermentation.

In one embodiment fermenting the host cell in the process of the invention is carried out under carbohydrate limiting conditions. As used herein, carbohydrate limiting conditions are defined as maintaining the carbohydrate concentration below 10 g/l, for example about 5 g/l.

The process for the production of dicarboxylic acid according to the present invention may be carried out in any suitable volume and scale, preferably on an industrial scale. Industrial scale is defined herein as a volume of at least 10, or 100 liters, preferably at least 1 cubic meter, preferably at least 10, or 100 cubic meters, preferably at least 1000 cubic meters, usually below 10,000 cubic meters.

Fermenting the host cell in the process of the invention may be carried out in any suitable fermentation medium comprising a suitable nitrogen source, carbohydrate and other nutrients required for growth and production of a dicarboxylic acid in the process of the invention. A suitable carbohydrate in the fermentation process according to the invention may be glucose, galactose, xylose, arabinose, sucrose, or maltose.

In one embodiment, the fermentation process is carried out under a partial $CO_2$ pressure of between 5% and 60%, preferably about 50%.

The pH during the process for the production of dicarboxylic acid usually lowers during the production of the dicarboxylic acid. Preferably, the pH in the process for the production of dicarboxylic acid ranges between 1 and 5, preferably between 1.5 and 4.5, more preferably between 2 and 4.

In another preferred embodiment the process according to the present invention comprises a step of preculturing the host cell under aerobic conditions in the presence of a carbohydrate. Preferably, the fermentation of the host cell during preculturing is carried out at a pH of between 4 and 6. Preferably, the carbohydrate during preculturing is a non-repressing carbohydrate, preferably galactose. It has been found advantageous to preculture host cells on a non-repressing carbohydrate, since this prevents glucose repression occurring, which may negatively influence the amount of biomass produced. In addition, it has been found that a step of preculturing host cells under aerobic conditions results in a higher biomass yield and a faster growth. Preferably, the preculturing is carried out in batch mode.

A propagation step for producing increased biomass is typically carried out, preferably under carbohydrate limiting conditions.

A process for producing a dicarboxylic acid may be carried out at any suitable temperature. A suitable temperature may for instance be between about 10 and about 40 degrees Celsius, for instance between about 15 and about 30 degrees Celsius.

The process for the production of a dicarboxylic acid may further comprise recovering the dicarboxylic acid. Recovery of the dicarboxylic acid may be carried out by any suitable method.

In one embodiment, a dicarboxylic acid that is produced in a process as disclosed herein is recovered from the fermentation medium. Recovery of a dicarboxylic acid may be carried out by any suitable method known in the art, for instance by crystallization, ammonium precipitation, ion exchange technology, centrifugation or filtration or any suitable combination of these methods.

In a preferred embodiment, the recovery of dicarboxylic acid comprises crystallizing the dicarboxylic acid and forming dicarboxylic acid crystals. Preferably, the crystallizing of dicarboxylic acid comprises removing part of the fermentation medium, preferably by evaporation, to obtain a concentrated medium.

According to the present invention, a dicarboxylic acid, such as succinic acid may be recovered by crystallizing the dicarboxylic acid, such as succinic acid, from an aqueous solution having a pH of between 1 and 5 and comprising succinic acid, comprising evaporating part of the aqueous solution to obtain a concentrated solution, lowering the temperature of the concentrated solution to a value of between 5 and 35 degrees Celsius, wherein succinic acid crystals are formed. Preferably, the crystallizing comprises bringing the temperature of the concentrated medium to a temperature of between 10 and 30 degrees Celsius, preferably between 15 and 25 degrees Celsius. Preferably, the fermentation medium has a pH of between 1.5 and 4.5, preferably between 2 and 4.

It has been found that crystallizing a dicarboxylic acid, such as succinic acid, at higher temperatures such as between 10 and 30 degrees Celsius results in crystals of a dicarboxylic acid, such as succinic acid, with a lower amount of impurities such as organic acid, protein, color and/or odor, than crystals of a dicarboxylic acid, such as succinic acid, that were crystallized at a low temperature of below 10 degrees.

Another advantage of crystallizing succinic acid at a higher temperature is that it requires a lower amount of energy for cooling the aqueous solution as compared to a process wherein crystallizing the dicarboxylic acid is carried out below 10 or 5 degrees Celsius, resulting in a more economical and sustainable process.

Preferably, the crystallizing of the dicarboxylic acid, such as succinic acid, comprises a step of washing the dicarboxylic acid crystals. Dicarboxylic acid, such as succinic acid, may be crystallized directly from the fermentation medium having a pH of between 1 and 5 to a purity of at least 90% w/w, preferably at least 95, 96, 97, or at least 98%, or 99 to 100% w/w.

Preferably, the recovery of the dicarboxylic acid, preferably succinic acid, comprises removing the biomass from the fermentation medium and crystallizing the dicarboxylic acid, preferably crystallizing as described herein above. Preferably, the removing of biomass is carried out by filtration.

In a preferred embodiment, the process for the production of a dicarboxylic acid further comprises using the dicarboxylic acid in an industrial process. An industrial process for a dicarboxylic acid may be the application as a cosmetic additive, deicing agent, food additive or as a building block for (bio)polymers.

In a preferred embodiment, the fermentation medium comprises an amount of succinic acid of between 1 and 150 g/l, preferably between 5 and 100 g/l, more preferably between 10 and 80 g/l or between 15 and 60 g/l of succinic acid. In any event, a host cell of the invention will typically be capable of accumulating more succinic acid in the fermentation medium in comparison with an equivalent host cell which expresses the reference polypeptide.

In another aspect the present invention relates to a process for crystallizing succinic acid from an aqueous solution having a pH of between 1 and 5 and comprising succinic acid, comprising removing part of the aqueous solution by evaporation to obtain a concentrated solution, and bringing the temperature of the concentrated solution to a value of between 10 and 30 degrees Celsius, wherein succinic acid crystals are formed. Preferably, the crystallizing comprises bringing the temperature of the concentrated solution between 15 and 25 degrees Celsius, preferably between 18 and 22 degrees Celsius. Preferably, the aqueous solution has a pH of between 1.5 and 4.5, preferably between 2 and 4. The aqueous solution may be any suitable solution comprising succinic acid. The aqueous solution may comprise soluble constituents and insoluble constituents and, such as (fragments of) microbial cells, protein, plant biomass lignocellulose, cellulose and the like. Preferably the aqueous solution is a fermentation medium, preferably a fermentation medium obtainable by a process for the production of a dicarboxylic acid as described herein.

Preferably, the dicarboxylic acid, such as succinic acid, that is prepared in the process according to the present invention is further converted into a desirable product. A desirable product may for instance be a polymer, such as polybutylene succinic acid (PBS), a deicing agent, or a surfactant. That is to say, the invention provides a method for the production of a product, for example, a polymer, such as polybutylene succinic acid (PBS), a deicing agent, or a surfactant, which method comprises: producing a carboxylic acid as described herein; and using said dicarboxylic acid in the production of a said product.

For the purpose of this invention, it is defined here that in order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

Standard genetic techniques, such as overexpression of enzymes in the host cells, genetic modification of host cells, or hybridisation techniques, are known methods in the art, such as described in Sambrook and Russel (2001) "Molecular Cloning: A Laboratory Manual (3rd edition), Cold Spring Harbor Laboratory, *Cold Spring Harbor Laboratory Press*, or F. Ausubel et al, eds., "Current protocols in molecular biology", Green Publishing and Wiley Interscience, New York (1987). Methods for transformation, genetic modification etc. of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265,186.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percentage of sequence identity between two amino acid sequences or between two nucleotide sequences may be determined using the Needleman and Wunsch algorithm for the alignment of two sequences. (Needleman, S. B. and Wunsch, C. D. (1970) J. Mal. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at ncbi.nlm.nih.gov/.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

Example 1: Construction of Strain SUC-1099

Generation of PCR Fragments

PCR fragments were generated using Phusion DNA polymerase (New England Biolabs, USA) according to manufacturer's instructions.

Primer sequences described in SEQ ID NO: 9 and SEQ ID NO: 10 were used to generate PCR fragment 1 consisting of the 5' INT59 integration site, using genomic DNA of strain *Saccharomyces cerevisiae* strain CEN.PK 113-7D (MATa HIS3 LEU2 TRP1 MAL2-8 SUC2), described by Daran-Lapujade et al., (FEMS Yeast Res (2003) 4: 285-296) as template.

PCR fragment 2 was generated by using the primer sequences described in SEQ ID NO: 11 and SEQ ID NO: 12, using SEQ ID NO: 1 as template. SEQ ID NO: 1 encodes phosphoenolpyruvate carboxykinase (PCKa) from *Actinobacillus succinogenes*, as disclosed in patent application WO2009/065780. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *S. cerevisiae*, i.e. the TPI1-promoter controls the expression of the PCKa-gene. Proper termination is controlled by a terminator sequence from *S. cerevisiae*, i.e. the GND2-terminator.

PCR fragment 3 was generated by using the primer sequences described in SEQ ID NO: 13 and SEQ ID NO: 14, using SEQ ID NO: 2 as template. SEQ ID NO: 2 encodes pyruvate carboxylase (PYC2) from *Saccharomyces cerevisiae*, as disclosed in patent application WO2009/065780. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *S. cerevisiae*, i.e. the PGK1-promoter controls the expression of the PYC2-gene. Proper termination is controlled by a terminator sequence from *S. cerevisiae*, i.e. the ADH1-terminator.

PCR fragment 4 was generated by using the primer sequences described in SEQ ID NO: 15 and SEQ ID NO: 16, using SEQ ID NO: 3 as template. SEQ ID NO: 3 encodes a KanMX selection marker functional in *Saccharomyces cerevisiae* which was amplified from plasmid pUG7-EcoRV. pUG7-EcoRV is a variant of plasmid pUG6 described by Gueldener et al., (Nucleic Acids Res. 1996 Jul. 1; 24(13): 2519-24), in which the loxP sites present in pUG6 were changed into lox66 and lox71 sites (Lambert et al., Appl. Environ. Microbiol. 2007 February; 73(4):1126-35. Epub 2006 Dec. 1.)

PCR fragment 5 was generated by using the primer sequences described in SEQ ID NO: 17 and SEQ ID NO: 18, using SEQ ID NO: 4 as template. SEQ ID NO: 4 encodes a putative dicarboxylic acid transporter from *Aspergillus niger*, as disclosed in EP2495304. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *S. cerevisiae*, i.e. the ENO1-promoter controls the expression of the DCT_02-gene. Proper termination is controlled by a terminator sequence from *S. cerevisiae*, i.e. the TEF2-terminator.

PCR fragment 6 was generated by using the primer sequences described in SEQ ID NO: 19 and SEQ ID NO: 20, using SEQ ID NO: 5 as template. SEQ ID NO: 5 encodes malate dehydrogenase (MDH3) from *Saccharomyces cerevisiae*, as disclosed in patent application WO2009/065778. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *S. cerevisiae*, i.e. the FBA1-promoter controls the expression of the MDH3-gene. Proper termination is controlled by a terminator sequence from *S. cerevisiae*, i.e. the GPM1-terminator.

PCR fragment 7 was generated by using the primer sequences described in SEQ ID NO: 21 and SEQ ID NO: 22, using SEQ ID NO: 6 as template. SEQ ID NO: 6 encodes fumarase (fumB) from *Escherichia coli* (E.C. 4.2.1.2, UniProt accession number P14407). The gene sequence was codon pair optimized for expression in *S. cerevisiae* as disclosed in patent application WO2008/000632. The synthetic sequence, which includes promoter-gene-terminator sequence, including appropriate restriction sites, was synthesized by DNA 2.0 (Menlo Park, Calif., USA). The synthetic gene is under control of (or operable linked to) a promoter from *Kluyveromyces lactis*, i.e. the glyceraldehyde 3-phosphate dehydrogenase promoter controls the expression of the fumB-gene. Proper termination is controlled by a terminator sequence from *S. cerevisiae*, i.e. the TDH1-terminator.

Primer sequences described in SEQ ID NO: 23 and SEQ ID NO: 24 were used to generate PCR fragment 8 consisting of the 3' INT59 integration site, using genomic DNA of strain CEN.PK 113-7D as template.

PCR fragments 1 to 8 were purified using the DNA Clean & Concentrator™-25 kit (Zymo Research, Irvine, Calif., USA) according to manufacturer's instructions.

Transformation to CEN.PK113-7D in Order to Construct Strain SUC-1099

Yeast transformation was done by a method known by persons skilled in the art. *S. cerevisiae* strain CEN.PK113-7D was transformed with purified PCR fragments 1 to 8. PCR fragments 2 to 7 contained overlaps at their 5' and 3' ends and PCR fragments 1 and 8 at their 3' and 5' end respectively, such that this allowed homologous recombination of all eight PCR fragments. The 5' end of PCR fragment 1 and the 3' end of PCR fragment 8 were homologous to the INT59 locus and enabled integration of all eight PCR fragments in the INT59 locus (see FIG. 1). This resulted in one linear fragment consisting of PCR fragments 1 to 8 integrated in the INT59 locus. This method of integration is described in patent application WO2013076280. The INT59 locus is located at chromosome XI, 923 bp downstream of YKR092C and 922 bp upstream of YKR093W.

Transformation mixtures were plated on YEPh-agar (per liter: 10 grams yeast extract, 20 grams PhytonePeptone, 20 grams galactose, 20 grams agar) containing 100 μg G418 (Sigma Aldrich, Zwijndrecht, The Netherlands) per ml. After three days of growth at 30° C., individual transformants were re-streaked on YEPh—agar plates containing 20 grams galactose per liter and 100 µg G418 per ml. Presence of all introduced genes was confirmed by using PCR using primer sequences that can anneal to the coding sequences of the ORF's encoded by SEQ ID NO: 2 to SEQ ID NO: 6. The resulting strain was named SUC-1099.

Example 2: Transformation of Fumarate Reductase to Strain SUC-1099 and Production of Succinic Acid in Resulting Transformants Generation of PCR Fragments PCR fragments were generated using Phusion DNA polymerase (New England Biolabs, USA) according to manufacturer's instructions.

Primer sequences described in SEQ ID NO: 25 and SEQ ID NO: 26 were used to generate PCR fragment 9 consisting of the 5' INT1 integration site, using genomic DNA of strain CEN.PK 113-7D as template.

PCR fragment 10 was generated by using the primer sequences described in SEQ ID NO: 27 and SEQ ID NO: 28, using SEQ ID NO: 7 as template. SEQ ID NO: 7 encodes a nourseothricin selection marker functional in *Saccharomyces cerevisiae* which was amplified from a modified version of plasmid pUG7-Nat. pUG7-Nat is a variant of plasmid pUG6 described by Gueldener et al., (Nucleic Acids Res. 1996 Jul. 1; 24(13):2519-24), in which the loxP sites present in pUG6 were changed into lox66 and lox71 sites (Lambert et al., Appl. Environ. Microbiol. 2007 February; 73(4):1126-35. Epub 2006 Dec. 1) and in which the KanMX marker was replaced by a nourseothricin marker (Goldstein and McCusker, Yeast. 1999 October; 15(14):1541-53).

PCR fragment 11 was generated by using the primer sequences described in SEQ ID NO: 31 and SEQ ID NO: 32, using SEQ ID NO: 8 as template. SEQ ID NO: 8 encodes fumarate reductase (FRDg) from *Trypanosoma brucei*, as disclosed in patent application WO2009/065778. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *S. cerevisiae*, i.e. the TDH3-promoter controls the expression of the FRDg-gene. Proper termination is controlled by a terminator sequence from *S. cerevisiae*, i.e. the TAL1-terminator. Primer sequences described in SEQ ID NO: 29 and SEQ ID NO: 30 were used to generate PCR fragment 12 consisting of the 3' INT1 integration site, using genomic DNA of strain CEN.PK 113-7D as template.

PCR fragments 9 to 12 were purified using the DNA Clean & Concentrator™-25 kit (Zymo Research, Irvine, Calif., USA) according to manufacturer's instructions.

Transformation to SUC-1099

Yeast transformation was done by a method known by persons skilled in the art. *S. cerevisiae* strain CEN.PK113-7D was transformed with purified PCR fragments 9 to 12. PCR fragments 10 and 11 contained overlaps at their 5' and 3' ends and PCR fragments 9 and 12 contained overlaps at their 3' and 5' end respectively, such that this allowed homologous recombination of all four PCR fragments. The 5' end of PCR fragment 9 and the 3' end of PCR fragment 12 were homologous to the INT1 locus and enabled integration of all four PCR fragments in the INT1 locus (see FIG. 2). This resulted in one linear fragment consisting of PCR fragments 9 to 12 integrated in the INT1 locus. This method of integration is described in patent application WO2013076280. The INT1 locus is located at chromosome XV, 659 bp downstream of YOR071c and 998 bp upstream of YOR070c. This approach resulted in expression of the fumarate reductase protein of 1139 amino acids as indicated in SEQ ID NO: 33, which lacks the C-terminal amino acid SKI as compared to the native sequence from *T. brucei.*

Transformation mixtures were plated on YEPh-agar (per liter: 10 grams yeast extract, 20 grams PhytonePeptone, 20 grams galactose, 20 grams agar)) containing 100 µg nourseothricin (Jena Bioscience, Germany) per ml. After three days of growth at 30° C., individual transformants were re-streaked on YEPh-agar plates containing 20 grams galactose per liter and 100 µg nourseothricin per ml. Presence of the introduced genes was confirmed by using PCR using primer sequences that can anneal to the coding sequences of the ORF's encoded by SEQ ID NO: 7 and SEQ ID NO: 8. Three resulting individual colonies were named P5107#1_#02, P5107#1_#03 and PS107#1_#04.

Succinic Acid Production

To determine succinic acid production, strain SUC-1099 was grown in triplicate and transformants P5107#1_#02, P5107#1_#03 and P5107#1_#04 were grown in micro titers plates using galactose as C-source. After a growth phase to generate biomass, a production experiment started by re-suspending cells into cultivation medium. 30 g/L succinic acid was spiked to the cultivation medium at the start of the production experiment. Supernatant samples were taken after 96 hours of cultivation.

Samples for flow NMR were prepared as follows: From each well flask, 600 microliter culture was taken and centrifuged for 1 minute at 14,000 rpm. 50 microliters supernatant was transferred to a 96-deep well MTP plate. 450 microliters internal standard (20 g/L maleic acid, 40 g/l EDTA in D20) and 500 microliters of 80:20 H2O/D2O were added to each sample. Dicarboxylic acid, including succinic acid concentrations and other compounds like glucose in the fermentation supernatant were determined with a Bruker BEST avance II 500 MHz spectrometer. The NMR spectra were recorded with a water suppression pulse program at 27 degrees Celsius with a relaxation delay of 30 s.

In the supernatant of SUC-1099, an average titer of 30.9 g/L succinic acid was measured. When FRDg was introduced and overexpressed in SUC-1099, an average titer of 53.5 g/L succinic acid was measured.

Example 3: Transformation of Fumarate Reductase Variants to Strain SUC-1099 and Production of Succinic Acid in Resulting Transformants Generation of PCR Fragments PCR fragments 9, 10 and 12 were generated as described in Example 2. Synthetic nucleotide sequences encoding different protein variants of the reference fumarate reductase sequence that is described in SEQ ID NO: 33 were synthesized by DNA 2.0 (Menlo Park, Calif., USA). The synthetic nucleotide sequences encode a mutated amino acid relative to the reference FRDg sequence (SEQ ID NO: 33) at the positions indicated in Table 2. Apart from encoding the indicated mutated amino acids in Table 2 the synthetic nucleotide sequence variants are identical to SEQ ID NO: 8. The synthetic gene is under control of (or operable linked to) a promoter from *S. cerevisiae*, i.e. the TDH3-promoter controls the expression of the mutated FRD-gene (FCC). Proper termination is controlled by a terminator sequence from *S. cerevisiae*, i.e. the TAL1-terminator.

The synthetic gene sequences containing amongst others a TDH3 promoter—mutated FRD—TAL1 terminator and were amplified by PCR using the primer sequences described in SEQ ID NO: 31 and SEQ ID NO: 32, to generate PCR fragments 13 to 22 (see Table 2).

PCR fragments 9, 10, 12 and 13 to 22 were purified using the DNA Clean & Concentrator™-25 kit (Zymo Research, Irvine, Calif., USA) according to manufacturer's instructions.

Transformation to SUC-1099

Strain SUC-1099 was transformed with purified PCR fragments 9, 10 and 12 in combination with PCR fragments 13 to 22 individually. PCR fragment 10 and PCR fragments 13 to 22 contained overlaps at their 5' and 3' ends and PCR fragments 9 and 12 contained overlaps at their 3' and 5' end respectively, such that this allowed homologous recombination of all four PCR fragments. The 5' end of PCR fragment 9 and the 3' end of PCR fragment 12 were homologous to the INT1 locus and enabled integration of all four PCR fragments in the INT1 locus (FIG. 2). Transformation and selection of transformants is described in Example 2.

Succinic Acid Production

To determine succinic acid production, four independent SUC-1099 transformants expressing mutated fumarate reductase sequences were grown in micro titer plates and succinic acid titers were measured as described in Example 2. Average succinic acid titers are depicted in Table 2. The average production of succinic acid of several SUC-1099 transformants expressing mutated fumarate reductase sequences exceeded 55 g/L succinic acid. This is significantly more than the average succinic acid titer of SUC-1099 transformed with the reference FRDg sequence. By significantly more it is meant that the 95% confidence intervals of succinic titers for strains with reference and improved mutated fumarate reductase sequences do not overlap.

TABLE 2

Average succinic acid titers measured in the supernatant of production medium after 4 days cultivation of strain SUC-1099, expressing phosphoenolpyruvate carboxykinase (PCKa), pyruvate carboxylase (PYC2), malate dehydrogenase (MDH3), fumarase (fumB), dicarboxylic acid transporter (DCT_02) transformed with reference fumarate reductase (SEQ ID NO: 33) or mutated fumarate reductase, which contains mutations as compared to the reference sequence in the amino acid positions indicated below.

| PCR fragment | Clone | Mutation in position 1042 | 1071 | 1072 | 1082 | 1083 | Average succinic acid titer (g/L) |
|---|---|---|---|---|---|---|---|
| 11 | Reference | E | N | R | G | F | 53.5 |
| 13 | FCC_040 | R | T | R | K | Y | 58.2 |
| 14 | FCC_045 | R | T | K | K | F | 57.1 |
| 15 | FCC_046 | R | T | K | K | Y | 58.2 |
| 16 | FCC_048 | R | T | K | R | Y | 58.9 |
| 17 | FCC_065 | K | T | R | R | F | 59.9 |
| 18 | FCC_069 | K | T | K | K | F | 58.5 |
| 19 | FCC_070 | K | T | K | K | Y | 59.7 |
| 20 | FCC_075 | Q | S | R | K | F | 56.3 |
| 21 | FCC_076 | Q | S | R | K | Y | 61.3 |
| 22 | FCC_078 | Q | S | R | R | Y | 64.5 |

The introduction of a positively charged residue (lysine or arginine; K or R) at amino acid position 1082 is unique, because the reference fumarate reductase sequence contains a small uncharged glycine (G) at this position. Furthermore, no previously described natural variant or publically available mutant of fumarate reductase contains a charged residue at position number 1082. As depicted in Table 2, replacing the glycine in the reference FRDg sequence by a charged residue is advantageous for achieving increased succinic acid titers.

Example 4: Measuring NADH and NADPH Specific Activity of Fumarate Reductase (FRD) Variants Transformants generated in Example 3 were grown as described in Example 2. The biomass was harvested by centrifugation (4000 rpm, 10 min, 4° C.) and washed twice with PBS (phosphate buffered saline, Sigma Aldrich) after which the cell pellets were frozen at −20° C. Cell disruption was achieved in square welled 96-deepwell micro titer plates (MTP) using 0.5 mm acid washed glass beads in combination with the TissueLyser II from Qiagen (3000 rpm for 2×10 sec). Glass beads taking up a volume of 600 μl were added to the cell pellet before addition of 1 ml in vivo like-assay medium described in van Eunen et al. (*FEBS Journal* 277: 749-760) containing 0.5 mM DTT (dithiothreitol, Sigma-Aldrich) and 0.1 mM PMSF (phenylmethanesulfonyl fluoride, Amresco). Glass beads were added by inverting the deep well MTP containing the frozen pellets over a standard MTP where each well is filled completely with glass beads(=a volume of 300 μl) and then inverting both plates, so that the glass beads fall onto the cell pellets. This process was repeated to obtain 600 μl glass beads in the cell pellets. After cell disruption, cell debris was pelleted by centrifugation (4000 rpm, 30 min, 4° C.). The supernatant (soluble cell extracts) were collected and stored on ice. Protein concentration of the extracts was determined by Bradford, using bovine serum albumin (BSA) as standard.

Figure 3A:
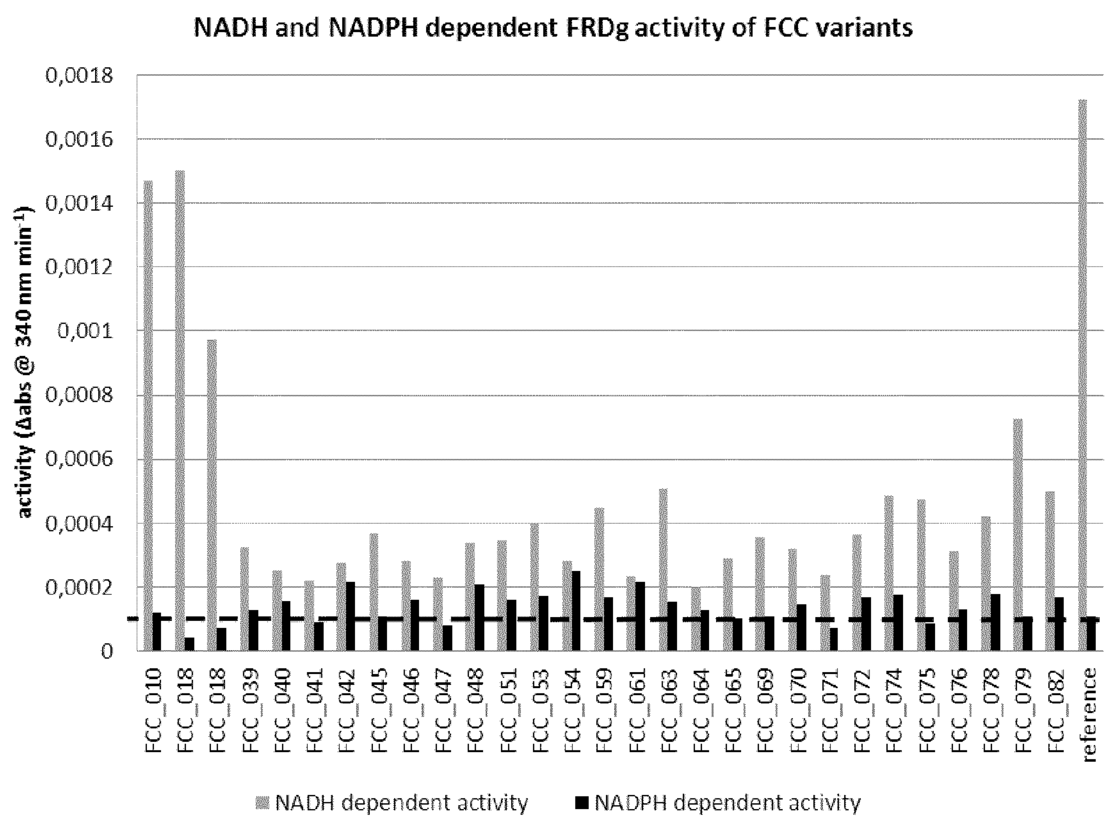
FIG. 3*a*: complete figure.
Figure 3B:
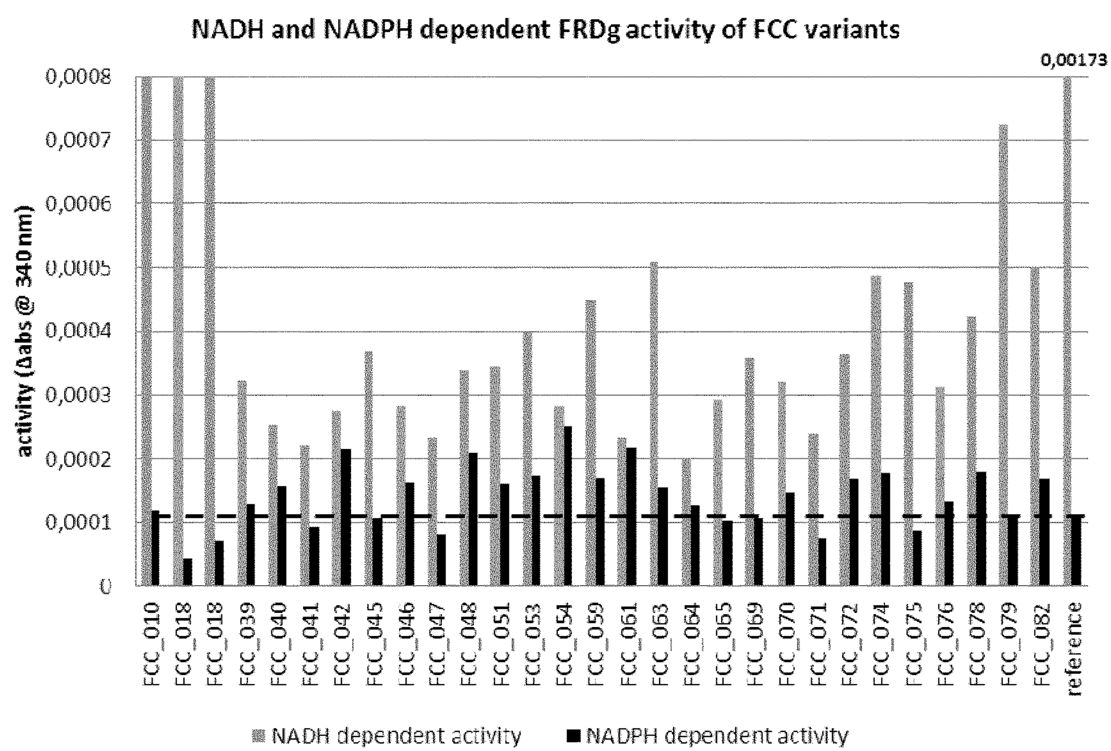
FIG. 3*b*: same graph as in 3a, but zooms in on lower region of y-axis. Label corresponds to value of reference activity.

Fumarate reductase (FRD) activity was assayed spectrophotometrically by following the decrease in absorbance at 340 nm caused by the oxidation of NADH or NADPH to NAD+ or NADP+. Assay mixtures contained 150 μM NADH or NADPH, 1 mM fumaric acid, 0.5 mg protein $mL^{-1}$ soluble cell extracts in in vivo-like assay medium in a final volume of 200 μl. Reactions were started by the addition of fumaric acid, were followed for 9 minutes at 30 degrees Celsius and the slope was used as a measure of NADH or NADPH dependent FRD activity. Absorbance was measured using a Tecan Infinite M1000 plate reader. NADH dependent activity of each variant was compared to the NADPH activity. The ratio of NADPH:NADH dependent activity for each variant was calculated so that the variants could be ranked. FIGS. 3*a* and 3*b* show the NADPH and NADH dependent FRD activities for all variants that contain beneficial mutations for increased succinic production described in Example 3.

Example 5: Construction of Strain SUC-501

Strain SUC-501 was constructed by replacing the two SpMAE1 dicarboxylic acid transporters in strain SUC-401, described in WO 2013/004670, with DCT_02 dicarboxylic acid transporters, similar as described for SUC-489 in WO 2013/004670. SUC-401 was transformed with the purified 7.7 kB fragment of plasmid pSUC174 restricted with Bsu36I and FseI. Plasmid pSUC174 is described in WO 2013/004670. The 7.7 kB fragment contains at the 5' end the FUMR synthetic gene, the DCT_02 transporter and a KanMX selection marker flanked by lox66/lox71 sites (Lambert J M, Bongers R S, Kleerebezem M., Appl Environ Microbiol. 2007 February; 73(4):1126-35), and at the 3' end the MDH3 synthetic gene.

Correct transformants were initially selected for their resistance against G418, due to integration of the KanMX resistance marker. Next, a diagnostic PCR on intermediate strain SUC-461 was performed to confirm replacement of the SpMAE1 synthetic gene by the DCT_02 synthetic gene. The KanMX marker flanked by lox66 and lox71 sites was removed from strain SUC-461 by transformation of Cre-recombinase (Guldener U, Heck S, Fielder T, Beinhauer J, Hegemann J H., Nucleic Acids Res. 1996 Jul. 1; 24(13): 2519-2524) using plasmid pSH65 containing a phleomycin resistance marker. Subsequently plasmid pSH65 was cured from the cells by growth on non-selective medium (YEP 2% galactose), remaining one lox72 in the genomic DNA. The resulting strain was designated SUC-464.

Next, a second copy of the SpMAE1 gene present in the genomic DNA of SUC-401 was replaced. SUC-464 was transformed with the purified 7.7 kB fragment of plasmid pSUC174 restricted with Bsu36I and FseI. Correct transformants were initially selected for their resistance against G418, due to integration of the KanMX resistance marker. The fragment from pSUC174 can either replace the remaining SpMAE1 gene or the introduced DCT_02 gene. A diagnostic PCR on the transformants was performed to confirm replacement of both the SpMAE1 synthetic genes by the DCT_02 synthetic gene. One transformant containing two copies of the DCT_02 gene was name SUC-467. The KanMX marker flanked by lox66 and lox71 sites was removed from strain SUC-467 by transformation of Cre-recombinase (Guldener U, Heck S, Fielder T, Beinhauer J, Hegemann J H., Nucleic Acids Res. 1996 Jul. 1; 24(13): 2519-2524) using plasmid pSH65 containing a phleomycin resistance marker. Subsequently plasmid pSH65 was cured from the cells by growth on non-selective medium (YEP 2% galactose), remaining one lox72 in the genomic DNA.

The resulting strain was designated SUC-501 (MATa ura3,52 HIS3 LEU2 TRP1 sit2::TPI1p-PCKa-PMA1t; TDH3p-FRDg-TDH3t sit4::TDH3p-MDH3-TDH3t; ENO1p-DCT_02-ENO1 t; TPI1 p-FUMR-PMA1t; lox72 adh1::PGK1p-PYC2-PGK1t; URA3p-URA3-URA3t MAL2-8 SUC2).

Example 6: Selection of Strain SUC-723 from Adaptive Evolution of SUC-501

SUC-501 was grown in an auxostat culture of 1.5 liters in a 2 liter fermentor containing medium with a concentration of succinic acid of 50 g/L at pH3 at 30° C. Stirrer speed was set at 150 rpm and the airflow was set at 2 Nl/hr. The inoculum size was 150 g biomass (grown in shakeflask in Verduyn medium (Verduyn C, Postma E, Scheffers W A, Van Dijken J P. Yeast, 1992 July; 8(7):501-517)) with galactose as carbon source). The feed rate of the medium to the auxostat culture was gradually increased over a period of 60 days. The initial feed rate was set to a dilution rate 0.05 $h^{-1}$, the final feed rate set to a dilution rate of $0.16^{-1}$. The feed rate was maximized to keep the culture at the maximum possible growth rate while avoiding ethanol formation and washout of the culture.

The feed medium was based on Verduyn et al. (Verduyn C, Postma E, Scheffers W A, Van Dijken J P. Yeast, 1992 July; 8(7):501-517), with modifications in the carbon and nitrogen sources, as described below (see table 3). pH was set to 3 (using 1M KOH/1M $H_2SO_4$).

Succinic acid production was measured at several time points during the 60 days of growth of the auxostat culture, using the method described in Example 2 in WO 2013/004670. After 30 days the succinic acid titers produced by the auxostat culture was similar to that of the non-evolved SUC-501. After 60 days of adaptive evolution the auxostat culture showed a decrease in succinic acid titer of more than 50% compared to the SUC-501.

A single colony isolate obtained from the SUC-501 culture after 60 days of growth in the auxostat culture was named SUC-723. PCR analysis, using primers specific for the integrated open reading frames using a method known to a person skilled in the art, of the succinic acid genes that were present in the SUC-501 strain (FUMR, MDH3, PCKa, FRDg, PYC2, DCT02) revealed that the FRDg gene is not present in the SUC-723. The presence of all other succinic acid genes that are present in the SUC-501 could be demonstrated in the SUC-723 strain.

TABLE 3

Medium composition of feed-medium used in adaptive evolution of SUC-501 described in Example 6. The feed medium was based on Verduyn et al. (Verduyn C, Postma E, Scheffers W A, Van Dijken J P. Yeast, 1992 July; 8(7): 501-517).

| Raw material | | Concentration (g/kg) |
|---|---|---|
| Dextrose | $C_6H_{12}O_6 \cdot H_2O$ | 27.5 |
| Ammonium sulphate | $(NH_4)_2SO_4$ | 5.0 |
| Potassium dihydrogen phosphate | $KH_2PO_4$ | 3.0 |
| Magnesium sulphate | $MgSO_4 \cdot 7H_2O$ | 0.5 |
| Trace element solution | | 1 |
| Vitamin solution | | 1 |
| Succinic acid | $C_4H_6O_4$ | 50 |

Example 7: Transformation of Fumarate Reductase to Strain SUC-723 and Production of Succinic Acid in Resulting Transformants To test whether the reduced succinic acid production of SUC-723 is solely due to the absence of the FRDg gene (and that the SUC-723 can consequently be used to assess the functionality of variants of the FRDg gene in succinic acid production) an FRDg expression construct was integrated in the SUC-723 strain.

Generation of PCR Fragments

PCR fragments were generated using Phusion DNA polymerase (New England Biolabs, USA) according to manufacturer's instructions.

Primer sequences described in SEQ ID NO: 34 and SEQ ID NO: 35 were used to generate PCR fragment 23 consisting of the 5' INT12 integration site, using genomic DNA of strain CEN.PK113-7D as template.

PCR fragments 10 and 11 were generated as described in Example 2.

Primer sequences described in SEQ ID NO: 36 and SEQ ID NO: 37 were used to generate PCR fragment 24 consisting of the 3' INT12 integration site, using genomic DNA of strain CEN.PK 113-7D as template.

PCR fragments 10, 11, 23 and 24 were purified using the DNA Clean & Concentrator™-25 kit (Zymo Research, Irvine, Calif., USA) according to manufacturer's instructions.

Transformation to SUC-723

Yeast transformation was done by a method known by persons skilled in the art. *S. cerevisiae* strain SUC-723 was transformed with purified PCR fragments 10, 11, 23 and 24. PCR fragments 10 and 11 contained overlaps at their 5' and 3' ends and PCR fragments 23 and 24 contained overlaps at their 3' and 5' end respectively, such that this allowed homologous recombination of all four PCR fragments (see FIG. 4). The 5' end of PCR fragment 23 and the 3' end of PCR fragment 24 were homologous to the INT12 locus and enabled integration of all four PCR fragments in the INT12 locus (see FIG. 4). This resulted in one linear fragment consisting of PCR fragments 10, 11, 23 and 24 integrated in the INT12 locus. This method of integration is described in patent application WO2013076280. The INT12 locus is located at chromosome II, 743 bp upstream of the ATG of the YOR071c ORF and 618 bp downstream of the ATG of YBL029C-A. This approach resulted in expression of the fumarate reductase protein of 1139 amino acids as indicated in SEQ ID NO: 33, which lacks the C-terminal amino acid SKI as compared to the native sequence from *T. brucei*, in the strain SUC-723.

Transformation mixtures were plated on YEPh-agar (per liter: 10 grams yeast extract, 20 grams PhytonePeptone, 20 grams galactose, 20 grams agar) containing 100 µg nourseothricin (Jena Bioscience, Germany) per ml. After three to four days of growth at 30° C., individual transformants were re-streaked on YEPh-agar plates containing 20 grams galactose per liter and 100 µg nourseothricin per ml. Presence of the introduced genes was confirmed by using PCR using primer sequences that can anneal to the coding sequences of the ORF's encoded by SEQ ID NO: 7 (nourseothricin marker) and SEQ ID NO: 8 (Fumarate reductase gene). The resulting strain was named SUC-723-FRDg.

Succinic Acid Production of SUC-723 and SUC-723-FRDg

To determine succinic acid production, strains SUC-723 and SUC-723-FRDg were grown in triplicate in micro titers plates using galactose as C-source. After a growth phase to generate biomass, a production experiment started by re-suspending cells into cultivation medium. 30 g/L succinic acid was spiked to the cultivation medium at the start of the production experiment. Supernatant samples were taken after 96 hours of cultivation.

Samples for flow NMR were prepared as follows: From each well flask, 600 microliter culture was taken and centrifuged for 1 minute at 14,000 rpm. 50 microliters supernatant was transferred to a 96-deep well MTP plate. 450 microliters internal standard (20 g/L maleic acid, 40 g/l EDTA in D20) and 500 microliters of 80:20 H2O/D2O were added to each sample. Dicarboxylic acid, including succinic acid concentrations and other compounds like glucose in the fermentation supernatant were determined with a Bruker BEST avance II 500 MHz spectrometer. The NMR spectra were recorded with a water suppression pulse program at 27 degrees Celsius with a relaxation delay of 30 s.

In the supernatant of SUC-723, an average titer of 37.4 g/L succinic acid was measured. When FRDg was introduced and overexpressed in SUC-723, as in SUC-723-FRDg, an average titer of 49.5 g/L succinic acid was measured.

Example 8: Transformation of Fumarate Reductase Variants to Strain SUC-723 and Production of Succinic Acid in Resulting Transformants Generation of PCR Fragments PCR fragment 10 was generated as described in Example 2.

PCR fragments 23 and 24 were generated as described in Example 7.

Synthetic nucleotide sequences encoding different protein variants of the reference fumarate reductase sequence that is described in SEQ ID NO: 33 were synthesized by DNA 2.0 (Menlo Park, Calif., USA). The synthetic nucleotide sequences encode a mutated amino acid relative to the reference FRDg sequence (SEQ ID NO: 33) at the positions indicated in Table 4. Apart from encoding the indicated mutated amino acids in Table 4 the synthetic nucleotide sequence variants are identical to SEQ ID NO: 8. The synthetic gene is under control of (or operable linked to) a promoter from *S. cerevisiae*, i.e. the TDH3-promoter controls the expression of the mutated FRDg-gene (FCC). Proper termination is controlled by a terminator sequence from *S. cerevisiae*, i.e. the TAL1-terminator.

The synthetic gene sequences containing amongst others a TDH3 promoter—mutated FRD-TAL1 terminator and were amplified by PCR using the primer sequences described in SEQ ID NO: 31 and SEQ ID NO: 32, to generate PCR fragments 13, 16, 17, 19, 21 and 22 (see Table 4).

PCR fragments 10, 12, 13, 16, 17, 19, 21, 22, 23 and 24 were purified using the DNA Clean & Concentrator™-25 kit (Zymo Research, Irvine, Calif., USA) according to manufacturer's instructions.

Transformation to SUC-723

Figure 4:
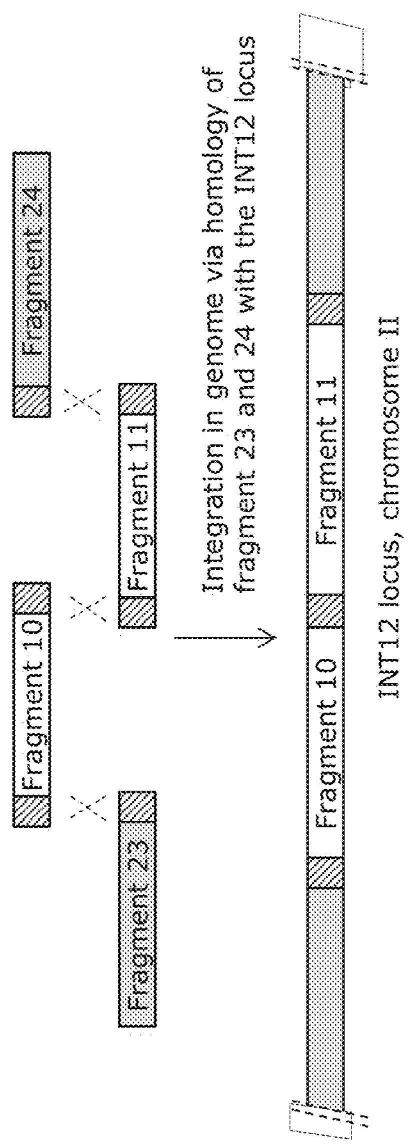
FIG. 4 shows a schematic depiction of integration of fragments 10, 11, 23 and 24. The striped parts indicated in fragments 10, 11, 23 and 24 denote the unique homologous overlap regions leading to the recombination events as indicated by the dashed crosses between the homologous regions. Fragment 11 can be substituted for fragment 13, 16, 17, 19, 21 or 22. Fragment 23 and fragment 24 are homologous to the downstream and upstream region of the INT12 locus on chromosome II, 743 bp upstream of the ATG of the YOR071c ORF and 618 bp downstream of the ATG of YBL029C-A. Homologous recombination results in integration of fragment 10, 11 (or 13, 16, 17, 19, 21 or 22), 23 and 24 into the INT12 locus.

Strain SUC-723 was transformed with purified PCR fragments 23, 10 and 24 in combination with PCR fragments 13, 16, 17, 19, 21 and 22 individually. PCR fragments 10, 13, 16, 17, 19, 21 and 22 contained overlaps at their 5' and 3' ends and PCR fragments 23 and 24 contained overlaps at their 3' and 5' end respectively, such that this allowed homologous recombination of all four PCR fragments. The 5' end of PCR fragment 23 and the 3' end of PCR fragment 24 were homologous to the INT12 locus and enabled integration of all four PCR fragments in the INT12 locus (FIG. 4). Transformation and selection of transformants is described in Example 2.

Of each transformation three colonies were checked by PCR checked using primers hybridizing on the FRDg gene and primers hybridizing on the genomic DNA 5' of the region homologous to PCR fragment 23 and 3' of the region homologous to PCR fragment 24. Of all transformations at least one correct transformant was identified. One colony of the strains transformed with PCR fragments 13, 16, 17, 19, 21 and 22 were named SUC-723-FCC_40, SUC-723-FCC_48, SUC-723-FCC_65, SUC-723-FCC_70, SUC-723-FCC_76 and SUC-723-FCC_78 respectively.

Succinic Acid Production

To determine succinic acid production, SUC-723-FFC_40, SUC-723-FFC_48, SUC-723-FFC_65, SUC-723-FFC_70, SUC-723-FFC_76 and SUC-723-FFC_78 were grown in triplo in micro titer plates and succinic acid titers were measured as described in Example 2. Average succinic acid titers are depicted in Table 4. The average production of succinic acid of several SUC-723 transformants expressing mutated fumarate reductase sequences exceeded 54 g/L succinic acid. This is significantly more than the average succinic acid titer of SUC-723 transformed with the reference FRDg sequence which produced 49.5 g/L succinic acid. By significantly more it is meant that the 95% confidence intervals of succinic titers for strains with reference and improved mutated fumarate reductase sequences do not overlap.

TABLE 4

Average succinic acid titers measured in the supernatant of production medium after 4 days cultivation of strain SUC-723, expressing phosphoenolpyruvate carboxykinase (PCKa), pyruvate carboxylase (PYC2), malate dehydrogenase (MDH3), fumarase (fumR), dicarboxylic acid transporter (DCT_02) transformed with reference fumarate reductase (SEQ ID NO: 33) or mutated fumarate reductase, which contains mutations as compared to the reference sequence in the amino acid positions indicated below.

| PCR | | Mutation in position | | | | | Average succinic acid titer |
|---|---|---|---|---|---|---|---|
| fragment | Clone | 1042 | 1071 | 1072 | 1082 | 1083 | (g/L) |
| — | SUC-723 control | | | | | | 37.4 |
| 11 | Reference | E | N | R | G | F | 49.5 |
| 13 | FCC_040 | R | T | R | K | Y | 55.4 |
| 16 | FCC_048 | R | T | K | R | Y | 54.9 |
| 17 | FCC_065 | K | T | R | R | F | 53.7 |
| 19 | FCC_070 | K | T | K | K | Y | 54.9 |
| 21 | FCC_076 | Q | S | R | K | Y | 58.1 |
| 22 | FCC_078 | Q | S | R | R | Y | 54.6 |

The introduction of a positively charged residue (lysine or arginine; K or R) at amino acid position 1082 is unique, because the reference fumarate reductase sequence contains a small uncharged glycine (G) at this position. Furthermore, no previously described natural variant or publically available mutant of fumarate reductase contains a charged residue at position number 1082. As depicted in Table 4, replacing the glycine at position 1082 in the reference FRDg sequence by a charged residue is advantageous for achieving increased succinic acid titers. In Example 3 this is shown in strain SUC-1099, in this example the same effect is shown in a different strain background, namely strain SUC-723.

Example 9: Measuring NADH and NADPH Specific Activity of Fumarate Reductase (FRD) Variants Expressed in Strain SUC-723

Figure 5A:
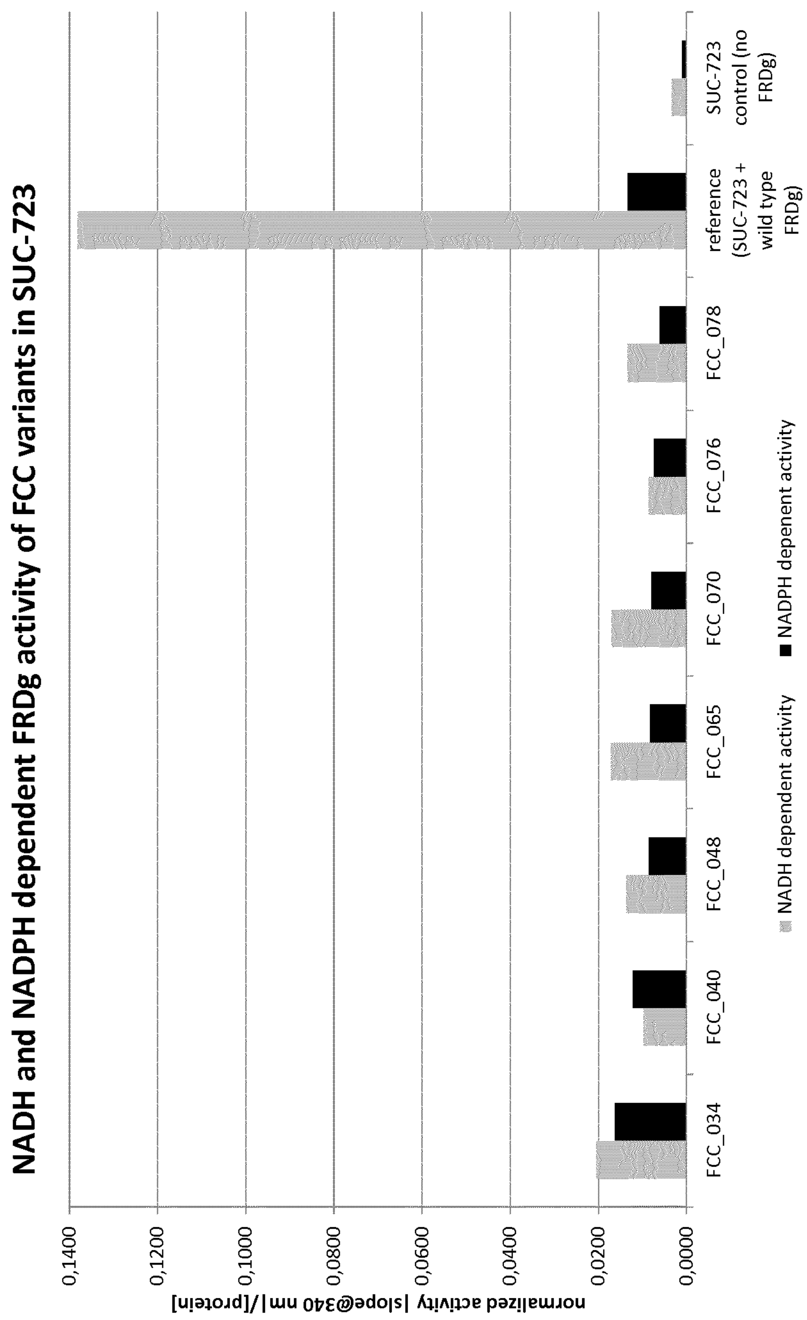
FIG. 5*a*: complete figure.
Figure 5B:
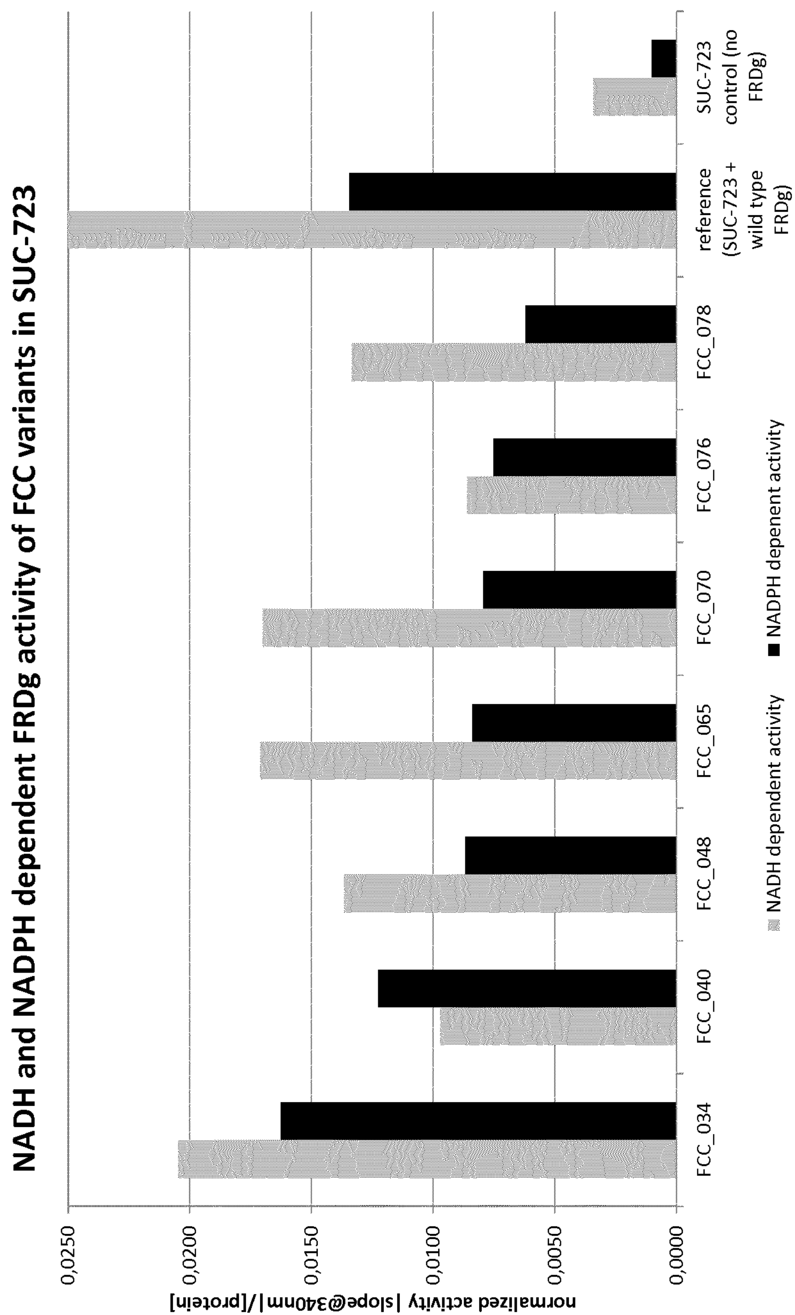
FIG. 5*b*: same graph as in 5a, but zooms in on lower region of y-axis. Label corresponds to value of reference FRD activity. Activity of SUC-723 control (no FRD present) corresponds to background activity in extracts. All values are averages of triplo measurements.

Transformants generated in Example 7 & 8 were grown as described in Example 2. Biomass was harvested, cells were disrupted and protein concentration determined as in Example 4. Fumarate reductase (FRD) activity was assayed spectrophotometrically, in triplo, as in Example 5. FIGS. 5*a* and 5*b* show the NADPH and NADH dependent FRD activities for variants FCC_40, FCC_48, FCC_65, FCC_70, FCC_76, FCC_78 and reference FRD that were expressed in strain SUC-723. A SUC-723 strain not transformed with FRD was taken along as a control. The six FRD variants tested were those variants that contain beneficial mutations for increased succinic production described in Example 3 and Example 8.

Example 10: Transformation of Fumarate Reductase to Strain CEN.PK113-7D

Generation of PCR Fragments

PCR fragment 25 was generated by PCR amplification of SEQ ID NO: 38 using primers amplifying the entire nucleotide sequence of SEQ ID NO: 38. SEQ ID NO: 38 describes the 5' INT09.01 integration flank. SEQ ID NO: 38 includes a 50 bp region of homology to PCR fragment 26 located at the 3' end of SEQ ID NO: 38. The INT09.01 integration site is located 359 bp downstream of the YIL009W ORF on chromosome IX.

PCR fragment 26 was generated by PCR amplification of SEQ ID NO: 39 using primers amplifying the entire nucleotide sequence of SEQ ID NO: 39. SEQ ID NO: 39 encodes a nourseothricin selection marker functional in *Saccharomyces cerevisiae* which was amplified from a modified version of plasmid pUG7-Nat. pUG7-Nat is a variant of plasmid pUG6 described by Gueldener et al., (Nucleic Acids Res. 1996 Jul. 1; 24(13):2519-24), in which the loxP sites present in pUG6 were changed into lox66 and lox71 sites (Lambert et al., Appl. Environ. Microbiol. 2007 Feburary; 73(4):1126-35. Epub 2006 Dec. 1) and in which the KanMX marker was replaced by a nourseothricin marker (Goldstein and McCusker, Yeast. 1999 October; 15(14):1541-53).

PCR fragment 27 was generated by PCR amplification of SEQ ID NO: 40 using primers amplifying the entire nucleotide sequence of SEQ ID NO: 40.

SEQ ID NO: 40 encodes fumarate reductase (FRDg) from *Trypanosoma brucei*, as disclosed in patent application WO2009/065778 and described in SEQ ID NO: 33. This synthetic sequence, which includes promoter-gene-terminator sequence, including appropriate restriction sites, was synthesized by DNA 2.0 (Menlo Park, Calif., USA).

The gene sequence was codon pair optimized for expression in *S. cerevisiae* as disclosed in patent application WO2008/000632. The synthetic gene is under control of (or operable linked to) a promoter from *Kluyveromyces lactis*, i.e. the PGK1 3-phosphoglycerate kinase (uniprot accession number P14828) promoter controls the expression of the FRDg-gene. Proper termination is controlled by a terminator sequence from *S. cerevisiae*, i.e. the ADH1-terminator.

PCR fragment 28 was generated by PCR amplification of SEQ ID NO: 41 using primers amplifying the entire nucleotide sequence of SEQ ID NO: 41. SEQ ID NO: 41 describes the 3' INT09.01 integration flank. The 5' end of PCR fragment 28 consists of a 50 bp region homologous to the 3' end of PCR fragment 27 and fragment 29 to 58.

PCR fragments 29 to 58 were generated in a manner similar to the generation of PCR product 27. Instead of SEQ ID NO: 40 as target for the PCR of fragment 27, synthetic nucleotide sequences were used that encode different protein variants of the reference fumarate reductase sequence that is described in SEQ ID NO: 33. The synthetic nucleotide sequences were synthesized by DNA 2.0 (Menlo Park, Calif., USA). The synthetic nucleotide sequences encode a mutated amino acid relative to the reference FRDg sequence (SEQ ID NO: 33) at the positions indicated in Table 5.

Apart from encoding the indicated mutated amino acids in Table 5 the synthetic nucleotide sequence variants are identical to SEQ ID NO: 40. The sequences were amplified by PCR using the primers used for the amplification of PCR fragment 27 to generate PCR fragments 29 to 58 (see Table 5).

TABLE 5 mutations present in the mutated fumarate reductase variants present on PCR fragments 29 to 58 compared to reference fumarate reductase on PCR fragment 27 (SEQ ID NO: 33). In PCR fragments 29 to 60 mutations are present at amino acid positions 1042, 1071, 1072, 1082 and 1083 as indicated below.

| PCR fragment | clone | 1042 | 1071 | 1072 | 1082 | 1083 |
|---|---|---|---|---|---|---|
| 27 | FRDg | E | N | R | G | F |
| 29 | FCC_097 | R | G | R | R | Y |
| 30 | FCC_098 | Q | G | R | R | Y |
| 31 | FCC_099 | R | G | R | K | Y |
| 32 | FCC_100 | Q | G | R | K | Y |

TABLE 5-continued mutations present in the mutated fumarate reductase variants present on PCR fragments 29 to 58 compared to reference fumarate reductase on PCR fragment 27 (SEQ ID NO: 33). In PCR fragments 29 to 60 mutations are present at amino acid positions 1042, 1071, 1072, 1082 and 1083 as indicated below.

| PCR fragment | clone | 1042 | 1071 | 1072 | 1082 | 1083 |
|---|---|---|---|---|---|---|
| 33 | FCC_101 | R | S | R | R | I |
| 34 | FCC_102 | R | G | R | R | I |
| 35 | FCC_103 | Q | S | R | R | I |
| 36 | FCC_104 | Q | G | R | R | I |
| 37 | FCC_105 | R | S | R | K | I |
| 38 | FCC_106 | R | G | R | K | I |
| 39 | FCC_107 | Q | S | R | K | I |
| 40 | FCC_108 | Q | G | R | K | I |
| 41 | FCC_109 | R | S | R | R | A |
| 42 | FCC_110 | R | G | R | R | A |
| 43 | FCC_111 | Q | S | R | R | A |
| 44 | FCC_112 | Q | G | R | R | A |
| 45 | FCC_113 | R | S | R | K | A |
| 46 | FCC_114 | R | G | R | K | A |
| 47 | FCC_115 | Q | S | R | K | A |
| 48 | FCC_116 | Q | G | R | K | A |
| 49 | FCC_117 | R | S | R | R | S |
| 50 | FCC_118 | R | G | R | R | S |
| 51 | FCC_119 | Q | S | R | R | S |
| 52 | FCC_120 | Q | G | R | R | S |
| 53 | FCC_121 | R | S | R | K | S |
| 54 | FCC_122 | R | G | R | K | S |
| 55 | FCC_123 | Q | S | R | K | S |
| 56 | FCC_124 | Q | G | R | K | S |
| 57 | FCC_030 | R | S | R | R | Y |
| 58 | FCC_028 | R | S | R | K | Y |

Transformation to CEN.PK113-7D in Order to Construct Strain CPK-FRDg

Yeast transformation was done by a method known by persons skilled in the art. *S. cerevisiae* strain CENPK. 113-7D (MATa HIS3 LEU2 TRP1 MAL2-8 SUC2) was transformed with purified PCR fragments 25 to 28. PCR fragments 26 and 27 contained overlaps at their 5' and 3' ends and PCR fragments 25 and 26 at their 3' and 5' end respectively, such that this allowed homologous recombination of all four PCR fragments. The 5' end of PCR fragment 25 and the 3' end of PCR fragment 28 were homologous to the INT09.01 locus and enabled integration of all four PCR fragments in the INT09.01 locus (see FIG. 6).

Transformation mixtures were plated on YEPh-agar (per liter: 10 grams yeast extract, 20 grams PhytonePeptone, 20 grams galactose, 20 grams agar)) containing 100 μg nourseothricin (Jena Bioscience, Germany) per ml. After three days of growth at 30° C., individual transformants were re-streaked on YEPh-agar plates containing 20 grams galactose per liter and 100 μg nourseothricin per ml. Presence of the introduced genes was confirmed by using PCR using primer sequences that can anneal to the coding sequences of the ORF's encoded by SEQ ID NO: 39 and SEQ ID NO: 40. An individual colonies was selected and named CPK-FRDg.

Transformation to CEN.PK113-7D in Order to Construct strain CPK-FCC 097 to CPK-FCC 124 and CPK-FCC 030 and CPK-FCC 028.

Figure 6:
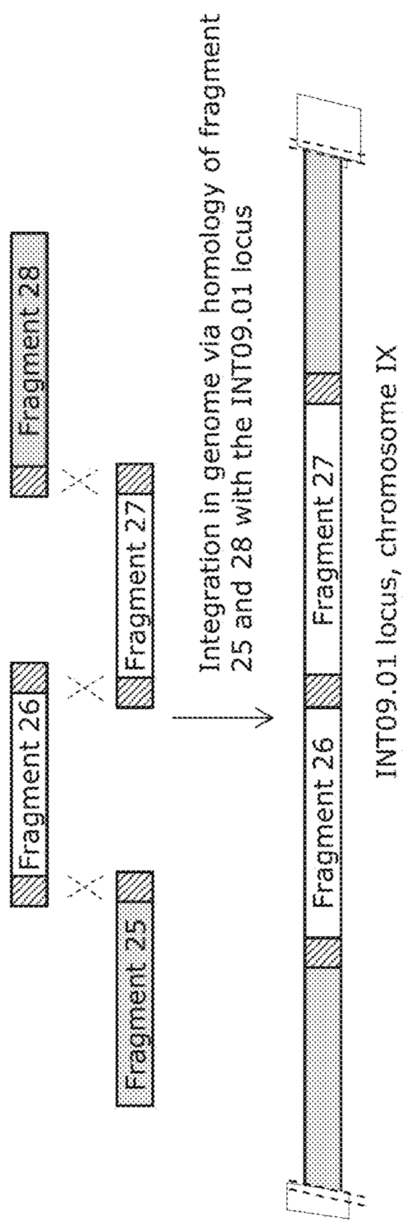
FIG. 6 shows a schematic depiction of integration of fragments 25 to 28. The striped parts indicated in fragments 25 to 28 denote the unique homologous overlap regions leading to the recombination events as indicated by the dashed crosses between the homologous regions. Fragment 27 can be substituted for fragment 29 to 58 individually. Fragment 25 and fragment 28 are homologous to the downstream and upstream regions of the INT09.01 locus on chromosome IX, 359 bp downstream of the YIL009W ORF. Homologous recombination results in integration of fragment 26 and 27 or 29 to 58 individually, 23 and 24 into the INT09.01 locus.

Yeast transformation was done by a method known by persons skilled in the art. *S. cerevisiae* strain CENPK. 113-7D (MATa HIS3 LEU2 TRP1 MAL2-8 SUC2) was transformed with purified PCR fragments 25, 26, 28 and fragment 29 to 58 individually. PCR fragments 26 and fragment 29 to 58 contained overlaps at their 5' and 3' ends and PCR fragments 25 and 28 at their 3' and 5' end respectively, such that this allowed homologous recombination of all four PCR fragments as indicated in FIG. 6. The 5' end of PCR fragment 25 and the 3' end of PCR fragment 28 were homologous to the INT09.01 locus and enabled integration of all four PCR fragments in the INT09.01 locus (see FIG. 6).

Transformation mixtures were plated on YEPh-agar (per liter: 10 grams yeast extract, 20 grams PhytonePeptone, 20 grams galactose, 20 grams agar)) containing 100 μg nourseothricin (Jena Bioscience, Germany) per ml. After three days of growth at 30° C., individual transformants were re-streaked on YEPh-agar plates containing 20 grams galactose per liter and 100 μg nourseothricin per ml. Presence of the introduced genes was inferred from measurement of fumarate reductase enzyme activity.

Example 11: Measuring NADH and NADPH Specific Activity of Fumarate Reductase (FRD) Variants Expressed in Strain CEN.PK113-7

Figure 7:
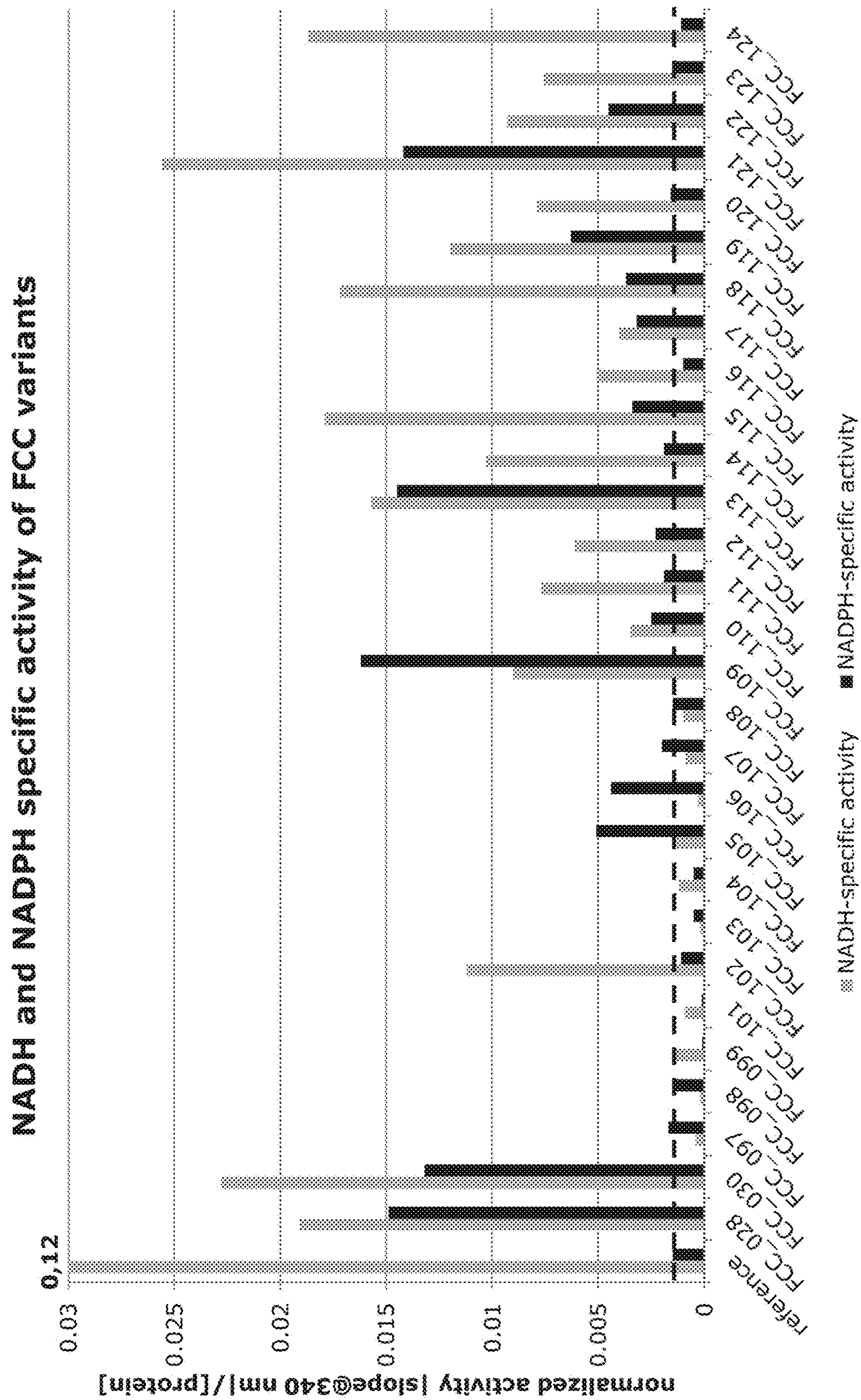
FIG. 7 shows NADH and NADPH dependent fumarate reductase (FRD) activity of FCC variants expressed in strain CEN.PK113-7D. Shown is the normalized activity, determined as the change in absorbance at 340 nm ($min^{-1}$) divided by total protein concentration (mg $mL^{-1}$) of the soluble cell extract, which is a measure for the fumarate reductase activity. Equal amounts of soluble extracts were used to test the NADH and NADPH dependent activity of each variant, so that the effect of the mutation on cofactor specificity can be determined for each variant. Clear is that all exhibited significantly altered cofactor specificity when compared to the reference (wild type FRD protein minus C-terminal SKI). This is evidenced by the fact that in all cases the NADH-dependent FRD activity is significantly reduced compared to the reference, a reduction between four- and fifty-fold. Surprisingly, for several variants the cofactor specificity has been completely switched from NADH to NADPH, namely FCC_097, 098, 105, 106, 107, 108 & 109. These variants prefer NADPH over NADH as cofactor for the fumarate reductase reaction; the increase in NADPH-specific normalized activity is up to ~11-fold higher than for the reference. Surprisingly, the position that appears to be responsible for this complete NADH- to NADPH-specificity switch is residue 1083. Mutating this residue, in combination with the other residues, from a bulky aromatic residue to a smaller hydrophobic residue (e.g. isoleucine or alanine) causes the cofactor specificity to be switched completely. The dotted line denotes the reference (background) NADPH-specific FRD activity.

Transformants generated in Example 10 were grown in 24-well deepwell plates (Axygen) in Verduyn medium (Verduyn C, Postma E, Scheffers W A, Van Dijken J P. Yeast, 1992 July; 8(7):501-517) with galactose as carbon source and containing 150 μg nourseothricin (Jena Bioscience, Germany) per ml. Biomass was harvested, cells were disrupted and protein concentration determined as in Example 4. Fumarate reductase (FRD) activity was assayed spectrophotometrically as in Example 4, with the following minor modifications: 400 μM NADH or NADPH was used instead of 150 μM. The measured activities were normalized for total protein present by dividing by the total protein concentration in the assay, as determined by Bradford using bovine serum albumin as standard. Table 6 lists the specificity ratio for each variant; the ratio of NADPH:NADH dependent activity=(slope at 340 nm with NADPH)/(slope at 340 nm with NADH). This ratio was calculated so that the variants could be ranked on altered cofactor specificity (see: Table 6). An increased value for the ratio compared to the reference clone indicated that the cofactor specificity had been altered. This can indicate reduced NADH specificity, increased NADPH activity or a combination of the two. FIG. 7 shows the NADPH and NADH dependent FRD activities for FRD variants expressed in CEN.PK113-7D. A CEN.PK113-7D strain not transformed with FRD was taken along as a negative control.

TABLE 6

NADPH:NADH specificity ratio for FRD variants expressed in strain CEN.PK113-7D. By calculating the ratio between the NADPH and NADH specific FRD activity, the variants could be ranked and easily compared to the reference sequence. Surprisingly, all variants displayed an altered cofactor specificity, many very dramatically so, when compared to the reference FRD, as evidenced by a different specificity ratio.

| PCR fragment | Clone | Mutation in position 1042 | 1071 | 1072 | 1082 | 1083 | Ratio NADH:NADPH dependent activity |
|---|---|---|---|---|---|---|---|
| — | CEN.PK113-7D control | | | | | | n.a. |
| 27 | Reference | E | N | R | G | F | 0.01 |
| 59 | FCC_028 | R | S | R | K | Y | 0.6 |
| 57 | FCC_030 | R | S | R | R | Y | 0.8 |
| 29 | FCC_097 | R | G | R | R | Y | 3.9 |
| 30 | FCC_098 | Q | G | R | R | Y | 5.5 |
| 31 | FCC_099 | R | G | R | K | Y | 0.04 |
| 32 | FCC_100 | Q | G | R | K | Y | 0.5 |
| 33 | FCC_101 | R | S | R | R | I | 0.2 |
| 34 | FCC_102 | R | G | R | R | I | 0.1 |
| 35 | FCC_103 | Q | S | R | R | I | 2.3 |
| 36 | FCC_104 | Q | G | R | R | I | 0.4 |
| 37 | FCC_105 | R | S | R | K | I | 4.0 |
| 38 | FCC_106 | R | G | R | K | I | 12.7 |
| 39 | FCC_107 | Q | S | R | K | I | 2.2 |
| 40 | FCC_108 | Q | G | R | K | I | 1.5 |
| 41 | FCC_109 | R | S | R | R | A | 1.8 |
| 42 | FCC_110 | R | G | R | R | A | 0.7 |
| 43 | FCC_111 | Q | S | R | R | A | 0.2 |
| 44 | FCC_112 | Q | G | R | R | A | 0.4 |
| 45 | FCC_113 | R | S | R | K | A | 0.9 |
| 46 | FCC_114 | R | G | R | K | A | 0.2 |
| 47 | FCC_115 | Q | S | R | K | A | 0.2 |
| 48 | FCC_116 | Q | G | R | K | A | 0.2 |
| 49 | FCC_117 | R | S | R | R | S | 0.8 |
| 50 | FCC_118 | R | G | R | R | S | 0.2 |
| 51 | FCC_119 | Q | S | R | R | S | 0.5 |
| 52 | FCC_120 | Q | G | R | R | S | 0.2 |
| 53 | FCC_121 | R | S | R | K | S | 0.6 |
| 54 | FCC_122 | R | G | R | K | S | 0.5 |
| 55 | FCC_123 | Q | S | R | K | S | 0.2 |
| 56 | FCC_124 | Q | G | R | K | S | 0.1 |

The invention claimed is:

1. A variant polypeptide having fumarate reductase activity, wherein the variant polypeptide has modified NADP(H)-dependent activity and/or modified NAD(H)-dependent activity as compared with a reference polypeptide having fumarate reductase activity and comprising the amino acid sequence of SEQ ID NO: 33, wherein the variant polypeptide comprises an amino acid sequence which, when aligned with the fumarate reductase comprising the amino acid sequence of SEQ ID NO: 33, comprises at least one substitution of an amino acid residue corresponding to any of amino acids 1042, 1071, 1072, 1082 or 1083 said positions being defined with reference to SEQ ID NO: 33, wherein the variant polypeptide is a non-naturally occurring polypeptide, and wherein the variant polypeptide is at least 85% identical to SEQ ID NO: 33.

2. A variant polypeptide according to claim 1 which has increased NADP(H)-dependent activity as compared with the reference polypeptide.

3. A variant polypeptide according to claim 1 which has decreased NAD(H)-dependent activity as compared with the reference polypeptide.

4. A variant polypeptide according to claim 1, wherein the modified NADP(H)-dependent activity is increased NADP(H)-dependent activity, and the modified NAD(H)-dependent activity is decreased NAD(H)-dependent activity.

5. A variant polypeptide according to claim 1, which comprises additional substitutions other than at least one substitution of an amino acid residue corresponding to any of amino acids 1042, 1071, 1072, 1082 or 1083 said positions being defined with reference to SEQ ID NO: 33.

6. A variant polypeptide according to claim 1, wherein the variant polypeptide comprises:

a) R, K, or Q at position 1042 as defined with reference to SEQ ID NO: 33;

b) G, T, or S at position 1071 as defined with reference to SEQ ID NO: 33;

c) K at position 1072 as defined with reference to SEQ ID NO: 33;

d) K or Rat position 1082 as defined with reference to SEQ ID NO: 33; and/or e) S, Y, I, or A at position 1083 as defined with reference to SEQ ID NO: 33.

7. A nucleic acid comprising sequence encoding a variant polypeptide according to claim 1.

8. A nucleic acid construct comprising the nucleic acid sequence of claim 7 operably linked to one or more control sequences capable of directing the expression of a fumarate reductase in a suitable expression host.

9. An expression vector comprising a nucleic acid according to claim 7 or a nucleic acid construct comprising the nucleic acid sequence operably linked to one or more control sequences capable of directing the expression of a fumarate reductase in a suitable expression host.

10. An isolated host cell comprising a nucleic acid according to claim 7, a nucleic acid construct comprising the nucleic acid sequence operably linked to one or more control sequences capable of directing the expression of a fumarate reductase in a suitable expression host or an expression vector comprising said nucleic acid or said nucleic acid construct.

11. An isolated host cell according to claim 10 which is a prokaryotic cell, optionally a bacterial cell, or a eukaryotic cell, optionally a yeast cell or a filamentous fungal cell.

12. An isolated host cell according to claim 11, wherein the yeast cell is a *Saccharomyces cerevisiae* host cell.

13. A method for producing a fumarate reductase comprising cultivating a host cell according to claim 10 under conditions suitable for production of the fumarate reductase and, optionally, recovering fumarate reductase.

14. A method for the production of a dicarboxylic acid, optionally succinic acid, which method comprises fermenting a host cell according to claim 10 under conditions suitable for production of succinic acid and, optionally, recovering succinic acid.

15. A variant polypeptide according to claim 1 having at least 90% sequence identity with SEQ ID NO: 33.

16. A variant polypeptide according to claim 1 having at least 95% sequence identity with SEQ ID NO: 33.

17. A variant polypeptide according to claim 1 having at least 99% sequence identity with SEQ ID NO: 33.

18. A variant polypeptide according to claim 1, which has an increase in NADP(H)-dependent activity relative to NAD(H)-dependent activity as compared with the reference polypeptide.

* * * * *